US012729381B2

(12) United States Patent
Karimi et al.

(10) Patent No.: US 12,729,381 B2
(45) Date of Patent: Sep. 8, 2026

(54) METHODS AND COMPOSITIONS FOR INACTIVATING INTERLEUKIN-2-INDUCIBLE T-CELL KINASE (ITK)

(71) Applicant: The Research Foundation for the State University of New York, Albany, NY (US)

(72) Inventors: Mobin Karimi, Manlius, NY (US); Alaji Bah, Baldwinsville, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 786 days.

(21) Appl. No.: 17/918,230

(22) PCT Filed: Apr. 9, 2021

(86) PCT No.: PCT/US2021/026724
§ 371 (c)(1),
(2) Date: Oct. 11, 2022

(87) PCT Pub. No.: WO2021/207706
PCT Pub. Date: Oct. 14, 2021

(65) Prior Publication Data
US 2023/0141417 A1 May 11, 2023

Related U.S. Application Data

(60) Provisional application No. 63/007,593, filed on Apr. 9, 2020.

(51) Int. Cl.
*C12N 15/113* (2010.01)

(52) U.S. Cl.
CPC ...... *C12N 15/1137* (2013.01); *C12N 2310/14* (2013.01)

(58) Field of Classification Search
CPC .... A61K 38/1709; C07K 14/47; C12N 14/47; C12N 2310/14
See application file for complete search history.

(56) References Cited

PUBLICATIONS

Whisstock et al. (Biophysics, 2003 vol. 36:307-340).*
Seffernick et al. (Journal of Bacteriology, 2001 vol. 183:2405-2410).*

* cited by examiner

*Primary Examiner* — Terra C Gibbs
(74) *Attorney, Agent, or Firm* — Peter Fallon

(57) ABSTRACT

The present disclosure relates to compositions and methods for administering a subject in need thereof an effective amount of an inhibitor of interleukin-2-inducible T-cell kinase (ITK). In embodiments, the polypeptide of the present disclosure is characterized as an inhibitor and includes an amino acid sequence having at least 80% sequence identity to SEQ ID NO: 2, wherein the peptide inhibitor includes a phosphorylated tyrosine.

4 Claims, 40 Drawing Sheets

Specification includes a Sequence Listing.

A

D

E

| Pathway of Differentiated Expression genes *Itk*$^{-/-}$ to WT | |
|---|---|
| KEGG pathways | adjusted p-value |
| Cytokine/Cytokine Receptor Interaction | $7.2x10^{-8}$ |
| Cell Adhesion Molecules | $7.7x10^{-7}$ |
| Graft-Versus-Host Disease | $9.7x10^{-6}$ |
| Allograft Rejection | $3x10^{-3}$ |
| Chemokine Signaling Pathway | 0.09 |

FIGS. 14A - 14D
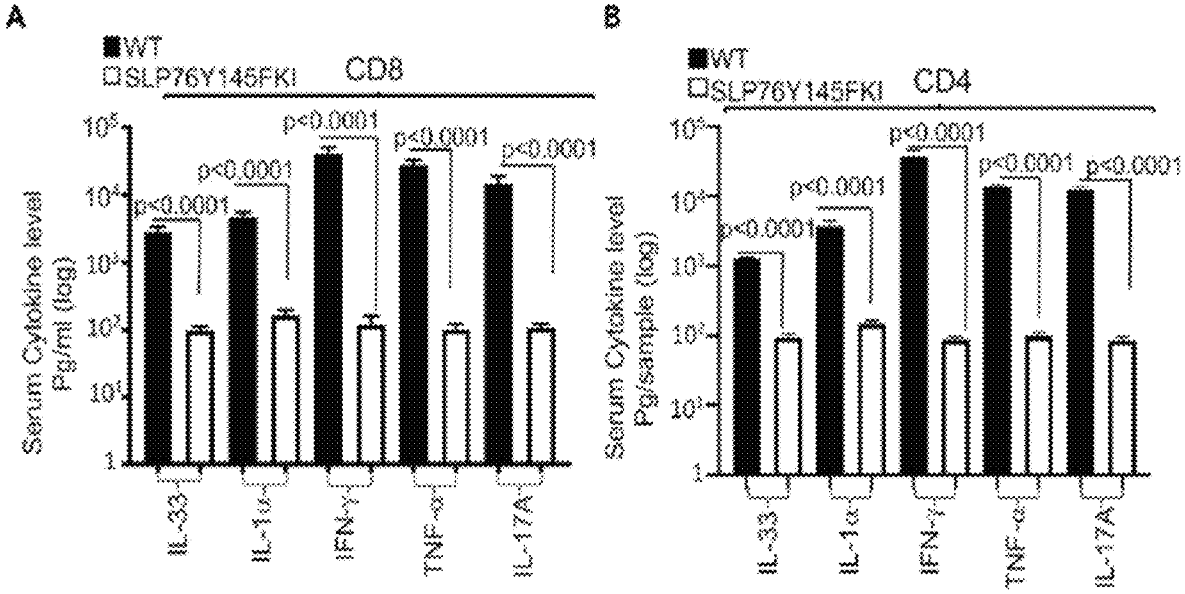
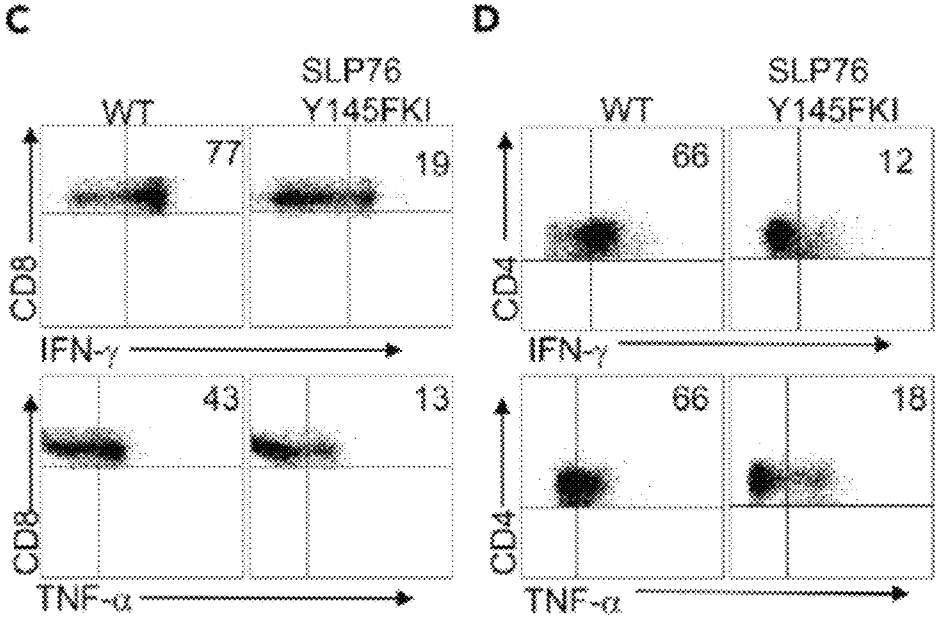

SLP76pTYR peptide
Fusion sequences:
GCCACGATG - mCherry Sequence (708 Nucleotides - 236 Amino Acids AY678264)
ATGTACGGC - mCherry Chromophore (MYG)
ATGGTGGGT – SLP76pTYR LINKER - 10 Amino Acids (30 Nucleotides) between mCherry and SLP76pTYR ATG - Methionine Start Codon TAG TAA TGA - Stop Codons ACGCGT – MluI CTCGAG - XhoI ACGCGTGCCACCACGTCAGATCCGCTAGCGCCACC
aacgaagaagaagaagcgccggtggaagatgatgcggattatgaaccgccgccgagcaac GatgaagaagcgGGCGGTAGCGGGGATCCACCGGTCGCCACCATGGTGAGCAAGGGCGAGGAGGATAACATGGCCATCATC
AAGGAGTTCATGCGCTTCAAGGTGCACATGGAGGGCTCCGTGAACGGCCACGAGTTCGAGATCGAGGGCGAGGGCGAG
GGCCGCCCCTACGAGGGCACCCAGACCGCCAAGCTGAAGGTGACCAAGGGTGGCCCCCTGCCCTTCGCCTGGGACATCCT
GTCCCCTCAGTTCATGTACGGCTCCAAGGCCTACGTGAAGCACCCCGCCGACATCCCCGACTACTTGAAGCTGTCCTTCCCC
GAGGGCTTCAAGTGGGAGCGCGTGATGAACTTCGAGGACGGCGGCGTGGTGACCGTGACCCAGGACTCCTCCCTGCAGG
ACGGCGAGTTCATCTACAAGGTGAAGCTGCGCGGCACCAACTTCCCCTCCGACGGCCCCGTAATGCAGAAGAAGACCATG
GGCTGGGAGGCCTCCTCCGAGCGGATGTACCCCGAGGACGGCGCCCTGAAGGGCGAGATCAAGCAGAGGCTGAAGCTG
AAGGACGGCGGCCACTACGACGCTGAGGTCAAGACCACCTACAAGGCCAAGAAGCCCGTGCAGCTGCCCGGCGCCTACA
ACGTCAACATCAAGTTGGACATCACCTCCCACAACGAGGACTACACCATCGTGGAACAGTACGAACGCGCCGAGGGCCGC
CACTCCACCGGCGGCATGGACGAGCTGTACAAGTAAAGCGGCCGCGACTCTAGATCATAATCAGCCATACCACATCTCGAG

SEQUENCE LISTING

<160> NUMBER OF SEQ ID NOS: 6

<210> SEQ ID NO 1
<211> LENGTH: 72
<212> TYPE: DNA
<213> ORGANISM: Artificial Sequence
<220> FEATURE:
<223> OTHER INFORMATION: Synthetic sequence

<400> SEQUENCE: 1
aacgaagaag aagaagcgcc ggtggaagat gatgcggatt atgaaccgcc gccgagcaac 60
gatgaagaag cg 72

<210> SEQ ID NO 2
<211> LENGTH: 24
<212> TYPE: PRT
<213> ORGANISM: Artificial Sequence
<220> FEATURE:
<223> OTHER INFORMATION: Synthetic sequence

<400> SEQUENCE: 2

```
Asn Glu Glu Glu Glu Ala Pro Val Glu Asp Asp Ala Asp Tyr Glu Pro
1               5                   10                  15

Pro Pro Ser Asn Asp Glu Glu Ala
            20
```

<210> SEQ ID NO 3
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 3

```
Gly Arg Lys Lys Arg Arg Gln Arg Arg Arg Pro Gln
1               5                   10
```

<210> SEQ ID NO 4
<211> LENGTH: 533
<212> TYPE: PRT
<213> ORGANISM: Homo sapiens

<400> SEQUENCE: 4

```
Met Ala Leu Arg Asn Val Pro Phe Arg Ser Glu Val Leu Gly Trp Asp
1               5                   10                  15

Pro Asp Ser Leu Ala Asp Tyr Phe Lys Lys Leu Asn Tyr Lys Asp Cys
            20                  25                  30

Glu Lys Ala Val Lys Lys Tyr His Ile Asp Gly Ala Arg Phe Leu Asn
        35                  40                  45

Leu Thr Glu Asn Asp Ile Gln Lys Phe Pro Lys Leu Arg Val Pro Ile
    50                  55                  60

Leu Ser Lys Leu Ser Gln Glu Ile Asn Lys Asn Glu Glu Arg Arg Ser
65                  70                  75                  80

Ile Phe Thr Arg Lys Pro Gln Val Pro Arg Phe Pro Glu Glu Thr Glu
                85                  90                  95

Ser His Glu Glu Asp Asn Gly Gly Trp Ser Ser Phe Glu Glu Asp Asp
            100                 105                 110

Tyr Glu Ser Pro Asn Asp Asp Gln Asp Gly Glu Asp Asp Gly Asp Tyr
        115                 120                 125

Glu Ser Pro Asn Glu Glu Glu Glu Ala Pro Val Glu Asp Asp Ala Asp
    130                 135                 140
```

```
Tyr Glu Pro Pro Pro Ser Asn Asp Glu Glu Ala Leu Gln Asn Ser Ile
145                 150                 155                 160

Leu Pro Ala Lys Pro Phe Pro Asn Ser Asn Ser Met Tyr Ile Asp Arg
                165                 170                 175

Pro Pro Ser Gly Lys Thr Pro Gln Gln Pro Pro Val Pro Pro Gln Arg
            180                 185                 190

Pro Met Ala Ala Leu Pro Pro Pro Pro Ala Gly Arg Asn His Ser Pro
        195                 200                 205

Leu Pro Pro Pro Gln Thr Asn His Glu Glu Pro Ser Arg Ser Arg Asn
    210                 215                 220

His Lys Thr Ala Lys Leu Pro Ala Pro Ser Ile Asp Arg Ser Thr Lys
225                 230                 235                 240

Pro Pro Leu Asp Arg Ser Leu Ala Pro Phe Asp Arg Glu Pro Phe Thr
                245                 250                 255

Leu Gly Lys Lys Pro Pro Phe Ser Asp Lys Pro Ser Ile Pro Ala Gly
            260                 265                 270

Arg Ser Leu Gly Glu His Leu Pro Lys Ile Gln Lys Pro Pro Leu Pro
        275                 280                 285

Pro Thr Thr Glu Arg His Glu Arg Ser Ser Pro Leu Pro Gly Lys Lys
    290                 295                 300

Pro Pro Val Pro Lys His Gly Trp Gly Pro Asp Arg Arg Glu Asn Asp
305                 310                 315                 320

Glu Asp Asp Val His Gln Arg Pro Leu Pro Gln Pro Ala Leu Leu Pro
                325                 330                 335

Met Ser Ser Asn Thr Phe Pro Ser Arg Ser Thr Lys Pro Ser Pro Met
            340                 345                 350

Asn Pro Leu Pro Ser Ser His Met Pro Gly Ala Phe Ser Glu Ser Asn
        355                 360                 365

Ser Ser Phe Pro Gln Ser Ala Ser Leu Pro Pro Tyr Phe Ser Gln Gly
    370                 375                 380

Pro Ser Asn Arg Pro Pro Ile Arg Ala Glu Gly Arg Asn Phe Pro Leu
385                 390                 395                 400

Pro Leu Pro Asn Lys Pro Arg Pro Pro Ser Pro Ala Glu Glu Glu Asn
                405                 410                 415

Ser Leu Asn Glu Glu Trp Tyr Val Ser Tyr Ile Thr Arg Pro Glu Ala
            420                 425                 430

Glu Ala Ala Leu Arg Lys Ile Asn Gln Asp Gly Thr Phe Leu Val Arg
        435                 440                 445

Asp Ser Ser Lys Lys Thr Thr Thr Asn Pro Tyr Val Leu Met Val Leu
    450                 455                 460

Tyr Lys Asp Lys Val Tyr Asn Ile Gln Ile Arg Tyr Gln Lys Glu Ser
465                 470                 475                 480

Gln Val Tyr Leu Leu Gly Thr Gly Leu Arg Gly Lys Glu Asp Phe Leu
                485                 490                 495

Ser Val Ser Asp Ile Ile Asp Tyr Phe Arg Lys Met Pro Leu Leu Leu
            500                 505                 510

Ile Asp Gly Lys Asn Arg Gly Ser Arg Tyr Gln Cys Thr Leu Thr His
        515                 520                 525

Ala Ala Gly Tyr Pro
    530

<210> SEQ ID NO 5
<211> LENGTH: 36
```

-continued

```
<212> TYPE: PRT
<213> ORGANISM: Artificial Sequence
<220> FEATURE:
<223> OTHER INFORMATION: Synthetic Sequence

<400> SEQUENCE: 5

Asn Glu Glu Glu Glu Ala Pro Val Glu Asp Asp Ala Asp Tyr Glu Pro
1               5                   10                  15

Pro Pro Ser Asn Asp Glu Glu Ala Gly Arg Lys Lys Arg Arg Gln Arg
            20                  25                  30

Arg Arg Pro Gln
        35


<210> SEQ ID NO 6
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 6

Ile Ile Met Thr Thr Thr Thr Asn Asn Lys Lys Ser Ser Arg Arg Val
1               5                   10                  15

Val Val Val Ala Ala Ala Ala Asp Asp Gly Arg Lys Lys Arg Arg Gln
            20                  25                  30

Arg Arg Arg Pro Gln
        35
```

METHODS AND COMPOSITIONS FOR INACTIVATING INTERLEUKIN-2-INDUCIBLE T-CELL KINASE (ITK)

CROSS REFERENCE TO RELATED APPLICATIONS

This Application is the National Phase entry under 35 U.S.C. § 371 of PCT International Application No. PCT/US2021/26724, filed Apr. 9, 2021, which application claims priority to U.S. Provisional Application No. 63/007,593, filed Apr. 9, 2020. The content of this earlier filed application is hereby incorporated by reference herein in its entirety.

GOVERNMENT SUPPORT CLAUSE

This invention was made with government support under grant no. AI130182 awarded by the National Institutes of Health. The government has certain rights in the invention.

INCORPORATION OF THE SEQUENCE LISTING

The present application contains a sequence listing the content of which is hereby incorporated by reference.

SEQUENCE LISTING

The instant application contains a Sequence Listing which has been submitted via Patent Center and is hereby incorporated by reference in its entirety. Said .xml copy, created on Jan. 15, 2026, is named 110-2101US01, and is 12,251 bytes in size.

FIELD OF THE INVENTION

The present disclosure relates to medicine, molecular and cellular biology and biochemistry. In embodiments, the present disclosure includes methods and compositions for hematopoietic stem cell transplantation treatment such as allogeneic hematopoietic stem cell transplantation (allo-HSCT) that maintain graft-versus-tumor (GVT) effects while reducing or eliminating graft-versus-host disease (GVHD) in e.g., subjects with hematologic malignancies, cancer, or other conditions such as diabetes, or graft-versus-host disease. In embodiments, the present disclosure includes suppressors and/of inhibitors of "Inducible T Cell Kinase" (ITK) polypeptides and methods of making and using them, e.g., as agents and pharmaceutical compositions to treat cancer, diabetes, or the like. In embodiments, the present disclosure is directed to ITK protein expression and/or activity suppressors or inhibitors. In one aspect, the ITK protein inhibitors or suppressors of the present disclosure are used to treat cancers while maintaining graft-versus-tumor (GVT) effects and reducing or eliminating graft-versus-host disease (GVHD). In one aspect, the present disclosure is directed to ITK protein inhibitors or suppressors as chimeric proteins including fragments or altered or truncated forms of SLP76 protein, or equivalent. In other aspects SLP76 protein or fragments thereof is joined or fused to another moiety (e.g., a targeting domain or dye). The disclosure also provides pharmaceutical compositions including the ITK protein inhibitors or suppressors of the present disclosure and methods of making and using them, including methods for ameliorating, treating, suppressing or preventing cancer while maintaining graft-versus-tumor (GVT) effects and/or reducing or eliminating graft-versus-host disease (GVHD). The present disclosure also provides compositions for transfecting cells with nucleic acids acting as ITK protein inhibitors or suppressors of the present disclosure and/or the chimeric ITK protein inhibitors or suppressors polypeptides of the present disclosure.

BACKGROUND

During allogeneic hematopoietic stem cell transplantation (allo-HSCT), alloreactive donor T cells are essential for the graft-versus leukemia effect (GVL) (See e.g., Breems, D. A. & Lowenberg, B. Autologous stem cell transplantation in the treatment of adults with acute myeloid leukaemia. *Br J Haemato/*130, 825-833 (2005); Tugues, S. et al. Graft-versus-host disease, but not graft-versus-leukemia immunity, is mediated by GM-CSF-licensed myeloid cells. *Sci Transl Med* 10 (2018; and Mammadli, M. et al. Inhibition of ITK differentiates GVT and GVHD in allo-HSCT. *bioRxiv,* 2020.2007.2015.204693 (2020)). The same donor T cells may also problematically cause significant tissue damage to the host, known as graft-versus-host disease (GVHD) (See e.g., Bastien, J. P., Roy, J. & Roy, D. C. Selective T-cell depletion for haplotype-mismatched allogeneic stem cell transplantation. *Semin Oncol* 39, 674-682 (2012)). Development of GVHD results in significant morbidity and mortality which complicates allo-HSCT, a potentially curative treatment for leukemia. Standard immunosuppressive therapy for GVHD is often therapeutically sub-optimal and predisposes patients to opportunistic infections such as Cytomegalovirus (CMV) and relapse of the underlying malignancy. (See e.g., Ferrara, J. L. Blood and Marrow Transplant Clinical Trials Network: progress since the State of the Science Symposium 2007. *Biol Blood Marrow Transplant* 20, 149-153 (2014), and Bleakley, M., Turtle, C. J. & Riddell, S. R. Augmentation of anti-tumor immunity by adoptive T-cell transfer after allogeneic hematopoietic stem cell transplantation. *Expert Rev Hematol* 5, 409-425 (2012)). Thus, specific signaling pathways that can be targeted to allow the effects of GVL to persist while inhibiting GVHD need to be identified.

Prior art of interest includes U.S. Patent Publication No. 2010/0287636 entitled Compositions and Methods for Inhibiting Inducible T Cell Kinase (ITK) and Treating Asthma and Bronchial Inflammations to Tsoukas, et al. published on 11 Nov. 2010 (herein incorporated by reference in its entirety). However, the reference is deficient in that it refers to different peptides and does not refer to cells that promote or allow for the effects of GVL to persist while inhibiting GVHD.

Traditionally, the pharmacological inhibition of many kinases involved in cancer therapy mostly directly targets the kinase domain by binding to the active site cleft or an allosteric site. This approach has two major drawbacks: (i) these inhibitors are usually non-specific due to high conservation/similarity of the structure of the kinase domains found in different kinases, and/or (ii) the targeted kinase is usually involved in multiple signaling pathways. Thus, kinase domain inhibitors disrupt all the activity-dependent pathways, even those that are not involved in driving the malignancy but are required for other critical pathways. Accordingly, there is a continuous need for improved strategies relating to pharmacological inhibition of kinases.

Further, there is a continuous need for methods and compositions for hematopoietic stem cell transplantation treatment such as allogeneic hematopoietic stem cell transplantation (allo-HSCT) that maintain graft-versus-tumor (GVT) effects while reducing or eliminating graft-versus-host disease (GVHD) in e.g., subjects with hematologic malignancies or cancer. For example there is a need for donor T-cells such as allo-reactive donor T cells in a graft for donor stem cell engraftment for anti-tumor activity (graft-versus-tumor: GVT), that do not cause significant tissue damage to the host known as graft-versus-host disease (GVHD).

SUMMARY

Other features and advantages of the present compositions and methods are illustrated in the description below, the drawings, and the claims.

The present disclosure relates to method including administering a subject in need thereof an effective amount of an inhibitor of interleukin-2-inducible T-cell kinase (ITK) in accordance with the present disclosure.

In some embodiments, the present disclosure relates to a composition including an inhibitor of interleukin-2-inducible T-cell kinase (ITK) selected from a small molecule inhibitor, a nucleic acid inhibitor, and a peptide inhibitor or the present disclosure.

In embodiments, the present disclosure includes one or more nucleic acids encoding peptides of the present disclosure, a vector including a nucleic acid of the present disclosure, or a T-cell including a nucleic acid and/or peptide of the present disclosure. In embodiments, a polypeptide of the present disclosure has at least 80% sequence identity to SEQ ID NO: 2, and the polypeptide includes a phosphorylated tyrosine.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which:

FIGS. 14A-14H depict SLP76Y145FKI donor $CD8^+$ and $CD4^+$ T cells exhibit reduced cytokine production and reduced proliferation.

Figure 1A:
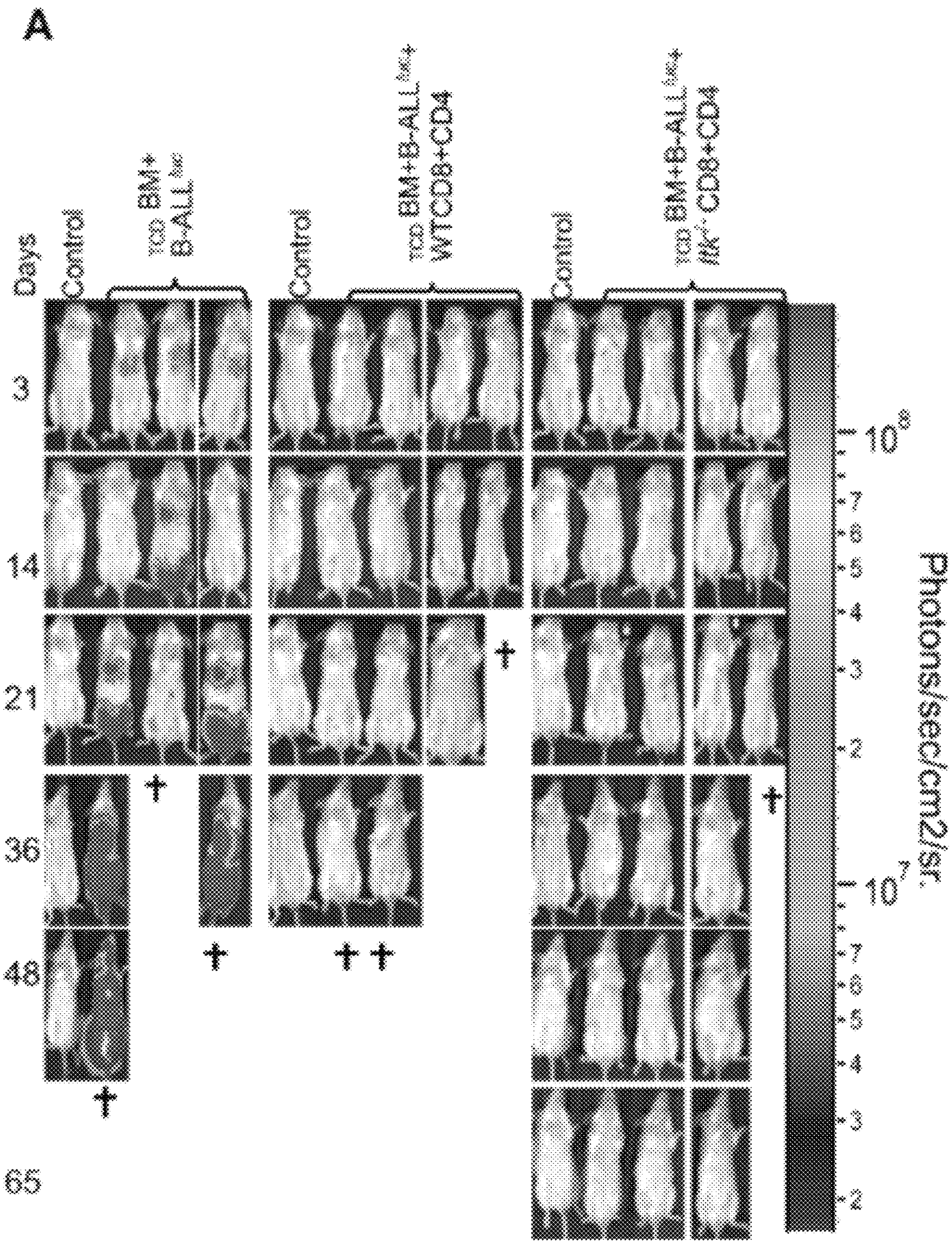
FIGS. 1A-1E depicts absence of ITK avoids GVHD while retaining GVL effects during allo-HSCT.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION

The disclosed methods and compositions may be understood more readily by reference to the following detailed description of particular embodiments and the Examples included therein and to the Figures and their previous and following description.

The present disclosure relates to compositions and methods including administering to a subject in need thereof an effective amount of an inhibitor of interleukin-2-inducible T-cell kinase (ITK).

The inventors show herein that targeting ITK signaling can inhibit GVHD while maintaining GVL function allogeneic transplant model. This finding will have a significant impact on the future development of transplantation strategies. Further, the inventors have developed a specific inhibitor that disrupts SLP76: ITK interactions, leading to reduced inflammatory cytokine production and reduced chemokine receptor upregulation. Moreover, T cells treated with SLP76pTYR exhibit increased numbers of CD25−, FoxP3+ regulatory T cells.

Traditionally, the pharmacological inhibition of many kinases involved in cancer therapy mostly directly targets the kinase domain by binding to the active site cleft or an allosteric site. This approach has two major drawbacks: (i) these inhibitors are usually non-specific due to high conservation/similarity of the structure of the kinase domains found in different kinases, and/or (ii) the targeted kinase is usually involved in multiple signaling pathways. Thus, kinase domain inhibitors disrupt all the activity-dependent pathways, even those that are not involved in driving the malignancy but are required for other critical pathways. The present disclosure provides innovative methodology or strategy focusing on specifically disrupting the kinase docking to a specific scaffold-of-interest without inhibiting its activity or affecting its ability to be involved in other pathways. This approach is critical for eliciting its desirable GVL effects during allo-HSCT. This new and different approach to inhibiting ITK signaling is expected to allow for overcoming the limitations of current ITK inhibitors.

The inventors have also shown that SLP76145pTYR specifically inhibits the phosphorylation of ITK and downstream signaling molecules, including PLC-γ1, and ERK, without affecting the phosphorylation of other signaling molecules. Furthermore, treating T cells from GVHD patient blood samples with SLP76pTYR enhances the development of $FoxP3^+$ regulatory T cells, while significantly reducing IFN-γ and TNF-α production by T cells from GVHD patient blood samples.

Moreover, the inventors have found that inactivating or inhibiting the interleukin-2-inducible T-cell kinase (ITK) gene in T-cell significantly reduces production of inflammatory cytokines and migration of the T cells to graft-versus-host disease (GVHD) target organs, while retaining the therapeutic graft-versus-tumor effect of the T-cells intact. This disclosure is directed to methods and compositions for inactivating the ITK gene in a subject in need of such treatment.

In some embodiments, a subject such as a human or non-human mammal (such as a dog, cat, monkey, horse, mouse, rat, or the like) is suffering from a disorder with an inflammatory component. In some embodiments, the subject is suffering from a cancer and is receiving a T-cell-based immunotherapy. In some embodiments, the subject is suffering from a T-cell lymphoma. In some embodiments, the subject is suffering from diabetes. In some embodiments, the subject is suffering from atherosclerosis. In some embodiments, the subject is suffering from GVHD. In some embodiments, the subject has had or is planning to have organ transplantation. In some embodiments, the subject has had or is planning to have a skin graft. In some embodiments, the methods of this disclosure can prevent or treat GVHD.

Methods of Treatment

In some embodiments, the present disclosure is directed to methods of treating a subject by administering the subject an effective amount of an inhibitor of interleukin-2-inducible T-cell kinase (ITK) of the present disclosure. As used herein, the term "effective amount" means the total amount of each active component of a pharmaceutical composition or method that is sufficient to show a meaningful patient benefit, i.e., treatment, healing, prevention of the relevant medical condition, amelioration of the symptoms, or an increase in rate of treatment, healing, prevention or amelioration of such conditions, or inhibition of the progression of the condition. When applied to an individual active ingredient, administered alone, the term refers to that ingredient alone. When applied to a combination, the term refers to combined amounts of the active ingredients that result in a desired therapeutic effect, whether administered in combination, serially or simultaneously.

In embodiments, the disclosure is directed to methods involving immunotherapy approaches. In some embodiments, the methods of the instant disclosure include providing a T cell to a subject, wherein the interleukin-2-inducible T-cell kinase (ITK) gene in the T cell has been inactivated. In some embodiments, the providing includes obtaining T cells, inactivating the ITK gene in the obtained cells ex vivo, and transplanting the cells into the subject. In a specific embodiment, the T cell is autologous. In a specific embodiment, the T cell is non-autologous.

In some embodiments, the inactivation of the ITK gene in the T cell is achieved by deleting or mutating the ITK gene in whole or in part such that no functional ITK protein product is expressed. In some embodiments, the inactivation of the ITK gene in the T cell is achieved by a method selected from the group consisting of CRISPR/Cas system, Cre/Lox system, TALEN system and homologous recombination.

In some embodiments, the inactivation of the ITK genes in the T cell is achieved by blocking the signaling of ITK using an ITK inhibitor. In some embodiments, the ITK inhibitor is selected from the group consisting of a small molecule inhibitor, a nucleic acid inhibitor, and a peptide inhibitor. In a specific embodiment, the ITK inhibitor is a nucleic acid inhibitor selected from the group consisting of an antisense RNA, a small interfering RNA, an RNAi, a microRNA, an artificial microRNA, and a ribozyme.

In some embodiments, the ITK inhibitor is a peptide inhibitor including a sequence as shown in SEQ ID NO: 2, wherein the peptide inhibitor includes a phosphorylated tyrosine. In a specific embodiment, wherein the peptide inhibitor further comprises a TAT-peptide sequence such as (SEQ ID NO: 3). In a specific embodiment, wherein the peptide inhibitor further comprises tag. In some embodiments, the tag is a fluorescent tag.

Compositions

In embodiments, the instant disclosure is directed to compositions to inhibit the ITK protein or ITK signaling.

In some embodiments, the compositions of the disclosure include an ITK inhibitor. In some embodiments, the ITK inhibitor is selected from the group consisting of a small molecule inhibitor, a nucleic acid inhibitor, and a peptide inhibitor. In a specific embodiment, the ITK inhibitor is a nucleic acid inhibitor selected from the group consisting of an antisense RNA, a small interfering RNA, an RNAi, a microRNA, an artificial microRNA, and a ribozyme.

In some embodiments, the ITK inhibitor is a peptide inhibitor that includes a sequence as shown in SEQ ID NO: 2, and wherein the peptide inhibitor includes a phosphorylated tyrosine. In some embodiments, the ITK inhibitor is a peptide inhibitor that includes an amino acid sequence having at least 80%, 90%, 95%, 97% or 99% sequence identity to SEQ ID NO: 2, and wherein the peptide inhibitor includes a phosphorylated tyrosine. In a specific embodiment, wherein the peptide inhibitor further includes a TAT-peptide sequence (SEQ ID NO: 3). In a specific embodiment, wherein the peptide inhibitor further includes tag. In some embodiments, the tag is a fluorescent tag.

The inventors have found that inactivating or inhibiting the interleukin-2-inducible T-cell kinase (ITK) gene in T-cell significantly reduces production of inflammatory cytokines and migration of the T cells to graft-versus-host disease (GVHD) target organs, while retaining the therapeutic graft-versus-tumor effect of the T-cells intact. This disclosure is directed to methods and compositions for inactivating the ITK or the ITK gene in a subject in need of such treatment.

The Tec family nonreceptor tyrosine kinase, Interleukin-2-inducible T cell kinase (ITK), regulates activation of T cells downstream of the T cell receptor (TCR). ITK is involved in the activation of intracellular calcium signaling and MAPK pathways, as well as polarization of the actin cytoskeleton, supporting an integral role for ITK in T cell activation and function (See e.g., August, A., Sadra, A., Dupont, B. & Hanafusa, H. Src-induced activation of inducible T cell kinase (ITK) requires phosphatidylinositol 3-kinase activity and the Pleckstrin homology domain of inducible T cell kinase. *Proc Natl Acad Sci USA* 94, 11227-11232 (1997); and Qi, Q., Sahu, N. & August, A. Tec kinase Itk forms membrane clusters specifically in the vicinity of recruiting receptors. *J Biol Chem* 281, 38529-38534 (2006)). ITK is involved in signaling which leads to cytokine production by T cell populations, and also regulates the development of a distinct, innate-type cytokine-producing T cell population in the thymus (See e.g., Atherly, L. O. et al. The Tec family tyrosine kinases Itk and RIk regulate the development of conventional CD8+ T cells. *Immunity* 25, 79-91 (2006)), referred to as innate memory phenotype (IMP) T cells. These cells express significantly higher levels of CD122, CD44, and Eomes. Since the activation, expansion, cytokine production, and migration of alloreactive donor T cells to target organs are hallmarks of GVHD (See e.g., Henden, A. S. & Hill, G. R. Cytokines in Graft-versus-Host Disease. *J Immunol* 194, 4604-4612 (2015); and Lynch Kelly, D., Lyon, D. E., Ameringer, S. A. & Elswick, R. K. Symptoms, Cytokines, and Quality of Life in Patients Diagnosed with Chronic Graft-Versus-Host Disease Following Allogeneic Hematopoietic Stem Cell Transplantation. *Oncol Nurs Forum* 42, 265-275 (2015)), and ITK is involved in these T cell activities, the role of ITK in GVHD and GVL in an allo-HSCT model was investigated. Using a murine allo-HSCT model involving allotransplant of T cells from C57BI/6 mice or Itk−/− mice to BALB/c mice, GVHD and GVL caused by alloreactive T cells from wild-type (WT) or ITK-deficient donors was examined.

The inventors have found that $CD4^+$ and $CD8^+$ T cells transplanted from ITK-signaling-deficient mice induce significantly less GVHD while retaining GVL function, compared to T cells from WT mice. To examine whether this reduction of GVHD with maintained GVL was due to cells with an IMP phenotype, and to investigate whether this effect was cell-intrinsic or cell-extrinsic, a mouse model of allo HSCT was created. The data showed that IMP cell development does not contribute to the separation of GVHD from GVL. IMP T cells derived from WT-bone marrow exhibit GVL effects but also cause GVHD, while IMP T cells derived from $Itk^{-/-}$ bone marrow cells are able to clear the leukemia cells without inducing GVHD. Furthermore, T cells from IL-4 receptor-alpha and ITK-double knockout mice (Itk/Il4ra DKO), which lack the IMP phenotype, did not induce GVHD, indicating that absence of ITK, and not IMP cells, is responsible for reduced GVHD in the absence of ITK. Both $CD8^+$ and $CD4^+$ T cells donor T cells from $Itk^{-/-}$ mice also exhibit increased expression of perforin and significantly reduced expression of pro-inflammatory cytokines. $Itk^{-/-}$ donor T cells also exhibit reduced proliferation, which was cell-extrinsic.

The data also show that both $CD4^+$ and $CD8^+$ T cells from $Itk^{-/-}$ mice upregulate the key transcription factor Eomesodermin (Eomes), while causing minimal GVHD and retaining GVL function. Eomes is critical for this functions since $Itk^{-/-}$ $Eomes^{flox/flox}$ $CD4cre^+$ T cell donors (deficient in both Eomes and ITK) did not mount a cytotoxic response against primary leukemia cells or clear tumor cells, both in vitro and in vivo.

The data further demonstrate that ITK deficiency affects JAK1/2[13] and IRF-4[14] signaling. $CD4^+$ and $CD8^+$ T cells from ITK-deficient mice show defects in T cell migration into GVHD target tissues, caused by reduced expression of chemokine receptors. This leads to decreased tissue damage during allo-HSCT. $Itk^{-/-}$ T cells can successfully clear leukemia cells in circulation, however they are unable to clear subcutaneously growing leukemic cells due to this migration defect. Finally, RNA sequencing data revealed that ITK deficiency impacts genes involved in cytokine production, cell adhesion, and chemokine and cytokine receptor expression. These genes are involved in the pathogenesis of GVHD. The studies identified a specific and novel potential therapeutic target and its downstream mechanism for separating GVHD and GVL after allo-HSCT. Targeting ITK may also prove beneficial for other T cell-mediated diseases.

Definitions

As used in the present specification, the following words and phrases are generally intended to have the meanings as set forth below, except to the extent that the context in which they are used indicates otherwise.

As used herein, the singular forms “a”, “an”, and “the” include plural references unless the context clearly dictates otherwise. Thus, for example, references to “a compound” include the use of one or more compound(s). “A step” of a method means at least one step, and it could be one, two, three, four, five or even more method steps.

The term “about”, as used herein, refers to +/−10% of the stated value or a chemical or obvious equivalent thereof.

cDNA: The term “cDNA” means a DNA molecule that can be prepared by reverse transcription from a mature, spliced, mRNA molecule obtained from a eukaryotic or prokaryotic cell. cDNA lacks introns or intron sequences that may be present in corresponding genomic DNA. In embodiments, cDNA may refer to a nucleotide sequence that correspond to the nucleotide sequence of an mRNA from which it is derived.

Coding sequence: The term “coding sequence” means a polynucleotide, which directly specifies the amino acid sequence of a polypeptide. The boundaries of the coding sequence are generally determined by an open reading frame, which begins with a start codon and ends with a stop codon. The coding sequence may be a genomic DNA, cDNA, synthetic DNA, or a combination thereof.

As used herein the term “fragment” means a polypeptide having one or more amino acids absent from the amino and/or carboxyl terminus of a mature polypeptide or domain. In embodiments, a fragment contains at least 1% to 75%, at least 2% to 40% or about 2 to 30% of the number of amino acids of the mature polypeptide of SEQ ID NO: 4.

The term “mature polypeptide” means a polypeptide in its final form following translation and any post-translational modifications.

The terms “polynucleotide” and “nucleic acid,” used interchangeably herein, refer to a polymeric form of nucleotides of any length, either ribonucleotides or deoxyribonucleotides. Thus, terms “polynucleotide” and “nucleic acid” encompass single-stranded DNA; double-stranded DNA; multi-stranded DNA; single-stranded RNA; double-stranded RNA; multi-stranded RNA; genomic DNA; cDNA; DNA-RNA hybrids; and a polymer including purine and pyrimidine bases or other natural, chemically or biochemically modified, non-natural, or derivatized nucleotide bases. The terms "polynucleotide" and "nucleic acid" should be understood to include, as applicable to the embodiments being described, single-stranded (such as sense or antisense) and double-stranded polynucleotides.

The term "complementary" refers to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G), or in any other manner that allows for the formation of stable duplexes. Complementarity is typically measured with respect to a duplex region and thus excludes, for example, overhangs. A duplex region may include a region of complementarity between two strands or between two regions of a single strand, for example, a unimolecular siRNA. Typically, the region of complementarity results from Watson-Crick base pairing. In embodiments, perfect complementarity or 100% complementarity refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other. For example, for two 20-mers, if only two base pairs on each strand can hydrogen bond with each other, the polynucleotide strands or regions exhibit 10% complementarity. In the same example, if 18 base pairs on each strand or each region can hydrogen bond with each other, the polynucleotide strands exhibit 90% complementarity. Substantial complementarity refers to polynucleotide strands or regions exhibiting 80% or greater complementarity.

By "hybridizable" or "complementary" or "substantially complementary" a nucleic acid (e.g. RNA, DNA) includes a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine/adenosine) (A) pairing with thymidine/thymidine (T), A pairing with uracil/uridine (U), and guanine/guanosine) (G) pairing with cytosine/cytidine (C). In addition, for hybridization between two RNA molecules (e.g., dsRNA), and for hybridization of a DNA molecule with an RNA molecule (e.g., when a DNA target nucleic acid base pairs with a guide RNA, etc.): G can also base pair with U. For example, G/U base-pairing is partially responsible for the degeneracy (i.e., redundancy) of the genetic code in the context of tRNA anti-codon base-pairing with codons in mRNA. Thus, in the context of this disclosure, a G (e.g., of a protein-binding segment (e.g., dsRNA duplex) of a guide RNA molecule; of a target nucleic acid (e.g., target DNA) base pairing with a guide RNA) is considered complementary to both a U and to C. For example, when a G/U base-pair can be made at a given nucleotide position of a protein-binding segment (e.g., dsRNA duplex) of a guide RNA molecule, the position is not considered to be non-complementary, but is instead considered to be complementary.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more).

It is understood that the sequence of a polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure, a 'bulge', and the like). A polynucleotide can include 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. The remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

As used herein the "degree of identity" refers to the relatedness between two amino acid sequences or between two nucleotide sequences and is described by the parameter "identity". In embodiments, the degree of sequence identity between a query sequence and a reference sequence is determined by: 1) aligning the two sequences by any suitable alignment program using the default scoring matrix and default gap penalty; 2) identifying the number of exact matches, where an exact match is where the alignment program has identified an identical amino acid or nucleotide in the two aligned sequences on a given position in the alignment; and 3) dividing the number of exact matches with the length of the reference sequence. In one embodiment, the degree of sequence identity between a query sequence and a reference sequence is determined by: 1) aligning the two sequences by any suitable alignment program using the default scoring matrix and default gap penalty; 2) identifying the number of exact matches, where an exact match is where the alignment program has identified an identical amino acid; or nucleotide in the two aligned sequences on a given position in the alignment; and 3) dividing the number of exact matches with the length of the longest of the two sequences. In some embodiments, the degree of sequence identity refers to and may be calculated as described under "Degree of Identity" in U.S. Pat. No. 10,531,672 starting at Column 11, line 56. U.S. Pat. No. 10,531,672 is incorporated by reference in its entirety.

In embodiments, an alignment program suitable for calculating percent identity performs a global alignment program, which optimizes the alignment over the full-length of the sequences. In embodiments, the global alignment program is based on the Needleman-Wunsch algorithm (Needleman, Saul B.; and Wunsch, Christian D. (1970), "*A general method applicable to the search for similarities in the amino acid sequence of two proteins*", Journal of Molecular Biology 48 (3): 443-53). Examples of current programs performing global alignments using the Needleman-Wunsch algorithm are EMBOSS Needle and EMBOSS Stretcher programs, which are both available on the world wide web at www.ebi.ac.uk/Tools/psa/. In some embodiments a global alignment program uses the Needleman-Wunsch algorithm and the sequence identity is calculated by identifying the number of exact matches identified by the program divided by the "alignment length", where the alignment length is the length of the entire alignment including gaps and overhanging parts of the sequences.

The term "deoxynucleotide" refers to a nucleotide or polynucleotide lacking an OH group at the 2' or 3' position of a sugar moiety, and/or a 2',3' terminal dideoxy, but instead having a hydrogen at the 2' and/or 3' carbon.

The terms "deoxyribonucleotide" and "DNA" refer to a nucleotide or polynucleotide including at least one ribosyl moiety that has an H at the 2' position of a ribosyl moiety. In embodiments, a deoxyribonucleotide is a nucleotide having an H at its 2' position.

The term "isolated" means a substance in a form or environment that does not occur in nature.

The term "nucleotide" refers to a ribonucleotide or a deoxyribonucleotide or modified form thereof, as well as an analog thereof. Nucleotides include species that include purines, e.g., adenine, hypoxanthine, guanine, and their derivatives and analogs, as well as pyrimidines, e.g., cytosine, uracil, thymine, and their derivatives and analogs. In embodiments, a "nucleotide" includes a cytosine, uracil, thymine, adenine, or guanine moiety. In embodiments, nucleotides, unless otherwise specified (such as, for example, when specifying a 2' modification, 5' modification, 3' modification, nucleobase modification, or modified internucleotide linkage), include unmodified cytosine, uracil, thymine, adenine, and guanine. In embodiments, nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety as defined herein.

As used herein, the terms "isolated nucleic acid fragment", and "isolated nucleic acid molecule" are used interchangeably and are optionally single-stranded or double-stranded with synthetic, non-natural or modified nucleotide bases. This will indicate a single-stranded RNA or DNA polymer.

As used herein, the term "nucleic acid molecule" refers to any molecule containing multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)). As described further below, bases include C, T, U, C, and G, as well as variants thereof. As used herein, the term refers to ribonucleotides (including oligoribonucleotides (ORN)) as well as deoxyribonucleotides (including oligodeoxynucleotides (ODN)). The term shall also include polynucleosides (i.e., a polynucleotide minus the phosphate) and any other organic base containing polymer. Nucleic acid molecules can be obtained from existing nucleic acid sources (e.g., genomic or cDNA), but include synthetic (e.g., produced by oligonucleotide synthesis). In embodiments, the terms "nucleic acid" "nucleic acid molecule" and "polynucleotide" may be used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" includes a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before embodiments are further described, it is to be understood that this disclosure is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

DETAILED DESCRIPTION OF CERTAIN EMBODIMENTS

In embodiments, the present disclosure includes compositions and methods for the treatment, amelioration, prevention or suppression of cancers, malignancies, blood malignancies, and/or immunological deficiencies for subjects in need thereof. In embodiments, the present disclosure provides methods and compositions for the treatment, amelioration, prevention or suppression of disease such as where a subject suffers from cancer, diabetes, or graft-versus-host disease.

In embodiments, the present disclosure includes one or more inhibitors of "Inducible T Cell Kinase" (ITK) polypeptides and methods of making and using them, e.g., as agents and pharmaceutical compositions to treat cancer, diabetes, or graft-versus-host disease, or other pathologic responses. In embodiments, the present disclosure is directed to ITK protein expression and/or activity inhibitors. In one aspect, the ITK protein inhibitors of the disclosure are used to treat cancer, diabetes, or graft-versus-host disease, or other pathologic responses. In embodiments the present disclosure is directed to ITK protein inhibitors as chimeric proteins including fragments or altered or truncated forms of mammalian or human SLP76 protein (SEQ ID NO:4) or equivalent. In other aspects SLP76 protein, or fragments thereof are joined or fused to another moiety (e.g., a dye or TAT sequence). The present disclosure also provides pharmaceutical compositions including the ITK protein inhibitors of the disclosure, and methods of making and using them, including methods for ameliorating or preventing cancer, diabetes, or graft-versus-host disease or other pathologic responses. The disclosure also provides compositions for transfecting cells with nucleic acids acting as ITK protein inhibitors and/or the chimeric ITK protein inhibitors polypeptides of the present disclosure.

In embodiments, the present disclosure includes methods and compositions for transfecting nucleic acids into a cell including an ITK protein inhibitor of the present disclosure. In one aspect, the ITK protein inhibitor of the present disclosure includes a nucleic acid including naked DNA or RNA, and optionally the naked DNA or RNA, or RNAi such as siRNA or miRNA, is operably linked to a promoter. In one aspect, the nucleic acid includes plasmid DNA, a recombinant virus or phage, an expression cassette or a vector such as an expression vector. In one aspect, the cell is a mammalian cell, wherein optionally the mammalian cell is a human cell such as a human T cell, or alloreactive donor T cells suitable for use in allogeneic hematopoietic stem cell transplantation (allo-HSCT).

In embodiments, the present disclosure includes methods for transfecting a cell with nucleic acid of the present disclosure including the following steps: (a) providing a nucleic acid-including composition of the present disclosure (for transfecting nucleic acids); (b) contacting the cell with the composition of step (a) under conditions wherein the composition is internalized into the cell. In embodiments, the transfecting is an in vivo transfection or an in vitro transfection.

In embodiments, the present disclosure includes methods for preventing, inhibiting, suppressing or ameliorating cancer, diabetes, or graft-versus-host disease or other pathologic responses by inhibiting the activation of T-helper cells responsible for the graft-versus-host disease while maintaining a graft-versus tumor effect, the method including, a peptide conjugate that is able to efficiently gain entry into T-helper cell and inhibit the activation of ITK and SLP-76, leading to inhibition of T-helper cell responsible graft-versus-host disease. In embodiments, the cell is a T cell or any T cell suitable for use in hematopoietic stem cell transplantation such as allogeneic hematopoietic stem cell transplantation (allo-HSCT).

In embodiments, a suitable peptide of the present disclosure includes the peptide of SEQ ID NO 2. In embodiments, a suitable peptide such as a peptide inhibitor of the present disclosure includes the peptide having an amino acid sequence having at least 80%, 90%, 95%, 97%, or 99% sequence identity to SEQ ID NO 2, wherein the peptide inhibitor includes a phosphorylated tyrosine. In embodiments, the present disclosure provides isolated, synthetic or recombinant polypeptides or peptides including or consisting of SEQ ID NO: 2, wherein the peptide inhibitor includes a phosphorylated tyrosine. In embodiments, a suitable peptide of the present disclosure disrupts SLP76: ITK interactions, leading to reduced inflammatory cytokine production and reduced chemokine receptor upregulation.

In some embodiments, the present disclosure relates to a complementary deoxynucleotide (cDNA) sequence encoding an amino acid sequence having at least 90%, at least 95%, or at least 99% sequence identity to SEQ ID NO: 2. In some embodiments, the present disclosure relates to a complementary deoxynucleotide (cDNA) sequence encoding the amino acid sequence of SEQ ID NO: 2. In embodiments, the cDNA are made through laboratory manipulation and genetic engineering techniques. In embodiments, methods of making synthetic polypeptides of the present disclosure are known in the art. In some embodiments, a suitable cDNA sequence of the present disclosure includes the nucleic acid sequence of SEQ ID NO: 1. In embodiments, SEQ ID NO: 1 encodes SEQ ID NO: 2. In embodiments, the nucleic acid sequence of SEQ ID NO: 1 may include conservative substitutions, wherein alterations such as substitutions may be present and the nucleotide encodes SEQ ID NO: 2.

In embodiments, the polypeptides and peptides of the present disclosure have increased intracellular penetration and delivery because of several added moieties. In some embodiments, the polypeptides and peptides of the present disclosure may include a peptide conjugate including a subsequence of SLP76 that binds to ITK. In one aspect, the polypeptides and peptides of the present disclosure are able to efficiently penetrate and enter T cells such as CD4 positive T cells.

Pharmaceutical Compositions

The present disclosure provides pharmaceutical compositions including an ITK-inhibitory nucleic acid or peptide or polypeptide of the present disclosure and a pharmaceutically acceptable excipient. The present disclosure provides for uses of an ITK-inhibitory nucleic acid or peptide or polypeptide of the disclosure to make a pharmaceutical composition. The present disclosure provides parenteral formulations including an ITK-inhibitory nucleic acid or polypeptide of the present disclosure. The present disclosure provides enteral formulations including an ITK-inhibitory nucleic acid or polypeptide of the present disclosure. The present disclosure provides methods for treating GVHD including providing a pharmaceutical composition including an ITK-inhibitory nucleic acid or polypeptide of the present disclosure; and administering an effective amount of the pharmaceutical composition to a subject in need thereof.

The pharmaceutical compositions used in the methods of the present disclosure can be administered by any means known in the art, e.g., parenterally, topically, orally, or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Pharmaceutical formulations of the present disclosure can be prepared according to any method known to the art for the manufacture of pharmaceuticals. Such drugs can contain sweetening agents, flavoring agents, coloring agents and preserving agents. A formulation of the invention can be admixtured with nontoxic pharmaceutically acceptable excipients which are suitable for manufacture. Formulations of the disclosure may include one or more diluents, emulsifiers, preservatives, buffers, excipients, etc, and may be provided in such forms as liquids, powders, emulsions, lyophilized powders, sprays, creams, lotions, controlled release formulations, tablets, pills, gels, on patches, in implants, etc, or formulated for inhalers, nebulizers, which are devices used to administer medication to people in forms of a liquid mist to the airways, or atomizers. A vaporized medicine can be inhaled through a tube-like mouthpiece, e.g., an inhaler, nebulizer or atomizer; this can have a benefit of allowing surrounding air to mix with the formulation, decreasing the unpleasantness of the vapor, if any.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Single or multiple administrations of formulations can be given depending on the dosage and frequency as required and tolerated by the patient. The formulations should provide a sufficient quantity of active agent to effectively treat the treat (e.g., ameliorate) or prevent disease and/or its symptoms of GVHD. The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

In embodiments, the present disclosure relates to a a method including administering a subject in need thereof an effective amount of an inhibitor of interleukin-2-inducible T-cell kinase (ITK). In embodiments, the subject suffers from cancer, diabetes, or graft-versus-host disease. In embodiments, the ITK inhibitor is selected from the group consisting of a small molecule inhibitor, a nucleic acid inhibitor, and a peptide inhibitor. In embodiments, the nucleic acid inhibitor is selected from the group consisting of an antisense RNA, a small interfering RNA, an RNAi, a microRNA, an artificial microRNA, and a ribozyme. In embodiments, the peptide inhibitor includes a sequence as shown in SEQ ID NO: 2, and wherein the peptide inhibitor includes a phosphorylated tyrosine. In embodiments, the peptide inhibitor further includes a TAT-peptide sequence. In embodiments, the ITK inhibitor is administered intermittently. In embodiments, the ITK inhibitor is administered every other day, every three days, every five days or once a week. In embodiments, the ITK inhibitor is administered every hour, every two hours, every three hours, every six hours or every twelve hours. In embodiments, the ITK inhibitor is administered by intravenous (i.v.) injection, intraperitoneal (i.p.) injection, subcutaneous (s.c.) injection, or aerosolized delivery. In embodiments, the effective amount of the ITK inhibitor is between 0.2 mg/kg and 20 mg/kg.

In some embodiments, the present disclosure relates to a method including providing a T cell to a subject, wherein the interleukin-2-inducible T-cell kinase (ITK) gene in the T cell has been inactivated. In some embodiments, providing includes obtaining T cells, inactivating the ITK gene in the obtained cells ex vivo, and transplanting the cells into the subject. In some embodiments, providing includes inactivating the ITK gene in insulin-producing cells in the subject in vivo. In some embodiments, the inactivation of the ITK gene in the T cell is achieved by deleting or mutating the ITK gene in whole or in part such that no functional ITK protein product is expressed. In some embodiments, the inactivation of the ITK gene in the T cell is achieved by a method selected from the group consisting of CRISPR/Cas system, Cre/Lox system, TALEN system and homologous recombination. In some embodiments, the inactivation of the ITK genes in the T cell is achieved by blocking the signaling of ITK using an ITK inhibitor. In some embodiments, the ITK inhibitor is selected from a small molecule inhibitor, a nucleic acid inhibitor, and a peptide inhibitor. In some embodiments, the nucleic acid inhibitor is selected from the group consisting of an antisense RNA, a small interfering RNA, an RNAi, a microRNA, an artificial microRNA, and a ribozyme. In some embodiments, the peptide inhibitor comprises a sequence as shown in SEQ ID NO: 2, and wherein the peptide inhibitor comprises a phosphorylated tyrosine. In some embodiments, the peptide inhibitor comprises an amino acid sequence having at least 80%, 90%, 95%, 97%, or 99% sequence identity to SEQ ID NO: 2 and wherein the peptide inhibitor includes a phosphorylated tyrosine. In embodiments, the peptide inhibitor further includes a TAT-peptide sequence.

In embodiments, the present disclosure includes a composition including an inhibitor of interleukin-2-inducible T-cell kinase (ITK) selected from a small molecule inhibitor, a nucleic acid inhibitor, and a peptide inhibitor. In some embodiments, the nucleic acid inhibitor is selected from the group consisting of an antisense RNA, a small interfering RNA, an RNAi, a microRNA, an artificial microRNA, and a ribozyme. In some embodiments. In embodiments, the peptide inhibitor includes a sequence as shown in SEQ ID NO: 2, and wherein the peptide inhibitor includes a phosphorylated tyrosine. In embodiments, the peptide inhibitor further includes a TAT-peptide sequence. In embodiments the present disclosure includes a nucleic acid encoding a peptide inhibitor of the present disclosure. In embodiments, the present disclosure includes a vector including a nucleic acid according to the present disclosure. In embodiments, the present disclosure relates to one or more T-cells including a nucleic acid encoding a polypeptide of the present disclosure, or the T-cells include a polypeptide having at least 90%, at least 95%, at least 99% sequence identity to SEQ ID NO: 2, wherein the peptide inhibitor includes a phosphorylated tyrosine.

Example I

Materials and Methods

Mice: $Itk^{-/-}$ mice were described previously (See e.g., Liao X C, Littman D R. Altered T cell receptor signaling and disrupted T cell development in mice lacking Itk. Immunity (1995) 3:757-69. doi: 10.1016).1074-7613 (95) 90065-9). C57BL/6, C57BL/6.SJL (B6-SJL), ROSA26-pCAGGs-LSL-Luciferase, Thy1.1 (B6.PL-Thy1a/CyJ), CD45.1 (B6.SJL-$Ptprc^{a}$ $Pepc^{b}$/BoyJ) and BALB/c mice were purchased from Charles River or Jackson Laboratory. $Eomes^{flox/flox}$ mice, B6.129S1 mice, and CD4cre mice were purchased from Jackson Laboratory. Mice expressing Cre driven by the CMV promoter (CMV-Cre) were purchased from the Jackson Laboratory and crossed to ROSA26-pCAGGs-LSL-Luciferase mice (B6-luc). B6-luc mice were bred with $Itk^{-/-}$ mice to create $Itk^{-/-}$ luc mice. $Itk^{-/-}$ and $Il4ra^{-/-}$ double knockout mice have been described (See e.g., Huang W, et al., ITK tunes IL-4-induced development of innate memory CD8+ T cells in a gammadelta T and invariant NKT cell-independent manner. J Leukoc Biol (2014) 96:55-63. doi: 10.1189/jlb.1AB0913-484RR).

Mice aged 8-12 weeks were used, and all experiments were performed with age and sex-matched mice. Animal maintenance and experimentation were performed in accordance with the rules and guidance set by the institutional animal care and use committees at SUNY Upstate Medical University and Cornell University.

Reagents, cell lines, flow cytometry: Monoclonal antibodies were purchased from eBiosciences (San Diego, CA) or BD Biosciences (San Diego, CA). Antibodies used included anti-CD3, anti-CD28, anti-CD3-FITC, Anti-CD3-BV605, anti-CD8-FITC, anti-BrdU-APC, anti-IFNγ-APC, anti-TNFα-PE, anti-CD45.1-PerCPCy5.5, anti-CD122-APC, anti-CD44-Pacific blue, anti-Eomes-PE-Cy7, anti-CD25-BV421, anti-FoxP3-APC, anti-T-bet-BV421, anti-CD4-BV785, anti-CD45.1-Pacific Blue, anti-H-$2K^{d}$-Pacific Blue. Multiplex ELISAs were performed using Biolegend LEGENDplex kits, and some kits were custom ordered to detect both mouse and human cytokines. Luciferin was purchased from Perkin Elmer (Waltham, MA) and Gold Bio (St Louis MO). Dead cells were excluded from analysis with LIVE/DEAD Fixable Aqua Dead Cell staining. Flow cytometry was performed using a BD LSR-II or BD LSRFortessa cytometer (BD Biosciences). Data were analyzed with FlowJo software (Tree Star, Ashland, OR).

For cell sorting, T cells were purified with either anti-CD8 or anti-CD4 magnetic beads using MACS columns (Miltenyi Biotec, Auburn, CA) prior to cell surface staining. FACS sorting was performed with a FACS Aria III cell sorter (BD Biosciences). FACS-sorted populations were typically of >95% purity. Antibodies against IRF4, STAT3, JAK2, JAK1, GAPDH, and β-Actin (for total and/or phospho proteins) were purchased from Cell Signaling Technology (Danvers, MA). All cell culture reagents and chemicals were purchased from Invitrogen (Grand Island, NY) and Sigma-Aldrich (St. Louis, MO), unless otherwise specified. The A20 cell lines (American Type Culture Collection; Manassas, VA), and primary mouse B-ALL blast cells (See e.g., Cheng Y, et al. LNK/SH2B3 regulates IL-7 receptor signaling in normal and malignant B-progenitors. J Clin Invest (2016) 126:1267-81. doi: 10.1172/JCI81468) were transduced with luciferase, and cultured as described previously (See e.g., Edinger M, et al. CD4+CD25+ regulatory T cells preserve graft-versus-tumor activity while inhibiting graft-versus-host disease after bone marrow transplantation. Nat Med (2003) 9:1144-50. doi: 10.1038/nm915).

Allo-HSCT and GVL studies: Lethally irradiated BALB/c mice (800 cGy) were injected intravenously with $10\times10^6$ T cell-depleted bone marrow ($_{TCD}$BM) cells with or without $1\times10^6$ FACS-sorted $CD8^+$ T cells, $1\times10^6$ $CD4^+$ T cells, or CD8/CD4 cells mixed at a 1:1 ratio. FACS-sorted total $CD8^+$, total $CD4^+$, or mixed donor $CD4^+$ and $CD8^+$ T cells from WT (C57Bl/6) or $Itk^{-/-}$ mice were used. For GVL experiments, B-cell acute lymphoblastic leukemia (B-ALL) primary blasts (See e.g., Cheng Y, et al. LNK/SH2B3 regulates IL-7 receptor signaling in normal and malignant B-progenitors. J Clin Invest (2016) 126:1267-81. doi: 10.1172/JCI81468) transduced with luciferase were cultured as described previously (Edinger M, et al. CD4+CD25+ regulatory T cells preserve graft-versus-tumor activity while inhibiting graft-versus-host disease after bone marrow transplantation. Nat Med (2003) 9:1144-50. doi: 10.1038/nm915), and $2\times10^5$ luciferase-expressing B-ALL blasts were used. Mice were evaluated twice a week from the time of leukemia cell injection for 65 days by bioluminescence imaging using the IVIS 50 Imaging System (Xenogen) as previously described (See e.g, Contag C H, et al., Advances in in vivo bioluminescence imaging of gene expression. Annu Rev Biomed Eng (2002) 4:235-60. doi: 10.1146/annurev.bioeng.4.111901.093336). Clinical presentation of the mice was assessed 2-3 times per week by a scoring system that sums changes in 5 clinical parameters: weight loss, posture, activity, fur texture, and skin integrity (See e.g., Cooke K R, et al. An experimental model of idiopathic pneumonia syndrome after bone marrow transplantation: I. The roles of minor H antigens and endotoxin. Blood (1996) 88:3230-9. doi: 10.1182/blood.V88.8.3230.blood-journal8883230). Mice were euthanized when they lost ≥30% of their initial body weight or became moribund.

For chimera experiments, bone marrow cells from $Itk^{-/-}$ ($CD45.1^+$) or C57Bl/6 ($CD45.2^+$) mice were mixed at different ratios-1:1 (WT:$Itk^{-/-}$), 1:2, 1:3, or 1:4 —and transplanted into lethally irradiated Thy1.1 mice. In some experiments, $Itk^{-/-}$ was used on a CD45.2 background and WT on a CD45.1 background as indicated in the figure legends. Mice were bled from the tail vein after 9 weeks to determine the presence of $Itk^{-/-}$ and WT cells. For GVHD assessment experiments, $Itk^{-/-}$ ($CD45.1^+$) and WT (CD45.2) T cells were FACS-sorted from Thy1.1 hosts and then transplanted to irradiated BALB/c mice carrying leukemia cells, along with T cell-depleted bone marrow as described above. This was followed by analysis of GVHD and GVL. In some experiments FACS-sorted $CD8^+$ T cells from WT or $Itk^{-/-}$ mice were mixed at a 1:1 ratio and injected into BALB/c mice ($2\times10^6$ $CD8^+$ T cells total).

Tissues Imaging: Allo-HSCT was performed with $10\times10^6$ WT T cell-depleted BM cells and $1\times10^6$ FACS-sorted $CD8^+$ or $1\times10^6$ FACS-sorted $CD4^+$ T cells (from B6-luc or $Itk^{-/-}$ luc mice) and bioluminescence imaging of tissues was performed as previously described (See e.g., Beilhack A, et al. In vivo analyses of early events in acute graft-versus-host disease reveal sequential infiltration of T-cell subsets. Blood (2005) 106:1113-22. doi: 10.1182/blood-2005-02-0509). Briefly, 5 minutes after injection with luciferin (10 μg/g body weight), selected tissues were prepared and imaged for 5 minutes. Imaging data were analyzed and quantified with Living Image Software (Xenogen) and Igor Pro (Wave Metrics, Lake Oswego, OR).

Cytokine production, cytotoxicity, and BrdU incorporation assays: On Day 7 post-transplantation, serum and single cell suspensions of spleens were obtained. Serum IL-33, IL-1α, IFN-γ, TNF-α and IL-17A content was determined by multiplex cytokine assays (Biolegend LEGENDplex). T cells were stimulated with anti-CD3/anti-CD28 for 4-6 hours in the presence of brefeldin A (10 μM) and stained intracellularly for cytokines (IFN-γ and TNF-α). Control cells were stimulated with PMA and ionomycin in the presence of brefeldin A (Cat #00-4506-51).

Proliferation Assays: For detection of BrdU, mice were given BrdU with an initial bolus of BrdU (2 mg per 200 μl intraperitoneally) and drinking water containing BrdU (1 mg/ml) for 2 days. BrDU incorporation was performed using BrDU kit (Invitrogen 8846-6600-42) according to the manufacturer's instructions.

Cytotoxicity assays: For cytotoxicity assays, luciferase-expressing A20 cells were seeded in 96-well flat bottom plates at a concentration of $3\times10^5$ cells/ml. D-firefly luciferin potassium salt (75 μg/ml; Caliper Hopkinton, MA) was added to each well and bioluminescence was measured with the IVIS 50 Imaging System. Subsequently, ex vivo effector cells (MACS-sorted or FACS-sorted $CD8^+$ T cells from bone marrow-transplanted mice) were added at 40:1, 10:1, and 5:1 effector-to-target (E:T) ratios and incubated at 37° C. for 4 hours. Bioluminescence in relative luciferase units (RLU) was then measured for 1 minute. Cells treated with 1% Nonidet P-40 was used as a measure of maximal killing. Target cells incubated without effector cells were used to measure spontaneous death. Triplicate wells were averaged and percent lysis was calculated from the data using the following equation: % specific lysis=100×(spontaneous death RLU−test RLU)/(spontaneous death RLU−maximal killing RLU) (See e.g., Karimi M A, et al. Measuring cytotoxicity by bioluminescence imaging outperforms the standard chromium-51 release assay. PloS One (2014) 9: e89357. doi: 10.1371/journal.pone.0089357).

Migration assays: Lethally irradiated BALB/c mice were injected intravenously with $10\times10^6$ WT T cell-depleted bone marrow (TCDBM) cells from B6.PL-$Thy1^a$/CyJ mice, along with FACS-sorted $CD8^+$ or $CD4^+$ T cells from B6.SJL and $Itk^{-/-}$ mice, mixed at a 1:1 (WT:$Itk^{-/-}$) ratio. Seven days post-transplantation, the mice were sacrificed and lymphocytes from the liver, small intestine, spleen, and skin-draining lymph nodes were isolated. Livers were perfused with PBS, dissociated, and filtered with a 70 μm filter. The small intestines were washed in media, shaken in strip buffer at 37° C. for 30 minutes to remove the epithelial cells, and then washed, before digesting with collagenase D (100 mg/ml) and DNase (1 mg/ml) for 30 minutes in 37° C., and followed by filtering with a 70 μm filter. Lymphocytes from the liver and intestines were further enriched using a 40% Percoll gradient. The cells were analyzed for $H2K^b$, $CD45.1^+$ and $CD45.2^+$ $CD8^+$ T cells by flow cytometry, but any bone marrow-derived T cells ($Thy1.1^+$) were excluded.

RNA sequencing: T cells from WT C57Bl/6 or $Itk^{-/-}$ mice were MACS purified and FACS sorted, and $2\times10^6$ FACS sorted $CD8^+$ T cells were transplanted into BALB/c mice, along with $_{TCD}$BM as described above. Seven days post transplantation, donor cells were purified from spleen (Spl). Samples were submitted to SUNY Upstate Medical University Sequencing core facility for RNA sequencing. Sort enough donor T cells from small intestine of the recipient mice that received $Itk^{-/-}$ T cells was problematic. Therefore, RNA sequencing data was generated from five groups: WT-Pre and $Itk^{-/-}$ Pre cells prior to transplantation; WT-Spleen, and $Itk^{-/-}$ Spleen using cells isolated from 7 days post-transplantation. Copy numbers were further analyzed in Gene Spring for normalization, quality control, correlation, principal component analysis and gene differential expression. The sequencing data is deposited in www.ncbi.nml.nih.gov/geo/Accession Display GSE161160.

Western blotting: Cells were lysed in freshly prepared lysis buffer using RIPA buffer from Fisher Scientific (cat #PI89900) and Complete Protease Inhibitor Cocktail (cat #11697498001) and centrifuged for 10 minutes at 4° C. Aliquots containing 70 μg protein were separated on a 12-18% denaturing polyacrylamide gel and transferred to nitrocellulose membranes for immunoblot analysis using specific Abs.

qPCR assay: To confirm the differences observed in RNA sequencing, pre- and post-transplanted donor T cells were FACS sorted from recipient mice on $H2K^b$ markers, and total RNA was isolated from T cells using the RNeasy kit from Qiagen (Germantown, MD). cDNA was made from total RNA using a cDNA synthesis kit (Invitrogen). qRT-PCR assay was performed with a premade customized plate (Fisher Scientific, Hampton, NH).

Human Patient Samples: Plasma was isolated from GVHD patients and healthy donors and performed cytokine ELISAs on these plasma samples using multiplex ELISA kits (Biolegend, San Diego, CA). This work was done under approved IRB protocol 1522145-2.

Statistics. All numerical data are reported as means with standard deviation. Data were analyzed for significance with GraphPad Prism. Differences were determined using one-way or two-way ANOVA and Tukey's multiple comparisons tests, or with a student's t-test when necessary. P-values less than or equal to 0.05 are considered significant. All transplant experiments are done with N=5 mice per group, and repeated at least twice, according to power analyses. Mice are sex-matched, and age-matched as closely as possible.

Results

Ablation of ITK Retains GVL Effect but Avoids GVHD During Allo-HSCT.

Figures 1B, 1C, 1D, 1E:
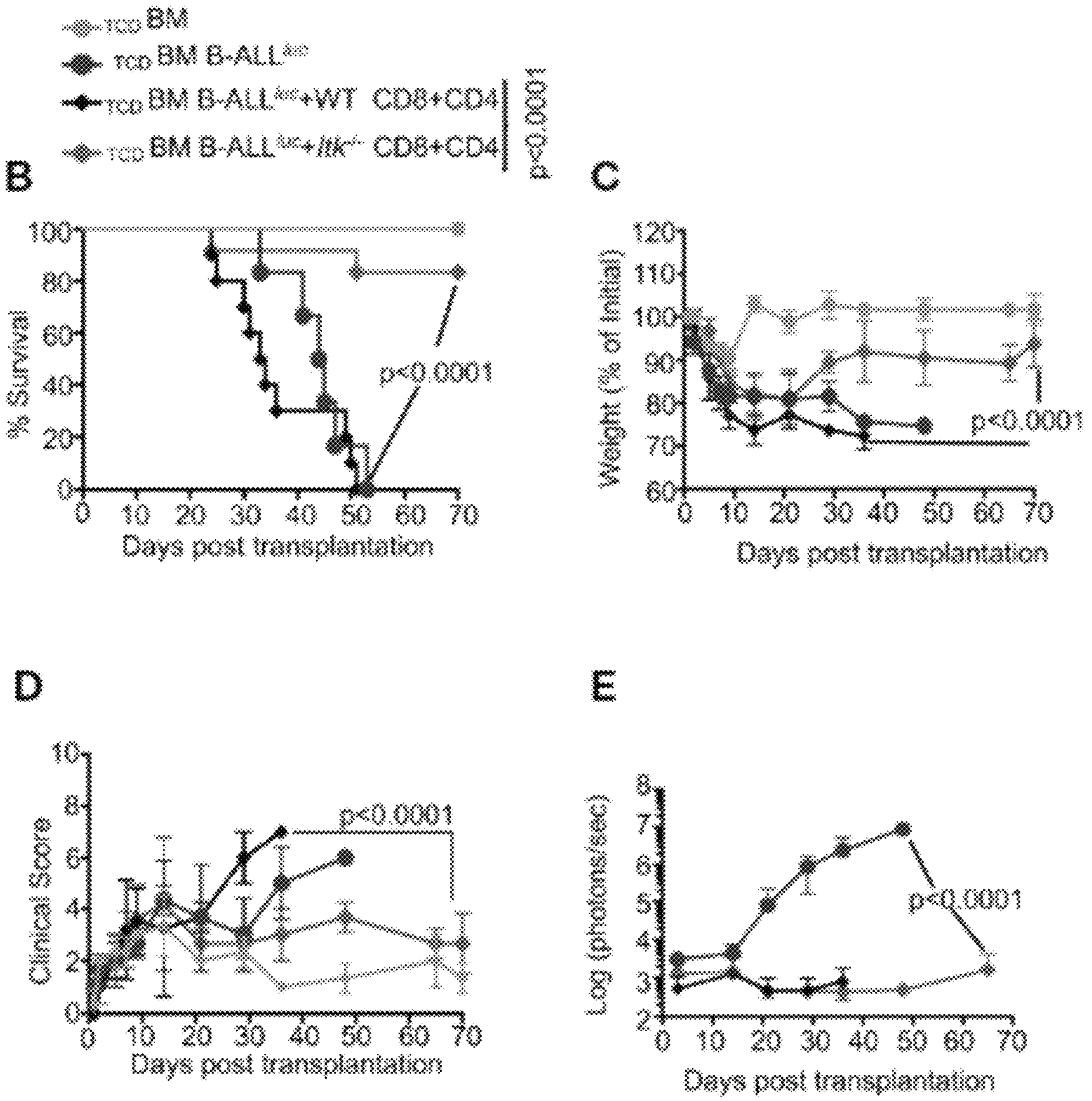
Figures 7A, 7B, 7C:
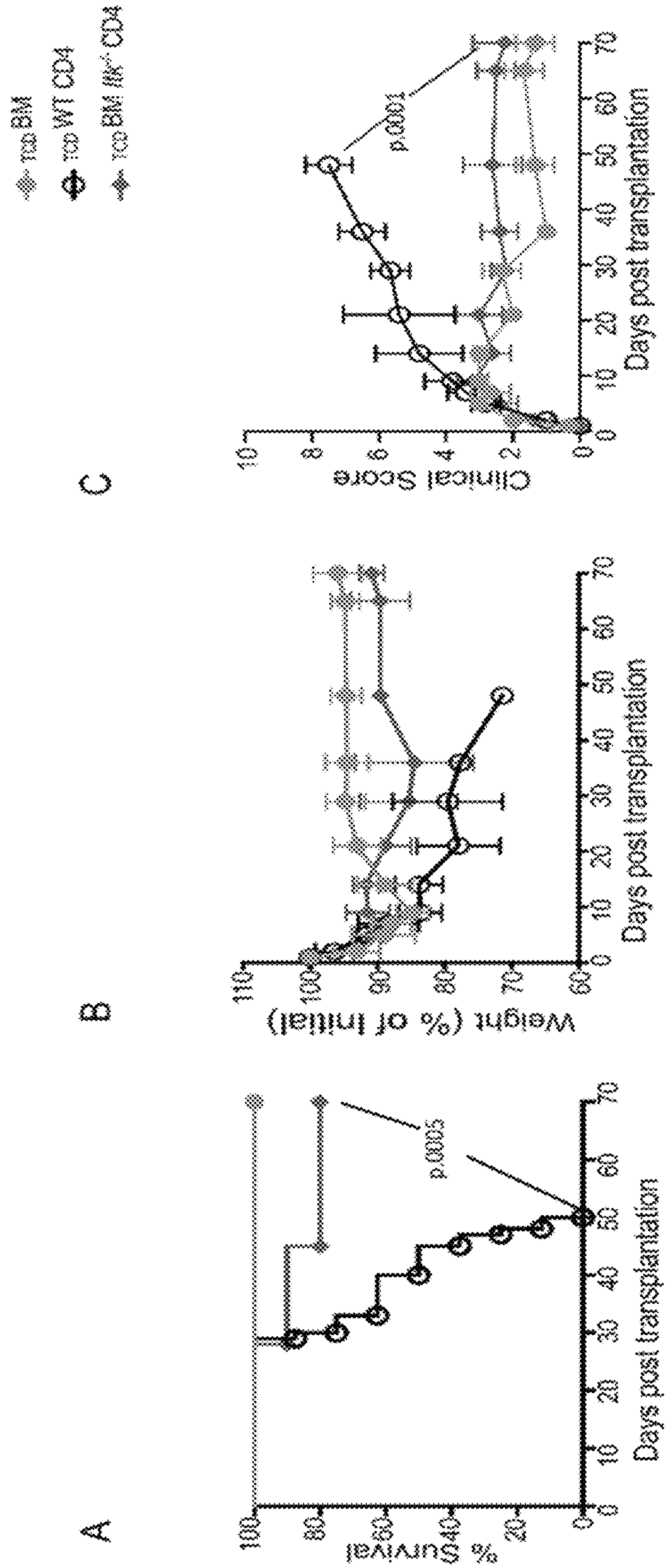
FIGS. 7A-7C depict $Itk^{-/-}$ $CD4^+$ T cells exhibiting attenuated induction of GVHD compared to WT T cells.

To determine whether TCR-mediated activation of ITK impacts GVHD pathogenesis after allo-HSCT, the effects of ITK signaling on donor $CD4^+$ and $CD8^+$ T cells was examined in an allo-transplant model, using C57Bl/6 mice (MHC haplotype b) as donors and BALB/c mice (MHC haplotype d) as recipients. To induce GVHD, MHC-mismatched donors and recipients were used, T cell-depleted bone marrow cells from B6.PL-$Thy1^a$/CyJ (Thy1.1) mice, and T cells from C57BL/6 (B6) WT or $Itk^{-/-}$ mice. Lethally irradiated BALB/c mice were injected intravenously with $10\times10^6$ wild-type (WT) T cell-depleted donor BM cells along with $2\times10^6$ FACS-sorted donor T cells ($1\times10^6$ $CD8^+$ and $1\times10^6$ $CD4^+$), followed by intravenous challenge with $2\times10^5$ luciferase-expressing B-ALL-luc blast cells as described (See e.g., Liao X C, Littman D R. Altered T cell receptor signaling and disrupted T cell development in mice lacking Itk. Immunity (1995) 3:757-69. doi: 10.1016/1074-7613 (95) 90065-9). Recipient BALB/c mice were monitored for cancer cell growth using IVIS bioluminescence imaging for over 60 days (FIG. 1A). While leukemia cell growth was observed in T cell-depleted BM-transplanted mice without T cells, leukemia cell growth was not seen in mice transplanted with T cells from either WT or $Itk^{-/-}$ mice. As expected, mice transplanted with WT T cells cleared the leukemia cells but suffered from GVHD. In contrast, mice transplanted with $Itk^{-/-}$ T cells cleared the leukemia cells and displayed minimal signs of GVHD. Most animals transplanted with $Itk^{-/-}$ T cells survived for more than 65 days post-allo-HSCT (FIG. 1B), with significantly better survival and reduced clinical scores compared to those transplanted with WT T cells (scored based on weight, posture, activity, for texture, and skin integrity as previously described (See e.g., Contag C H, Bachmann M H. Advances in in vivo bioluminescence imaging of gene expression. Annu Rev Biomed Eng (2002) 4:235-60. doi: 10.1146/annurev.bioeng.4.111901.093336) (FIGS. 1C-D)). BALB/c mice transplanted with Itk−/− T cells showed only residual tumor cell growth (as measured by bioluminescence), showing that the donor cells maintained GVT functions similar to WT T cells (FIG. 1E). Donor $CD8^+$ T cells are more potent than $CD4^+$ T cells in mediating GVL effects, but both $CD4^+$ and $CD8^+$ T cells mediate severe GVHD in mice and humans (See e.g., Amir A L, et al. Identification of a coordinated CD8 and CD4 T cell response directed against mismatched HLA Class I causing severe acute graft-versus-host disease. Biol Blood Marrow Transplant (2012) 18:210-9. doi: 10.1016/j.bbmt.2011.10.018 24; Yu X Z, et al. Alloantigen affinity and CD4 help determine severity of graft-versus-host disease mediated by CD8 donor T cells. J Immunol (2006) 176:3383-90. doi: 10.4049/jimmunol. 176.6.3383 25; and Wu T, et al. Thymic damage, impaired negative selection, and development of chronic graft-versus-host disease caused by donor CD4+ and CD8+ T cells. J Immunol (2013) 191:488-99. doi: 10.4049/jimmunol. 1300657). To determine whether $CD4^+$ T cell-intrinsic ITK signaling might be sufficient to induce GVHD, the same experiments were repeated using purified $CD4^+$ T cells from either WT or $Itk^{-/-}$ mice in the MHC-mismatch mouse model of allo-HSCT (B6→BALB/c) (FIGS. 7A-7C). Recipients of WT $CD4^+$ T cells exhibited worse survival compared to mice receiving T cell-depleted bone marrow ($_{TCD}$BM) cells alone (FIG. 7A). In contrast, recipients of $_{TCD}$BM mixed with $Itk^{-/-}$ $CD4^+$ T cells had greatly reduced mortality and clinical scores (FIG. 7B), indicating that $CD4^+$ T cell-intrinsic ITK signaling can contribute to the severity of GVHD. The results indicate that ITK signaling is dispensable for anti-leukemia immunity, but required for GVHD.

Referring specifically to FIGS. 1A-1E, FIGS. 1A-1E depict the absence of ITK avoids GVHD while retaining GVL effects during allo-HSCT. $1\times10^6$ purified CD4+ and $1\times10^6$ CD8+ T cells (WT or $Itk^{-/-}$) were mixed at a 1:1 ratio, and transplanted along with $2\times10^5$ B-ALL-luc cells into irradiated BALB/c mice. Host BALB/c mice were imaged using the IVIS imaging system 3 times a week. Group 1 received $10\times10^6$ T cell depleted bone marrow only (labeled as $_{TCD}$BM). Group 2 received $10\times10^6$ T cell depleted bone marrow along with $2\times10^5$ B-ALL-luc cells ($_{TCD}$BM+B-ALL $^{luc}$+), Group 3 was transplanted with $1\times10^6$ purified WT $CD8^+$ and $1\times10^6$ $CD4^+$ T cells (1:1 ratio) along with $2\times10^5$ B-ALL-luc+ cells $10\times10^6$ ($_{TCD}$BM+B-ALL $^{luc}$+WT CD8+CD4). Group 4 received $1\times10^6$ purified $Itk^{-/-}$ $CD8^+$ and $1\times10^6$ $CD4^+$ T cells (1:1 ratio) along with $2\times10^5$ B-ALL-luc+ cells 10×$10^6$ ($_{TCD}$BM+B-ALL$^{luc}$+Itk$^{-/-}$ CD8+ CD4). FIG. 1A depicts recipient BALB/c mice were imaged using IVIS 3 times a week. FIG. 1B depicts that the mice were monitored for survival, FIG. 1C depicts changes in body weight, and FIG. 1D depicts clinical score for 65 days post BMT. FIG. 1E depicts quantified luciferase bioluminescence of leukemia cell growth. Statistical analysis for survival and clinical score was performed using log-rank test and two-way ANOVA, respectively. For weight changes and clinical score, one representative of 2 independent experiments is shown (n=3 mice/group for BM alone; n=5 experimental mice/group for all three groups. Survival is a combination of 2 experiments. P values presented with each group. Two-way ANOVA and students t-test were used for statistical analysis. Note: Controls are naïve mice used as negative control for bioluminescence (BLI).

Referring to FIG. 7A, the figure depicts Itk$^{-/-}$ CD4$^+$ T cells exhibit attenuated induction of GVHD compared to WT T cells. FIG. 7A depicts 10×$10^6$ T cell-depleted bone marrow and 1×$10^6$ purified CD4$^+$ T cells from WT or Itk$^{-/-}$ CD4$^+$ T cells were transplanted into irradiated BALB/c mice. The mice were monitored for survival, FIG. 7B depicts changes in body weight, and FIG. 7C depicts clinical score for 70 days post-BMT. For weight changes and clinical score, one representative of 2 independent experiments is shown (n=3 mice/group for BM alone; n=5 experimental mice/group for all three groups). The p values are presented. Two-way ANOVA and Student's t test were used for statistical analysis.

Figures 2A, 2B, 2C:
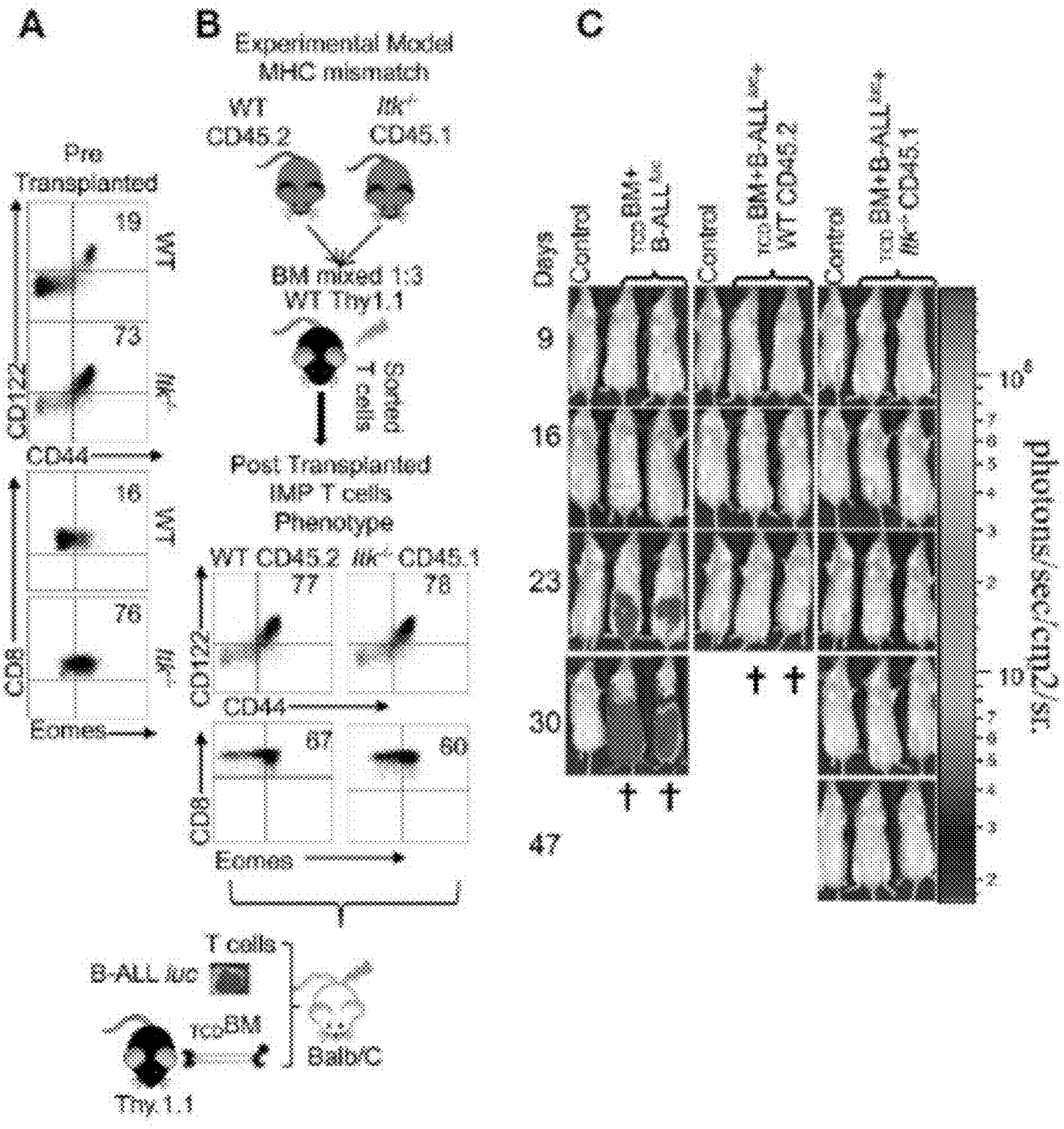
FIGS. 2A-2G depict the regulatory function of ITK in GVHD is T cell-intrinsic.

T Cells Innate Memory Phenotype (IMP) is not Sufficient for GVHD Effects, and the Regulatory Function of ITK in GVHD is T Cell-Intrinsic The innate memory phenotype (IMP: CD44$^{hi}$CD122$^{hi}$ and Eomes$^{hi}$) (See e.g, Huang W. Hu J, August A. Cutting edge:inate memory CD8+ T cells are distinct from homeostatic expanded CD8+ T cells and rapidly respond to primary antigenic stimulo. J. Immunol (2013) 190:2490-4. Doi: 10.4049/jimmunol. 1202988) of Itk$^{-/-}$ CD8$^+$ T cells arises in the thymus during development, as opposed to memory CD8$^+$ T cells that are also CD44$^{hi}$, but largely arise in the periphery of WT mice in response to foreign antigens or due to homeostatic proliferation (See e.g., Weinreich M A, et al., T cells expressing the transcription factor PLZF regulate the development of memory-like CD8+ T cells. Nat Immunol (2010) 11:709-16. doi: 10.1038/ni.1898). Pre-transplanted CD8$^+$ T cells for CD44$^{hi}$CD122$^{hi}$ and Eomes $^{hi}$ expression was examined, and it was observed that Itk$^{-/-}$ CD8$^+$ T cells expressed substantially higher levels of CD44$^{hi}$CD122$^{hi}$ and Eomes$^{hi}$ compared to CD8$^+$ T cells from WT mice (FIG. 2A). It was sought to understand whether the emergence of IMP is sufficient to separate GVHD from GVL. To test this, WT IMP T cells were generated using a mixed-bone marrow approach in which T cell-depleted BM from WT and Itk$^{-/-}$ mice were mixed at a 3:1 (WT:Itk$^{-/-}$) ratio (See e.g., Huang W, et al., Cutting edge: innate memory CD8+ T cells are distinct from homeostatic expanded CD8+ T cells and rapidly respond to primary antigenic stimuli. J Immunol (2013) 190:2490-4. doi: 10.4049/jimmunol.1202988). The irradiated syngeneic (B6) Thy1.1 hosts were reconstituted with this mixture of T cell-depleted CD45.2$^+$ WT and CD45.1$^+$ Itk$^{-/-}$ BM cells, along with a control group receiving mixed CD45.2$^+$ WT and CD45.1$^+$ WT BM cells (FIG. 2B). WT BM-derived CD8$^+$ thymocytes that develop in such mixed BM chimera acquire an IMP phenotype due to their development in the same thymus as the Itk$^{-/-}$ T cells, which was also observed in the experiments (FIG. 2B). Ten weeks after reconstitution of the T cell compartment, T cells derived from WT (CD45.2$^+$Thy1.1$^-$) and Itk$^{-/-}$ (CD45.1$^+$) donor cells were sorted from the bone marrow chimeras. These sorted T cells were transplanted into irradiated BALB/c mice along with $_{TCD}$BM in the allo-HSCT model as described above, and tested for their function in GVHD and GVL. Analysis of the BALB/c recipients of these different IMP CD8$^+$ T cells indicates that WT IMP cells were not able to separate GVL and GVHD effects (FIG. 2C-G). Thus, the appearance of IMP is not sufficient to separate GVHD from GVL.

Figures 2D, 2E, 2F, 2G:
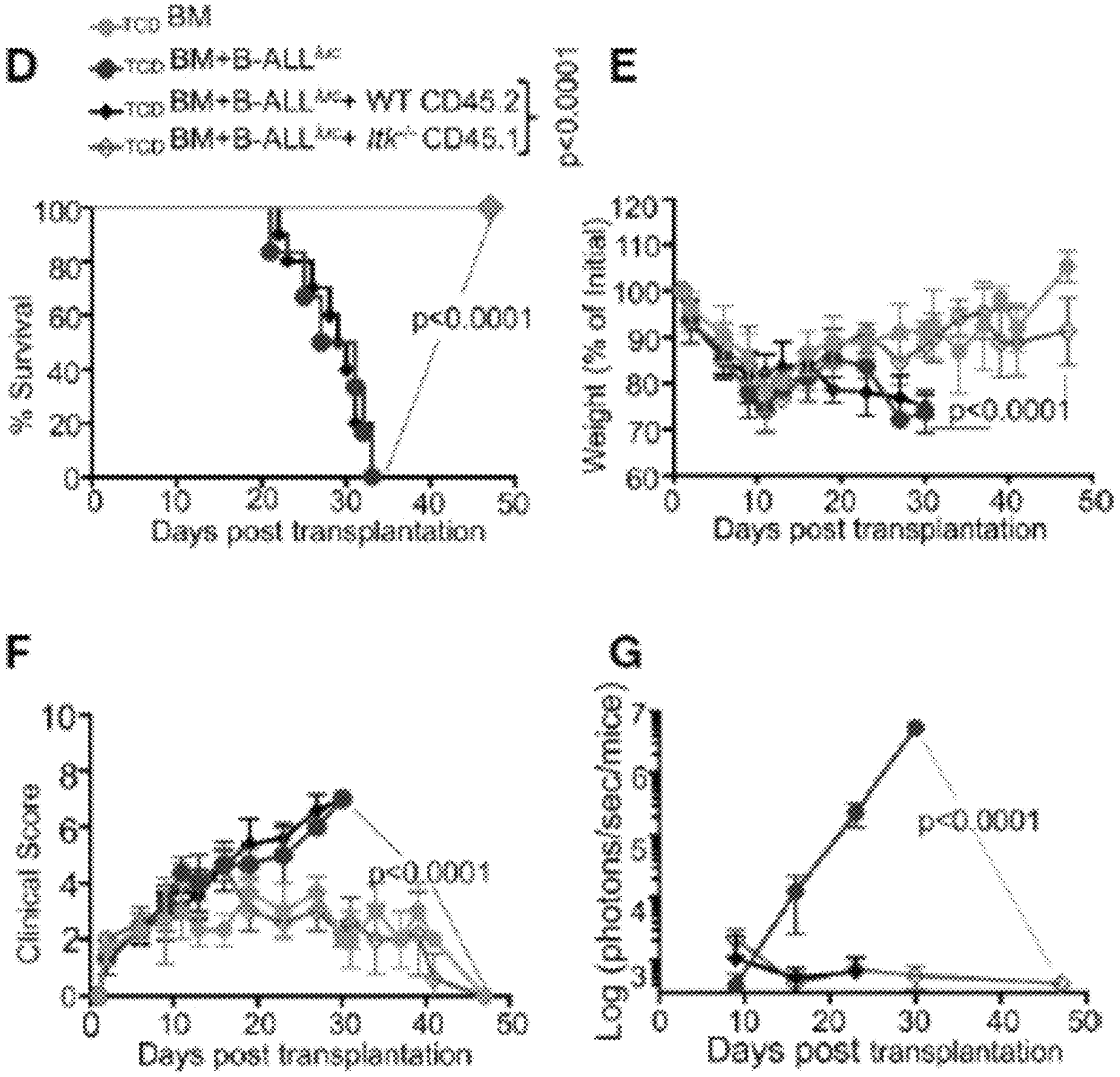

More specifically, FIGS. 2A-2G depict the regulatory function of ITK in GVHD is T cell-intrinsic. FIG. 2A depicts purified WT and Itk$^{-/-}$ CD8$^+$ T cells were examined for expression of CD44 prior to transplantation. FIG. 2B depict whole bone marrow cells isolated from C57Bl/6 WT (CD45.2) and Itk$^{-/-}$ (CD45.1) mice were mixed in 1:3 ration WT:Itk$^{-/-}$, and transplanted into irradiated Thy1.1 C57Bl/6 mice. 9-10 weeks later CD8$^+$ T cells were sorted by CD45.2 and CD45.1 expression (donor T cells) and exclusion of Thy1.1 positive (host T cells). Isolated sorted T cells were examined for expression of CD44, and transplanted into irradiated BALB/c mice. This experiment was repeated more than three times. FIG. 2C depicts irradiated BALB/c mice were divided in four different groups and transplanted with the sorted T cells described in FIG. 2B as follows: Group one was transplanted with 10×$10^6$ $_{TCD}$BM alone ($_{TCD}$BM). Group two was transplanted with 10×$10^6$ $_{TCD}$BM and 2×$10^5$ B-ALL-luc, ($_{TCD}$BM+B-ALL$^{luc}$). Group three was transplanted with 10×$10^6$ $_{TCD}$BM along with 1×$10^6$ purified WT CD8$^+$ T cells and 2×$10^5$ B-ALL-luc ($_{TCD}$BM+B-ALL$^{luc}$+WT CD45.2). The fourth group was transplanted 10×$10^6$ $_{TCD}$BM along with and 1×$10^6$ purified Itk$^{-/-}$ CD8$^+$ T cells and 2×$10^5$ B-ALL-luc ($_{TCD}$BM+B-ALL$^{luc}$+Itk$^{-/-}$ CD45.1). These mice were monitored for leukemia cell growth using the IVIS system. In FIG. 2D, the mice were monitored for survival, in FIG. 2E changes in body weight, and in FIG. 2F clinical score for 47 days post BMT. For body weight changes and clinical score, one representative of 2 independent experiments is shown (n=3 mice/group for BM alone; n=5 experimental mice/group for all three groups). In FIG. 2G quantified luciferase bioluminescence of luciferase expressing B-ALL-luc cells is shown. Statistical analysis for survival and clinical score was performed using log-rank test and two-way ANOVA, respectively. One representative experiment out of 2. Survival is a combination of 2 experiments, 3 mice per group of control T cell-depleted bone marrow, and 5 mice per group for all of the experimental groups. P value presented with each figure. Note: Controls are naïve mice used as negative control for BLI.

Figures 3A, 3B, 3C, 3D, 3E, 3F, 3G, 3H, 3I:
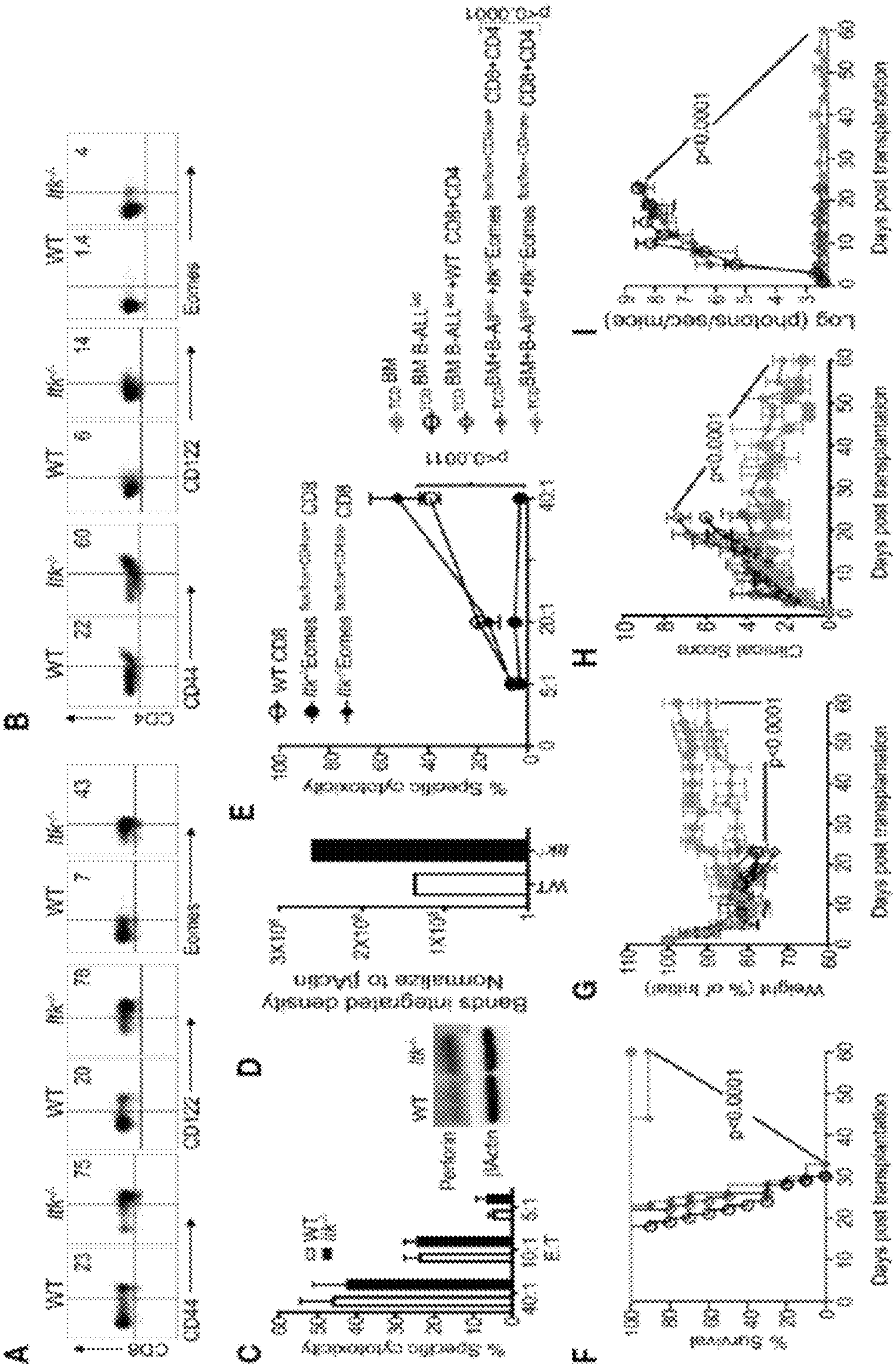
FIGS. 3A-3I depict innate memory phenotype T cells are not sufficient for GVL effect.
Figures 8A, 8B, 8C:
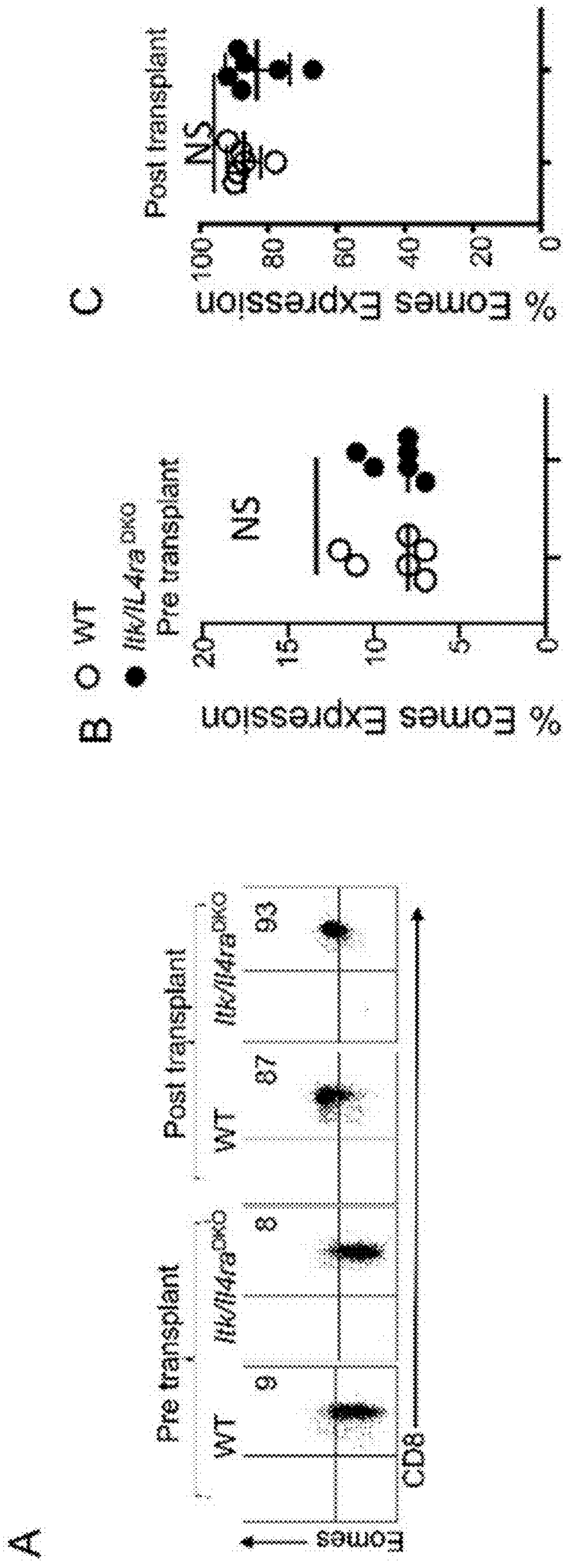
FIGS. 8A-8G depict innate memory phenotype T cells are not sufficient for GVHD effect.
Figures 8D, 8E, 8F, 8G:
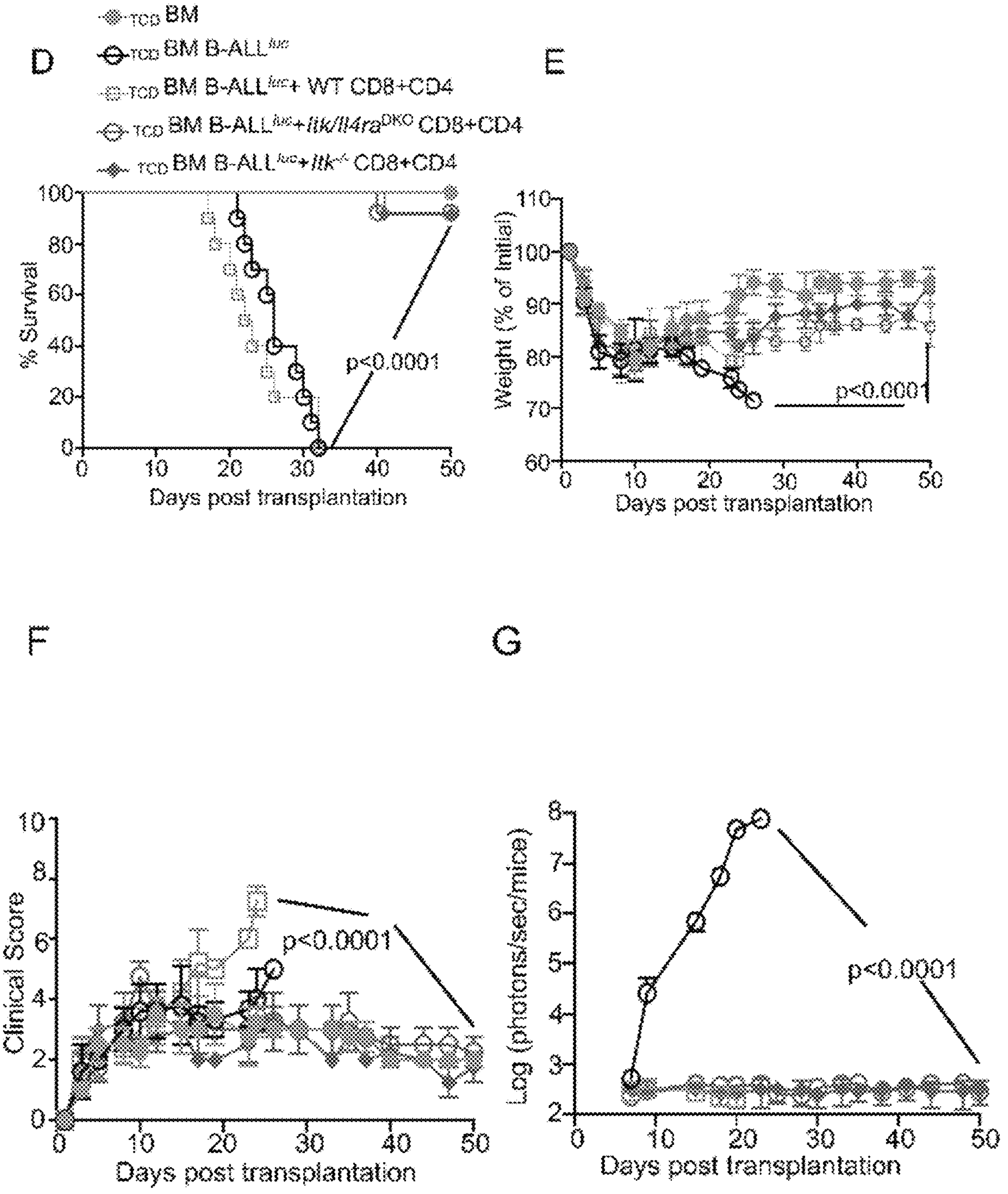

As previously discussed, Itk$^{-/-}$ CD8$^+$ and CD4$^+$ T cells exhibit attenuated TCR signaling and an innate memory phenotype (IMP)[25], as indicated by expression of high levels of CD44, CD122, and the key transcription factor Eomes, specifically on CD8$^+$ T cells (FIGS. 3A-B). To examine whether these IMP T cells from Itk$^{-/-}$ mice mount GVL responses, the MHC-mismatch mouse model of allo-HSCT (WT, Itk$^{-/-}$ →BALB/c, i.e., H2K$^{b+}$→H2K$^{d+}$) was used. Then H2K$^{b+}$ donor T cells were sorted back from recipient mice and determined their cytotoxicity against B-ALL-luc cells. It was found that these donor cells effectively killed primary leukemia cells in vitro, even in the absence of ITK (FIG. 3C). Moreover, significantly increased expression of perforin in CD8$^+$ T cells was observed from Itk$^{-/-}$ mice compared to T cells from WT mice, in the absence of activation (FIG. 3D). The findings demonstrate that CD8$^+$ T cells from Itk$^{-/-}$ mice have enhanced activation, and exert cytotoxicity against primary leukemia cells. IL-4 is known to upregulate Eomes in $CD8^+$ T cells (See e.g., Weinreich, M. A., et al., T cells expressing the transcription factor PLZF regulate the development of memory-like CD8+ T cells. *Nat Immunol* 11, 709-716 (2010); and Pikovskaya, O. et al. Cutting Edge: Eomesodermin Is Sufficient To Direct Type 1 Innate Lymphocyte Development into the Conventional NK Lineage. *J Immunol* 196, 1449-1454 (2016)) were verified by comparing T cells from WT and Itk/Il4ra double KO (DKO) mice. Removing IL-4 signaling from the $Itk^{-/-}$ mice led to decreased expression of Eomes compared to T cells from $Itk^{-/-}$ and WT pre-transplanted (FIG. 8A). Next the short-term allo-HSCT model was used, where T cells from WT or Itk/Il4ra DKO were transplanted into irradiated BALB/c mice. 7 days post transplantation, WT or Itk/Il4ra DKO donor T cells were then sorted back from the BALB/c recipient mice, and Eomes expression on these donor T cells was determined. No differences were observed between the donor WT or Itk/Il4ra T cells upon allo activation (FIGS. 8A-C). Next, the function of Itk/Il4ra DKO T cells in the long term allo-HSCT model was tested, and observed that donor T cells from Itk/Il4ra DKO mice did not induce GVHD, and most of the animals survived compared to recipients of WT T cells (FIG. 8D). BALB/c transplanted with Itk/Il4ra donor T cells also had much less weight loss and significantly better clinical scores compared to BALB/c mice transplanted with WT donor T cells (FIG. 8D-G). Furthermore, Itk/Il4ra DKO donor T cells cleared leukemia cells without inducing GVHD (FIG. 3G). These data show that the IMP T cell phenotype may not be critical for GVHD, but modulating ITK does impact GVHD without affecting GVL.

To investigate the role of Eomes in clearing leukemia cells and in cytotoxic function, $Itk^{-/-}$ mice with $Eomes^{flox/flox}$ mice were crossed, and crossed these offspring with CD4cre mice, to delete Eomes specifically in T cells (See e.g., Pikovskaya, O. et al. Cutting Edge: Eomesodermin Is Sufficient To Direct Type 1 Innate Lymphocyte Development into the Conventional NK Lineage. *J Immunol* 196, 1449-1454 (2016); and D'Aveni, M. et al. G-CSF mobilizes CD34+ regulatory monocytes that inhibit graft-versus-host disease. *Sci Transl Med* 7, 281ra242 (2015)) to generate (Itk/Eomes DKO). Similar allo-HSCT experiments were performed as described above, and used WT or Itk/Eomes DKO T cells. Seven days post-transplant, donor T cells were sorted using $H2K^b$ expression, and in vitro cytotoxicity assays were performed at a 5:1, 20:1 and 40:1 ratio (effector: target). The data show that ex vivo donor Itk/Eomes DKO were unable to kill cancer targets (FIG. 3F). To examine the role of Eomes in the allo-HSCT model, BALB/c mice were lethally irradiated and injected intravenously with $10\times10^6$ WT T cell-depleted BM cells along with FACS-sorted $CD8^+$ and $CD4^+$ T cells from donor mice (WT, $Itk^{-/-}$ Eomes DKO). This was followed by intravenous challenge with $2\times10^5$ luciferase-expressing B-ALL-luc blast cells as described(17). Recipient animals transplanted with WT T cells cleared the tumor cells but had reduced survival and GVHD (FIG. 3G-J). Recipient animals transplanted with $Itk^{-/-}$ Eomes DKO T cells however, did not cleared the leukemia cells without showing signs of GVHD (FIG. 3I). Notably, recipient animals transplanted with Itk/Eomes DKO T cells mice were unable to clear the tumor and all died from cancer burden. These data provided further evidence that Eomes is required for the GVL effect.

More specifically, referring to FIGS. 3A-3I it is depicted that innate memory phenotype T cells are not sufficient for GVL effect. FIGS. 3A and 3B depict purified WT and $Itk^{-/-}$ $CD8^+$ and $CD4^+$ T cells were examined for expression of CD44, CD122, and Eomes by flow cytometry. FIG. 3C depicts purified WT or $Itk^{-/-}$ T cells were transplanted into irradiated BALB/c mice, at day 7 purified T cells were sorted using $H2K^d$, CD45.1 and CD45.2 expression. Ex vivo purified $CD8^+$ T cells were used in cytotoxicity assay against primary leukemia target B-ALLluc+ cells at a 40:1, 20:1, or 5:1 ratio. FIG. 3D depicts purified T cells were examined for perforin by western blot. FIG. 3E depicts quantitative analysis of four experiments of perforin expression by western blot with data normalized against B-Actin. FIG. 3F depicts purified WT or Itk/Eomes DKO donor T cells were transplanted into irradiated BALB/c mice. On day 7 donor T cells were purified as described and used in an ex vivo cytotoxicity assay against $B\text{-}ALL^{luc}$-cells at 5:1, 20:1, and 40:1 ratios. FIG. 3G depicts $1\times10^6$ purified WT and $Itk^{-/-}$ Itk/Eomes DKO $CD8^+$ T cells and $1\times10^6$ purified $CD4^+$ T total of $2\times10^6$ mixed $CD4^+$ and $CD8^+$ T cells were mixed and transplanted along with $2\times10^5$ B-ALL-luc cells and $10\times10^6$ T cell-depleted bone marrow cells into irradiated BALB/c mice. Host BALB/c mice were imaged using IVIS 3 times a week. Group one received $10\times10^6$ T cell-depleted bone marrow alone as ($_{TCD}$BM). Group two received $10\times10^6$ T cell-depleted bone marrow along with $2\times10^5$ B-ALL-luc cells ($_{TCD}BM+B\text{-}ALL^{luc}$). Group three were transplanted with $10\times10^6$ T cell-depleted bone marrow and $1\times10^6$ purified WT $CD8^+$ T cells+$1\times10^6$ $CD4^+$ T cells and $2\times10^5$ B-ALL-luc cells ($_{TCD}BM+B\text{-}ALL^{luc}$+WT CD8+CD4). Group four received $10\times10^6$ T cell-depleted bone marrow and $1\times10^6$ purified $CD8^+$ T cells+$1\times10^6$ $CD4^+$ T cells from Itk/Eomes DKO along with $2\times10^5$ B-ALL-luc cells ($_{TCD}BM+B\ ALL^{luc}+Itk^{-/-}$ EomesFF+CD4cre CD8+CD4). Group five received $10\times10^6$ T cell-depleted bone marrow and $1\times10^6$ $CD8^+$ T cells $+1\times10^6$ $CD4^+$ purified T cells Itk/Eomes DKO $CD4^+$ T cells along with $2\times10^5$ B-ALL-luc cells ($_{TCD}BM+B\text{-}ALL^{luc}+Itk^{-/-\ EomesFF+CD4cre-}$ CD8+ CD4). FIG. 3G depicts the mice were monitored for survival, FIG. 3H depicts body weight changes, and FIG. 3I depicts clinical score for 60 days post BMT. For weight changes and clinical score, one representative of 2 independent experiments is shown (n=3 mice/group for BM alone; n=5 experimental mice/group for all three group. The survival groups are a combination of all experiments. The figures depict quantitated luciferase bioluminescence of tumor growth. Statistical analysis for survival and clinical score was performed using log-Two-way ANOVA were used for statistical analysis confirming by students t test, p values are presented. Note: Controls are naïve mice used as negative control for bioluminescence (BLI).

More specifically, referring to FIGS. 8A-8G, it is depicted that innate memory Phenotype T cells are not sufficient for GVHD effect. FIGS. 8A-8C depict Itk/Il4ra DKO and WT T cells were examined for Eomes expression pre- and post-transplantation. FIG. 8D depicts $2\times10^6$ purified WT and Itk/Il4ra DKO $CD8^+$ T and $1\times10^6$ purified $CD4^+$ T cells were mixed and transplanted along with $2\times10^5$ primary B-ALL-luc+ cells into irradiated BALB/c mice. Recipient BALB/c mice were imaged using IVIS 3 times a week. Group one received $10\times10^6$ T cell-depleted bone marrow alone ($_{TCD}$BM). Group two received $10\times10^6$ T cell-depleted bone marrow along with $2\times10^5$ B-ALL-luc cells ($_{TCD}BM+B\text{-}ALL^{luc}$). Group three was transplanted $10\times10^6$ T cell-depleted bone marrow with $2\times10^6$ purified ($CD8^+$ and $CD4^+$) from WT mice and $2\times10^5$ B-ALL-luc cells ($_{TCD}BM+B\text{-}ALL\ ^{luc}$+WT CD8+CD4). Group four was transplanted $10\times10^6$ T cell-depleted bone marrow and $2\times10^6$ purified T cells ($CD8^+$ and $CD4^+$) from Itk/Il4ra DKO along with $2\times10^5$ B-ALL-luc cells ($_{TCD}BM+B\text{-}ALL^{luc}$+Itk/Il4ra DKO $CD8^+CD4$). Recipient animals were monitored for survival, FIG. 8E depicts changes in weight, and FIG. 8F depicts clinical score. FIG. 8G depicts Leukemia cell growth was monitored as in FIG. 1, and quantitated bioluminescence is shown. One representative of 2 independent experiments is shown (n=3 mice/group for BM alone; n=5 experimental mice/group for all three groups. The survival groups were combinations of all experiments.

ITK Deficiency Results in Reduced Cytokine Production.

Figures 4A, 4B, 4C, 4D, 4E, 4F, 4G, 4H, 4I:
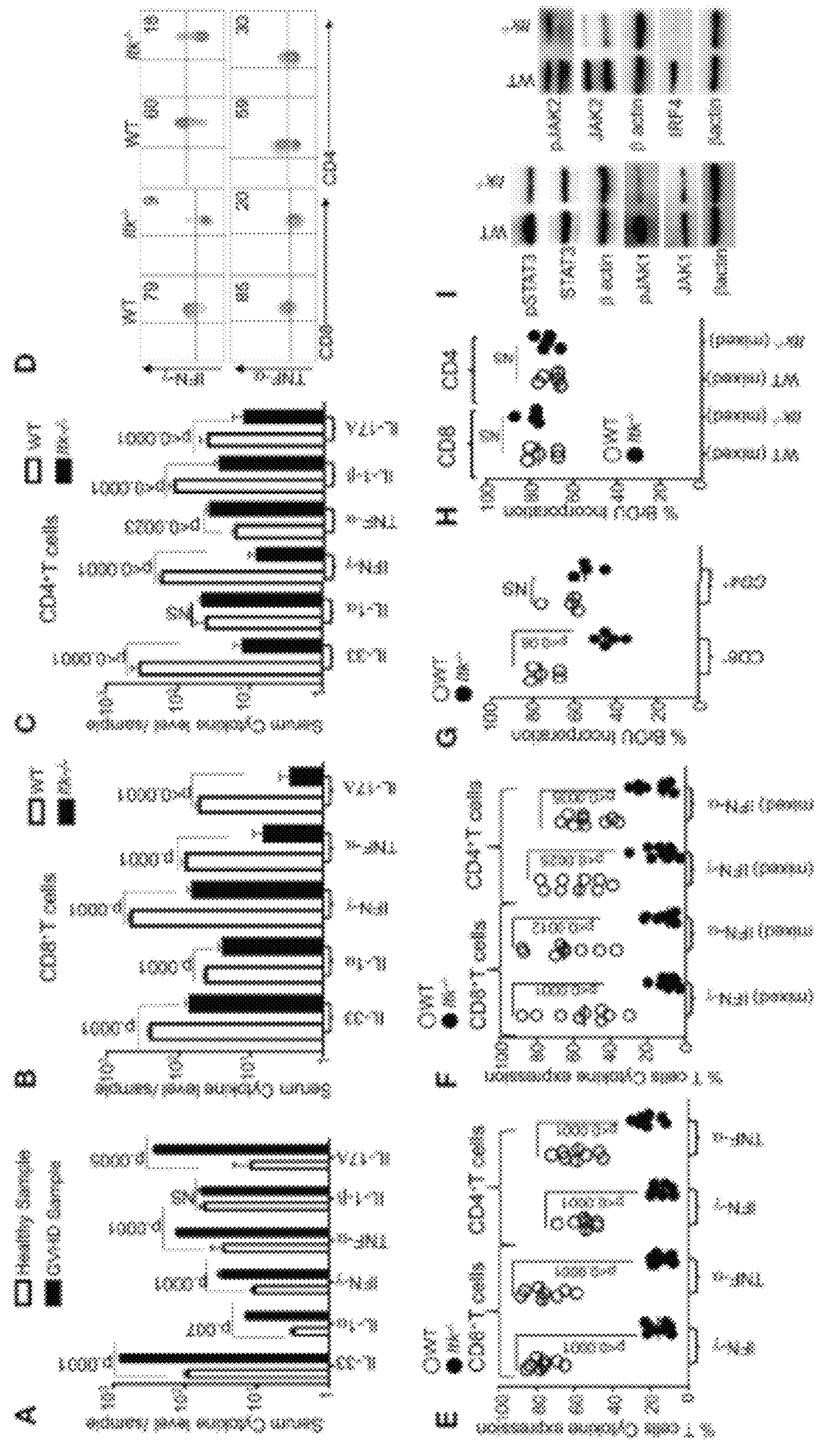
FIGS. 4A-4I depict ITK deficiency results in reduced cytokine production.
Figure 9:
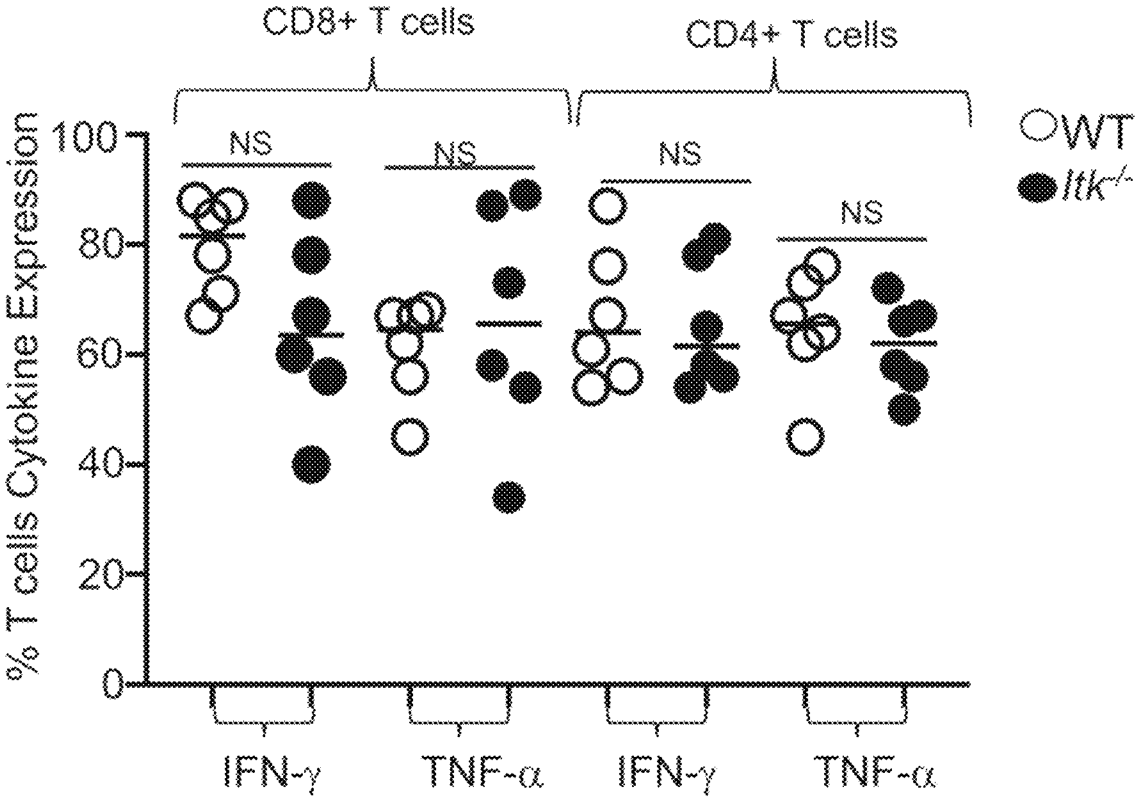
FIG. 9 depicts $Itk^{-/-}$ T cells are capable of cytokine production.
Figures 10A, 10B, 10C, 10D:
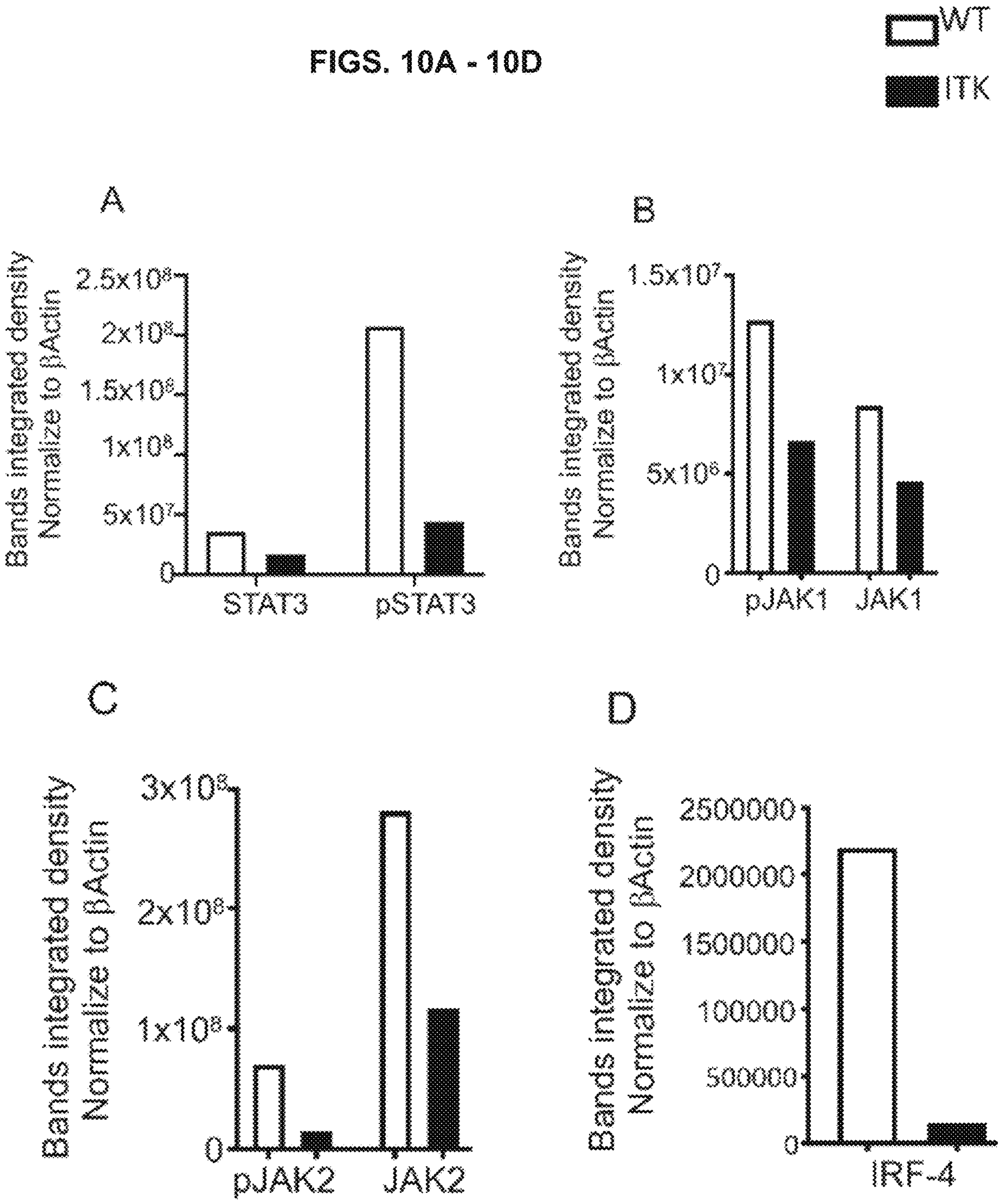
FIGS. 10A-10D depict quantitative analysis of JAK/STAT and IRF expression and phosphorylation.

It is known that the conditioning regimen for allo-HSCT elicits an increase in the production of inflammatory cytokines by donor T cells, known as a "cytokine storm", and this is considered to be one of the hallmarks of GVHD pathogenesis (See e.g., D'Aveni M, Rossignol J, Coman T, Sivakumaran S, Henderson S, Manzo T, et al. G-CSF mobilizes CD34+ regulatory monocytes that inhibit graft-versushost disease. Sci Transl Med (2015) 7: 281ra242. doi: 10.1126/scitranslmed.3010435). Blood samples were obtained from GVHD patients and healthy donors and examined the levels of serum inflammatory cytokines such as IL-33, IL-1α, IFNγ, TNFα and IL-17A. It was observed that patients with GVHD have significantly higher levels of serum proinflammatory cytokines compared to healthy controls (FIG. 4A). Next, cytokine production was assessed by $Itk^{-/-}$ CD8 and CD4 T cells in the allo-HSCT model (B6→BALB/c), examining the levels of serum inflammatory cytokines such as IL-33, IL-1α, IFN-γ, TNF-α and IL-17A on day 7 post allotransplantation (FIG. 4B-C). It was found that serum IFN-γ and TNF-α were significantly reduced in recipients that received $Itk^{-/-}$ $CD8^+$ T or $CD4^+$ T cells compared to those that received WT $CD8^+$ or $CD4^+$ T cells (FIG. 4B-C). Thus, it was confirmed that the findings in the pre-clinical model correlated with what was found in human GVHD samples. $Itk^{-/-}$ donor T cells were isolate from the secondary lymphoid organs of recipients using anti-$H2K^b$ antibodies (expressed by donor C57Bl/6 cells). The cells were stimulated with anti-CD3/CD28 (FIG. 4D), or PMA/ionomycin (to bypass the proximal TCR signaling defect (See e.g., Biswas, P. S. et al. Phosphorylation of IRF4 by ROCK2 regulates IL-17 and IL-21 production and the development of autoimmunity in mice. *J Clin Invest* 120, 3280-3295 (2010)) (FIG. 9), in the presence of Brefeldin A, or left unstimulated for 6 hours, followed by analysis of IFN-γ and TNF-α cytokine production. $Itk^{-/-}$ T cells were capable of producing IFN-γ and TNF-α at levels comparable to WT cells when both $CD8^+$ and $CD4^+$ T cell signaling was bypassed by re-stimulation with PMA and ionomycin (FIG. 9). However, the $Itk^{-/-}$ cells produced significantly less inflammatory cytokines when stimulated via TCR/CD28 than WT cells did (FIG. 4D-E). Next, it was determined whether the reduction of cytokine production by $Itk^{-/-}$ donor T cells was due to cell-intrinsic or extrinsic factors. Purified $Itk^{-/-}$ $CD8^+$ T and CD4 T cells were mixed with purified WT $CD8^+$ or $CD4^+$ T cells separately at a 1:1 ratio, and transplanted the mixed cells into irradiated BALB/c mice as described above. On day 7, donor T cells were isolated from recipient mice using $H2K^b$+ and examined for IFN-γ and TNF-α expression as described above. It was found that WT donor $CD8^+$ and $CD4^+$ T cells produced higher levels of inflammatory cytokines than $Itk^{-/-}$ donor $CD8^+$ and $CD4^+$ T cells, respectively, suggesting that the reduced cytokine production observed by $Itk^{-/-}$ donor T cells is T cell-intrinsic (FIG. 4F).

Next donor $CD4^+$ and $CD8^+$ T cell proliferation were examined using a BrdU incorporation assay. 7 days post allo-transplantation as described above, transplanted $CD4^+$ and $CD8^+$ T cells were examined for proliferation by BrdU incorporation. $Itk^{-/-}$ donor $CD8^+$ and $CD4^+$ T cells showed reduced proliferation compared to WT donor $CD8^+$ and $CD4^+$ T cells (FIG. 4G). To determine if the reduced proliferation of $Itk^{-/-}$ donor T cells was due to cell-intrinsic mechanisms, sort purified mixed $Itk^{-/-}$ and WT $CD4^+$ or $Itk^{-/-}$ and WT $CD8^+$ were mixed at a 1:1 ratio, followed by transplantation as described above. Interestingly, no difference was observed in BrdU incorporation between WT and $Itk^{-/-}$ donor $CD4^+$ and $CD8^+$ T cells in the mixed transplant models, indicating that the reduced proliferation of donor $Itk^{-/-}$ T cells proliferation was due to cell-extrinsic effects (FIG. 4H). Thus, both cell intrinsic and extrinsic mechanisms regulate the behavior of $Itk^{-/-}$ $CD8^+$ and $CD4^+$ donor T cells.

The transcription factor IRF4 has been shown to play critical roles in maintaining TCR signaling, including TCR signal strength such as those regulated by ITK[31]. The JAK/STAT signaling pathway is also critical for the response of T cells to cytokines[32, 33]. To examine whether there was a difference in these signaling pathways between WT and $Itk^{-/-}$ donor T cells in the GVHD and GVL model, expression of IRF4, JAK1, JAK2 and STAT3 was examined by purified T cells from spleens. The data showed that $Itk^{-/-}$ donor T cells expressed significantly less IRF4, JAK1, JAK2, and STAT3 as well as phosphorylated forms of JAK1, JAK2 and STAT3 (FIG. 4I and FIG. 10A-10D). The data suggest that the lack of ITK affects the expression of IRF4, and thus the amount of cytokine signals the cells received. These data may explain the reduced cytokine production and proliferation in $Itk^{-/-}$ T cells observed above.

More specifically, FIGS. 4A-4I depicts ITK deficiency results in reduced cytokine production. FIG. 4A depicts serum from several GVHD patients was isolated and examined for inflammatory cytokine production (IL-33, IL1γ, IFN-γ and TNF-α, IL1β and IL-17A) as determined by ELISA. (FIGS. 4B-4C) $1\times10^6$ purified WT or $Itk^{-/-}$ CD8+ T or $CD4^+$ T cells were separately transplanted with into irradiated BALB/c mice. At day 7 post allo-HSCT, recipient BALB/c were euthanized and serum cytokines (IL-33, IL1β, IFN-γ and TNF-α and IL-17A) were measured by ELISA. FIG. 4D depicts Intracellular IFN-γ and TNF-α expression by donor $CD8^+$ and $CD4^+$ T cells after stimulation with anti-CD3/anti-CD28 as determined by flow cytometry. FIGS. 4E-4F depict combined data from 3 independent experiments is shown for each experiment shown in figures. FIG. 4F depicts flow cytometry analysis of purified WT and $Itk^{-/-}$ T cells that were mixed at a 1:1 ratio for transplantation into irradiated BALB/c mice. At day 7 donor T cells were gated for expression of H-$2K^b$, CD45.1, and CD45.2 and intracellular expression of IFN-γ and TNF-α was analyzed by flow cytometry after stimulation with anti-CD3/anti-CD28. Combined data from 4 independent experiments is shown, and the p value for each experiment is shown. FIG. 4G depicts purified WT or $Itk^{-/-}$ donor $CD8^+$ and $CD4^+$ T cells were transplanted into irradiated BALB/c. At day 7 donor cells were analyzed for donor T cell proliferation by examining BrdU incorporation by flow cytometry. FIG. 4H depicts purified WT and $Itk^{-/-}$ donor T cells were mixed at a 1:1 WT:$Itk^{-/-}$ ratio and transplanted into irradiated BALB/c mice, at day 7 donor T cells were gated for the expression of H-$2K^b$, CD45.1, and CD45.2 and analyzed for BrDU incorporation. FIG. 4I depicts purified WT and $Itk^{-/-}$ T cells were examined for the expression and phosphorylation of IRF4, JAK1/2 and STAT3 by western blot. For statistical analysis two-way ANOVA and student's t test was used, p values are presented.

Referring now to FIG. 9, FIG. 9 depicts $Itk^{-/-}$ T cells are capable of cytokine production. Purified WT and $Itk^{-/-}$ T cells were transplanted into irradiated BALB/c mice. At day 7, donor T cells were gated for expression of H-$2K^b$, CD45.2, and CD45.1, and analyzed for intracellular expression of IFN-γ and TNF-α following ex vivo stimulation with PMA/ionomycin. Data from several experiments were combined and statistical analysis was performed using two-way ANOVA and Student's t test, with p values presented.

Referring to FIGS. 10A-10D, FIGS. 10A-10D depict quantitative analysis of JAK/STAT and IRF expression and phosphorylation. Quantitative analysis from western blots using Image Lab to normalize to B-Actin, data from 3 independent experiments. (A) Phospho and total STAT3. (B) Phospho and total JAK1. (C) Phospho and total JAK2. (D) Total IRF-4. For statistical analysis we used two-way ANOVA and student's t test, p values are presented.

ITK Differentially Regulates Gene Expression in T Cells During GVHD.

Figures 5A, 5B, 5C:
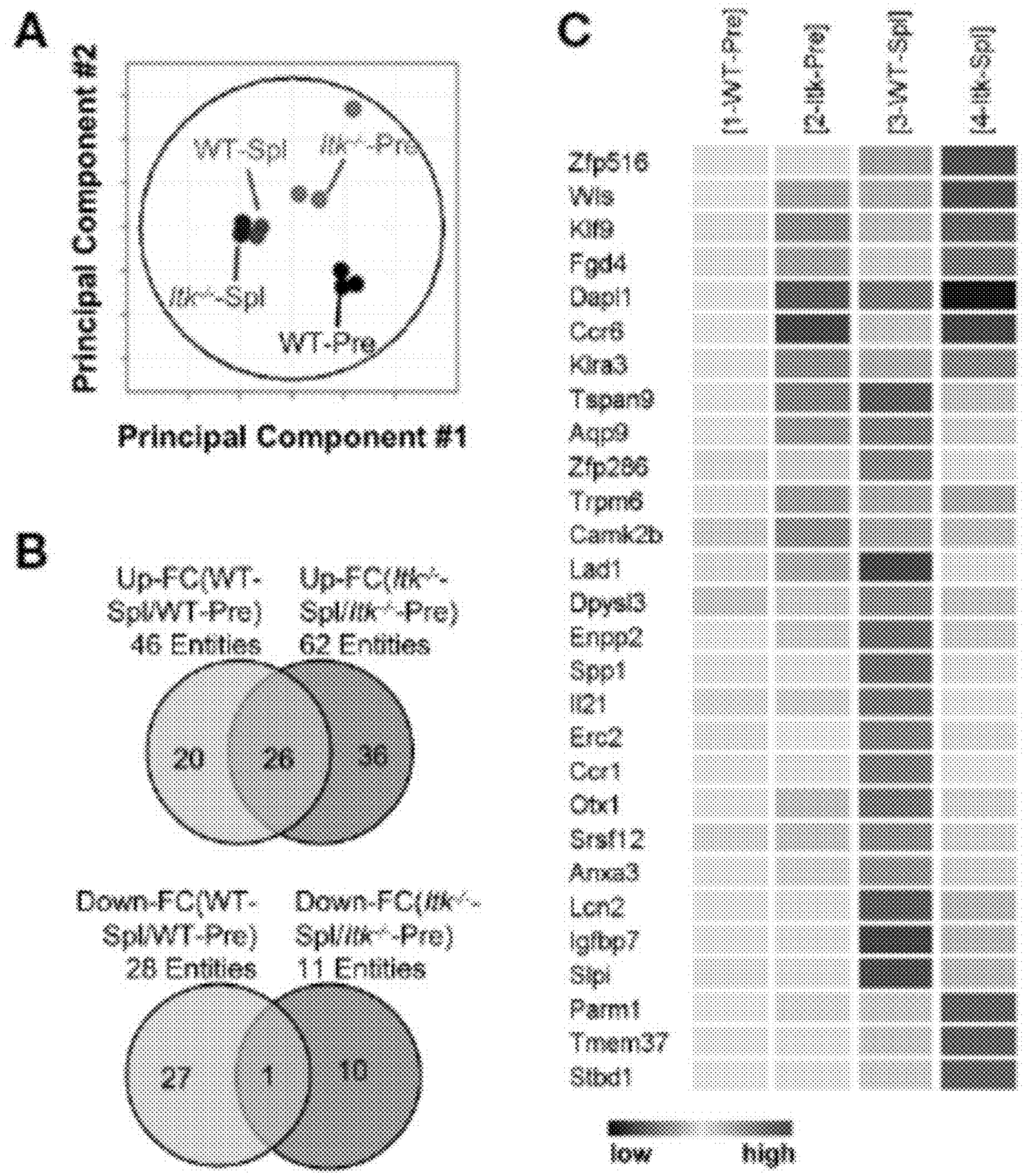
FIGS. 5A-5E depict ITK differentially regulates gene expression in T cells during GVHD.
Figures 5D, 5E:
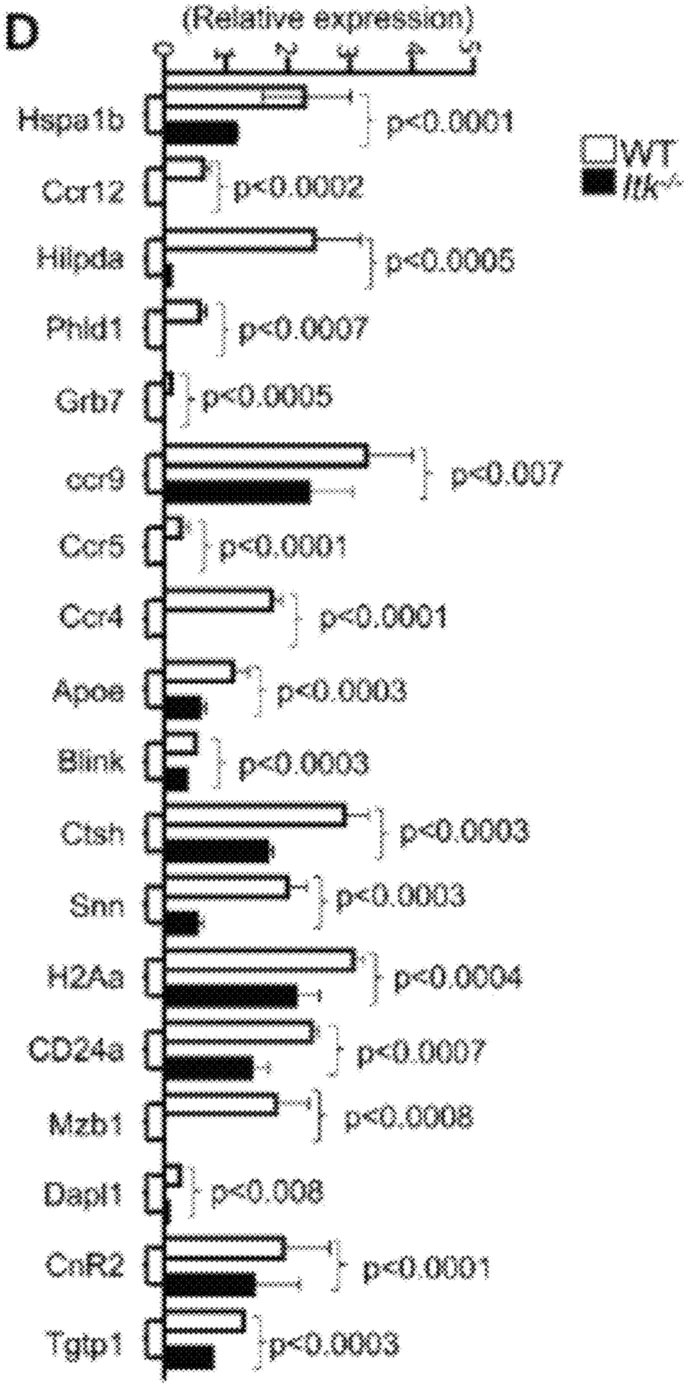
Figures 6A, 6B, 6C, 6D:
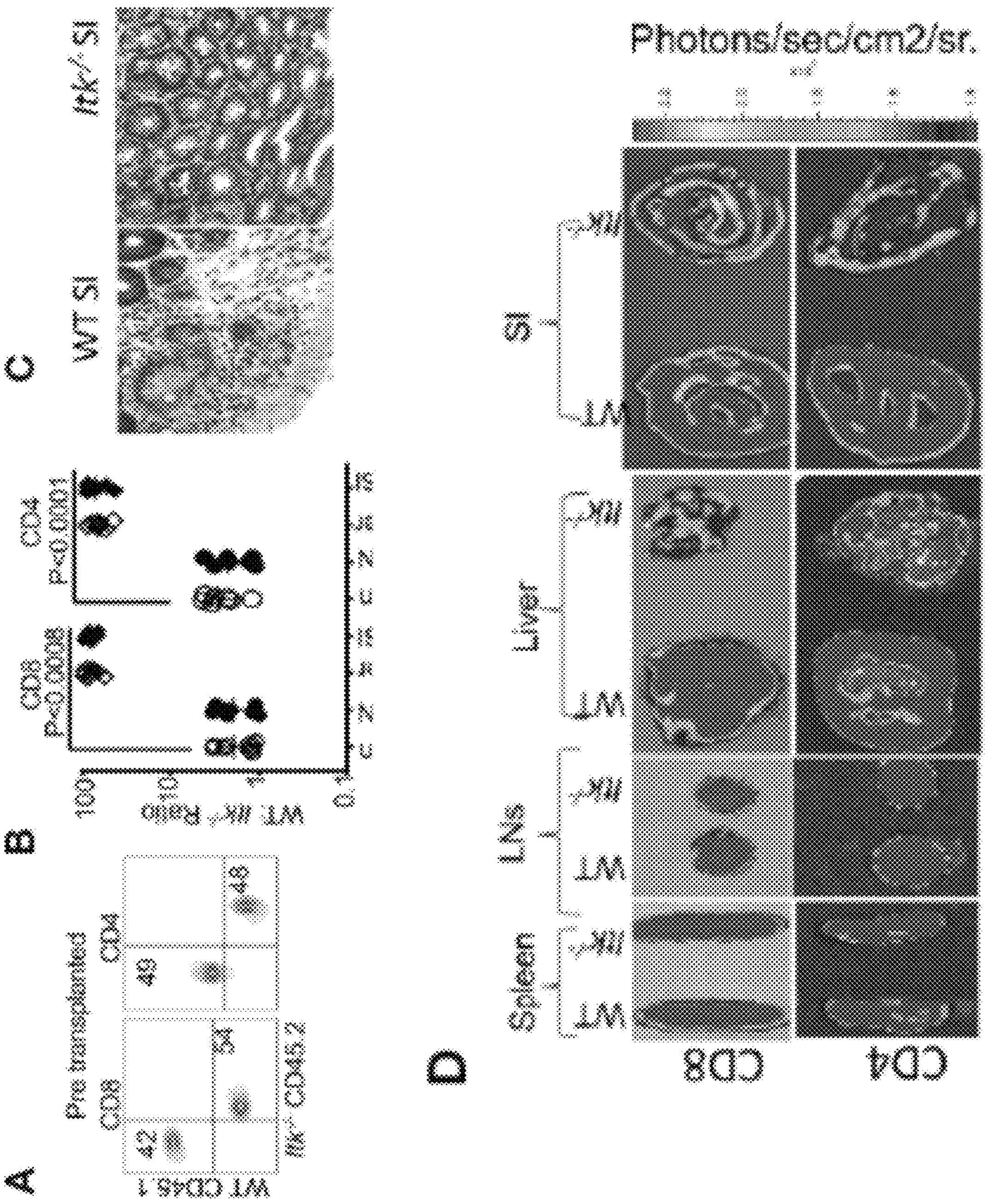
FIGS. 6A-6J depict ITK signaling is needed for T cell migration to the GVHD target tissues.

As an unbiased approach to further explore differences between WT and $Itk^{-/-}$ $CD8^+$ T cells, RNA sequencing analysis was employed to examine the differences in gene expression between WT and $Itk^{-/-}$ $CD8^+$ T cells following allo-HSCT. Donor WT and $Itk^{-/-}$ $CD8^+$ T cells were sort purified (using H-$2K^b$ antigen expressed by donor T cells) before and 7 days after they were transferred into irradiated BALB/c recipients, and RNA sequences was done. Although WT and $Itk^{-/-}$ $CD8^+$ T cells are distinct prior to transplantation due to the enhanced IMP in the absence of ITK, WT and $Itk^{-/-}$ T cells which homed to the spleen post-transplantation are similar as revealed by the fact that they clustered within a close proximity in the Principal Component Analyses (PCA) (FIG. 5A). It was problematic to collect enough cells from the intestine of the $Itk^{-/-}$ T cell recipients, since they are deficient in homing to the intestine (FIG. 6B-D). To further determine the differentially expressed genes that are unique in WT $CD8^+$ T cells and associated with their ability to home to the GVHD target organs, the lists of genes that were up- or down-regulated after the cells were transferred into the recipients and homed to different organs were compared. It was found that genes that are up- or down-regulated in $Itk^{-/-}$ T cells isolated from the spleens of the recipients ($Itk^{-/-}$ Spl), as compared to $Itk^{-/-}$ pre-transplanted cells ($Itk^{-/-}$-Pre), have minimal overlap with those that are differentially expressed in WT T cells homed to the gut (normalized to WT-Pre) (FIG. 5B-C). Genes that are differentially expressed in WT T cells that were able to home to the GVHD target organ may reveal signals that are deficient due to the absence of ITK. It was extracted the list of genes that are up- or down-regulated in only WT T cells isolated from the gut of the recipient's post-transplantation (FIG. 5D shows 23 up-regulated and FIG. 5D shows 27 down-regulated genes) (see also www.ncbi.nml.nih.gov/geo GSE161160). The differentially expressed genes between WT and $Itk^{-/-}$ donor T cells were enriched for transcripts encoding lymphocyte homing molecules such as adhesion molecules and chemokine signaling proteins, which might contribute to the defective homing capability of $Itk^{-/-}$ donor T cells (FIG. 5E). The results of critical genes that were differentially expressed were confirmed by q-RT-PCR (FIG. 5D). Using pathway enrichment analyses, the data also revealed a critical role for ITK in regulating genes involved in T cell cytokine/cytokine receptor interaction, cell adhesion, graft-versus-host disease, allograft rejection, and chemokine signaling pathways (FIG. 5E). These data suggest that ITK regulates the expression of signature genes associated with the homing of the transplanted cells into the GVHD targeted organs, while it does not have an apparent effect on T cell homing in the spleen. This may, in part, explain the ability of $Itk^{-/-}$ T cells to maintain GVL effects while being unable to home to the GVHD target organs and participate in GVHD.

More specifically, FIG. 5 depicts ITK differentially regulates gene expression in T cells during GVHD. WT and $Itk^{-/-}$ $CD8^+$ T cells were FACS sorted then transplanted into irradiated BALB/c mice. At day 7 post-transplant, donor T cells were sort-isolated (based on expression of H-$2K^b$, CD3 and CD8) from host spleen. Sorted donor T cells were subjected to RNA sequencing. FIG. 5A depicts principal component analysis of genes with ≥2-fold change in any pairs of group combinations, with false discovery rate (FDR)≤0.05. WT-Pre and $Itk^{-/-}$-Pre denotes cells prior to transfer, and WT-Spl, and $Itk^{-/-}$ Spl denotes cells isolated from the spleen (Spl) of the recipients post-transfer. (FIGS. 5B & FIG. 5C) Venn diagram of genes that are ≥2-fold up- or down-regulated in the indicated comparisons, with FDR (P)≤0.05. FIG. 5E depicts differentially expressed genes were enriched for pathway analysis comparing WT and $Itk^{-/-}$. FIG. 5D depicts WT and $Itk^{-/-}$ $CD8^+$ T cells were FACS sorted then transplanted into irradiated BALB/c mice. At day 7 post-transplant, donor T cells were sort-isolated (based on expression of H-$2K^b$, CD3 and CD8) from host spleen and small intestine (Gut). Total RNA was isolated from sorted donor T cells were and qPCR was performed.

ITK Signaling is Required for T Cell Migration to the GVHD Target Tissues.

Figures 6E, 6F, 6G, 6H, 6I, 6J:
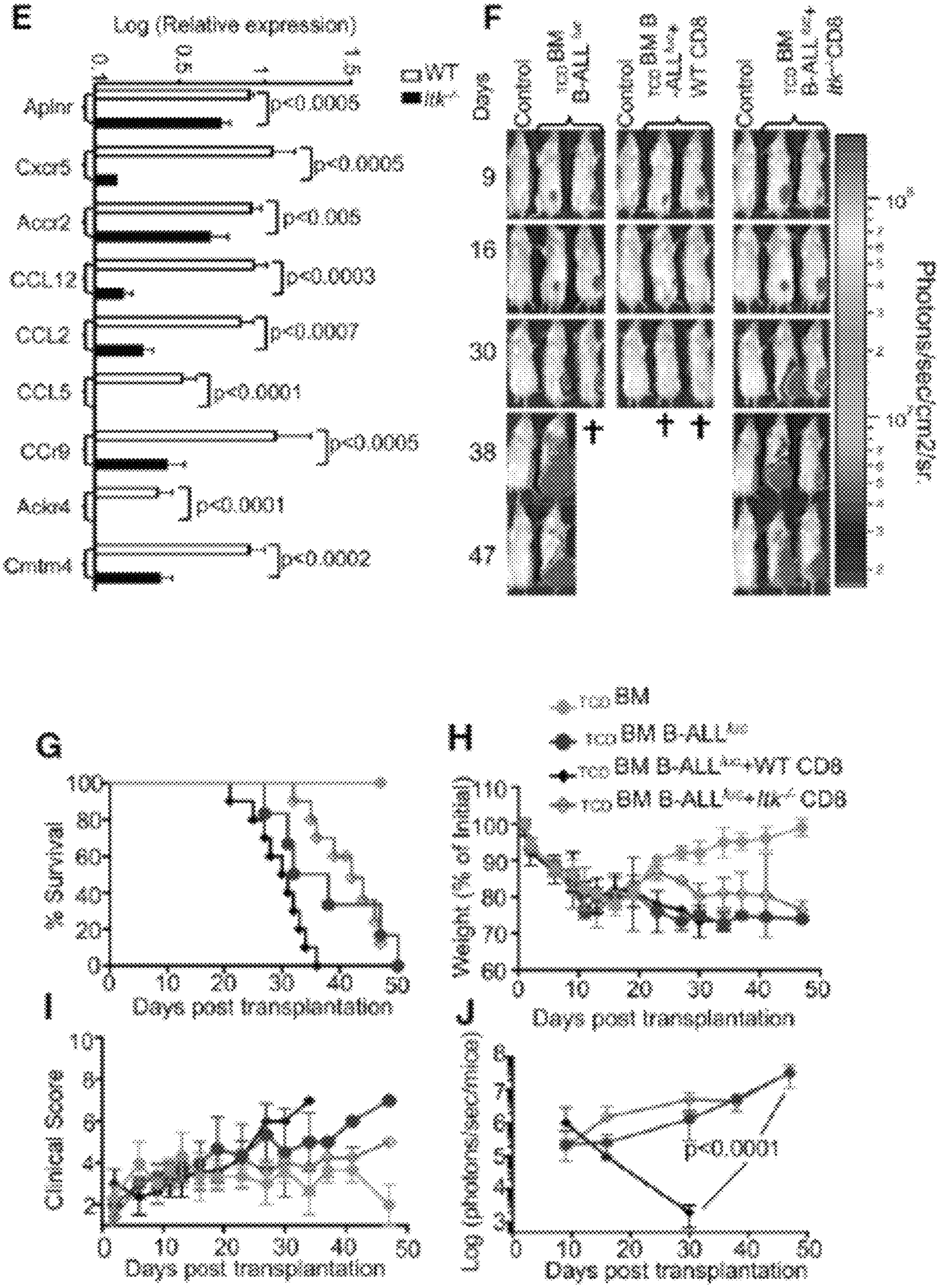

GVHD involves early migration of alloreactive T cells into the target organs, followed by T cell expansion and tissue destruction. Modulation of alloreactive T cell trafficking has been suggested to play a significant role in ameliorating experimental GVHD. (See e.g., Lu S X, et al. Absence of P-selectin in recipients of allogeneic bone marrow transplantation ameliorates experimental graft-versus-host disease. J Immunol (2010) 185:1912-9. doi: 10.4049/jimmunol.0903148). Therefore, the trafficking of donor T cells to GVHD target tissues was as previously described Lu S X, et al. Absence of P-selectin in recipients of allogeneic bone marrow transplantation ameliorates experimental graft-versus-host disease. *J Immunol* (2010) 185:1912-9. doi: 10.4049/jimmunol.0903148). Irradiated BALB/c recipient mice were injected with $CD8^+$ and $CD4^+$ T cells from $Itk^{-/-}$ ($CD45.2^+$) and WT B6LY5 ($CD45.1^+$) mice mixed at a 1:1 ratio (FIG. 6A), and at 7 days post transplantation, recipient mice were examined for the presence of donor $CD8^+$ and $CD4^+$ T cells in the spleen, lymph nodes, liver and the small intestines. While the WT:$Itk^{-/-}$ $CD8^+$ and $CD4^+$ T cell ratio remained ~1:1 in the spleen and lymph nodes (FIG. 6B), this ratio in the liver and small intestine was significantly elevated, suggesting that $Itk^{-/-}$ $CD8^+$ and $CD4^+$ T cells were defective in migration to and/or expansion in those tissues. Using histological staining for H&E, significant leukocyte infiltration into GVHD target organs was observed-liver, skin, and small intestine (SI) (See e.g., Negrin, R. S. & Contag, C. H. In vivo imaging using bioluminescence: a tool for probing graft-versus-host disease. *Nat Rev Immunol* 6, 484-490 (2006) in WT T cell recipients but not in $Itk^{-/-}$ T cell recipients (FIG. 6C). As an alternative approach, both $CD8^+$ and $CD4^+$ T cells were tracked in allo-BMT mice by using donor $CD8^+$ and $CD4^+$ T cells from WT and $Itk^{-/-}$ mice that also express luciferase, which could be monitored by bioluminescence. It was observed that both $CD8^+$ and $CD4^+$ donor T cells from $Itk^{-/-}$ mice had significantly impaired residency in GVHD target organs, including the liver and small intestine (SI), compared to WT, despite no differences in spleen and lymph nodes (FIG. 6D). In the mixed T cell transfer model, it was determined that $Itk^{-/-}$ T cell proliferation was comparable to that of WT cells; therefore, it is very likely that the reduced number of $Itk^{-/-}$ T cells in the liver and small intestine was due to impaired T cell trafficking. Pro-inflammatory conditioning treatment may promote T cell migration into GVHD target tissues (See e.g., Seif, F. et al. The role of JAK-STAT signaling pathway and its regulators in the fate of T helper cells. *Cell Commun Signal* 15, 23 (2017); and Choi, J. et al. IFNgammaR signaling mediates alloreactive T-cell trafficking and GVHD. *Blood* 120, 4093-4103 (2012)). Indeed, in the same mixed T cell transfer model, it was found that chemokine and chemokine receptor expression (Aplnr, Cxcr5, Accr2, CCL12, CCL2, CCL5, Ccr9, Ackr4, and Cmtm4) was also significantly reduced in $Itk^{-/-}$ $CD8^+$ and $CD4^+$ T cells at day 7 post-transplantation (FIG. 6E). These data suggest that $Itk^{-/-}$ $CD8^+$ T cells display attenuated chemokine receptor expression, which correlates with defective migration to GVHD target organs and reduced target organ pathology.

Given that $Itk^{-/-}$ T cells exhibit defective migration to target organs of GVHD, it was predicted that although $Itk^{-/-}$ T cells can clear leukemia cells in the blood and secondary lymphoid organs, they would not be able to kill leukemia cells that reside in tissues. To test this possibility, lethally irradiated BALB/c mice were BM-transplanted together with FACS-sorted WT or $Itk^{-/-}$ $CD8^+$ T cells, and challenged with subcutaneously injected B-All luc cells. Although $Itk^{-/-}$ $CD8^+$ T cells did not cause GVHD, the subcutaneously injected leukemia cells were cleared only in mice transplanted with WT $CD8^+$ T cells, and not in those given $Itk^{-/-}$ $CD8^+$ T cells (FIGS. 6F-J). Together, these data suggest that the ITK signaling in T cells can separate GVHD from GVL effects, but only for leukemia cells that reside in the circulation and in secondary lymphoid organs (such as hematologic malignancies).

More specifically, FIG. 6 depicts ITK signaling is required for T cell migration to the GVHD target tissues. FIG. 6A depicts irradiated BALB/c mice were allo-HSCT-transplanted and injected with FACS-sorted WT and $Itk^{-/-}$ $CD8^+$ T and $CD4^+$ T cells mixed at a 1:1 ratio. FACS analysis of sorted T cells pre-transplant shown. FIG. 6B depicts at day 7 post-BMT, the spleen, liver, and small intestine (SI) were examined for donor WT and $Itk^{-/-}$ T cells. The ratio of WT:$Itk^{-/-}$ $CD8^+$ and $CD4^+$ T cells in the organs was determined. FIG. 6C depicts at day 7 post-allo-HSCT, small intestines were examined by H&E staining. FIG. 6D depicts irradiated BALB/c mice were BM-transplanted and injected with $CD8^+$ T $CD4^+$ T cells from luciferase-expressing WT or $Itk^{-/-}$ mice. FIG. 6E depicts on Day 7 post-allo-HSCT, donor T cells were isolated and examined for the expression of Aplnr, Cxcr5, Accr2, CCL12, CCL2, CCL5, CCr9, Ackr4, and Cmtm4 using q-RTPCR. P values were calculated using 2-way ANOVA and Student's t test, p values are listed. FIG. 6F depicts irradiated BALB/c mice were transplanted with C57Bl/6-derived BM and FACS-sorted WT or $Itk^{-/-}$ $1\times10^6$ $CD8^+$ T cells, and challenged subcutaneously with $2\times10^5$ luciferase-expressing B-All luc cells. Recipient animals were monitored for weight changes. Group one of recipient mice was transplanted with $10\times10^6$ T cell-depleted bone marrow ($_{TCD}$BM). The second group of recipient mice was transplanted with $10\times10^6$ T cell-depleted bone marrow and $2\times10^5$ primary B-ALL luc+ cells ($_{TCD}$BM+B-ALL$^{luc}$). The third group of recipient mice was transplanted with $10\times10^6$ T cell-depleted bone marrow along with $1\times10^6$ T cell from WT mice along with $2\times10^5$ B-ALL-luc+ cells ($_{TCD}$BM+B-ALL$^{luc}$+WT CD8). The fourth group of recipient mice was transplanted with $10\times10^6$ T cell-depleted bone marrow and $1\times10^6$ T cell from $Itk^{-/-}$ mice along with $2\times10^5$ B-ALL-luc+ cells. ($_{TCD}$BM+B-ALL$^{luc}$+$Itk^{-/-}$ CD8). Representative bioluminescence images of leukemia cell-bearing mice on days 9, 16, 30, 38, and 47 are shown. Note: Controls are naïve mice used as negative control for bioluminescence (BLI). FIG. 6G depicts animals were monitored for survival over 47 days, FIG. 6H depicts changes in weight loss, FIG. 6I and for clinical score. FIG. 6J depicts recipient mice were monitored for leukemia cell growth using the IVIS imaging system and quantified data is shown. For weight changes and leukemia cell growth, one representative of 2 independent experiments is shown (n=3 mice/group for control, n=5 mice for WT, and n=5 mice for $Itk^{-/-}$). Survival groups were combined from both experiments. P values were calculated using two-way ANOVA and Student's t test, p values are listed.

Figures 11A, 11B:
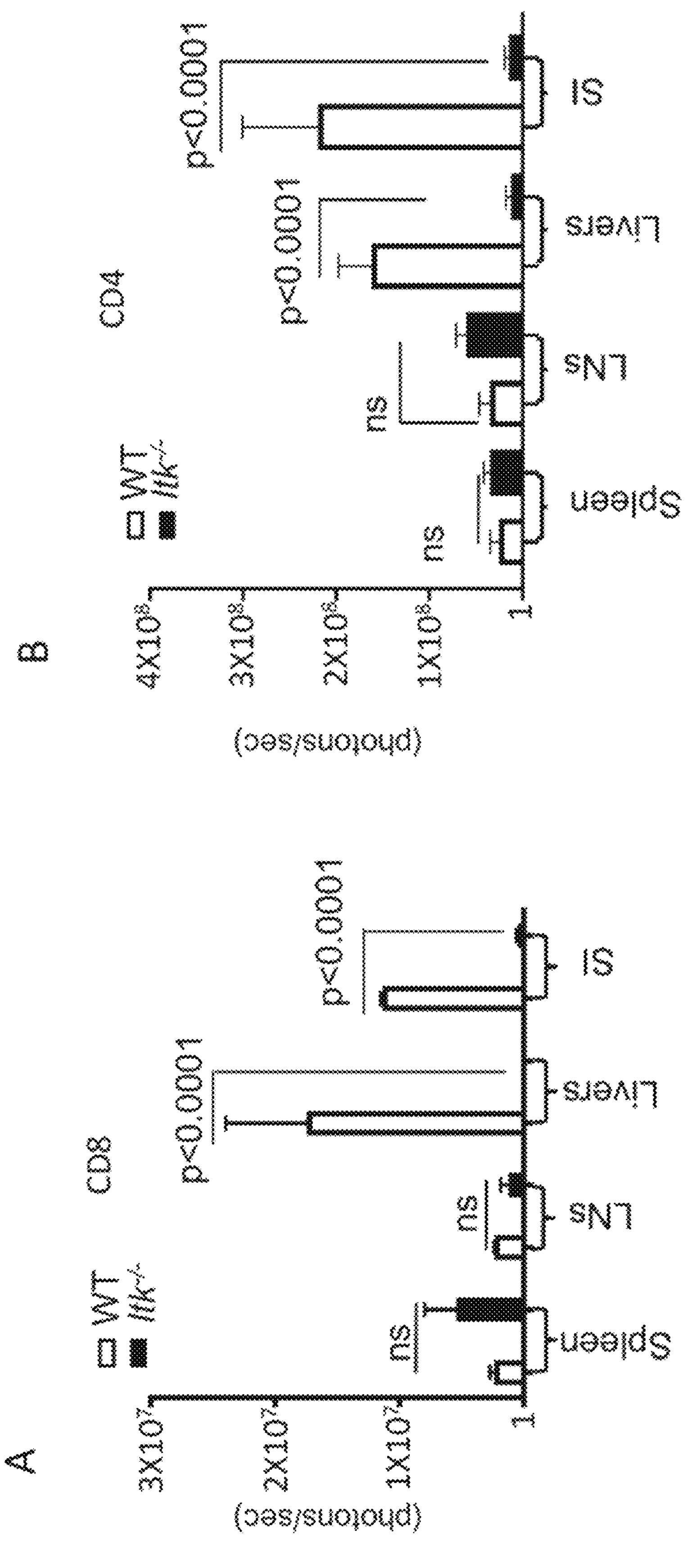
FIGS. 11A and 11B depict quantitative analysis of tissue BLI.

More specifically, FIGS. 11A and 11B depict quantitative analysis of tissue BLI. For tissue imaging experiments, allo-HSCT was performed with $10\times10^6$ WT T cell-depleted BM cells and $1\times10^6$ FACS-sorted $CD8^+$ T cells or $CD4^+$ T cells (from B6-luc or $Itk^{-/-}$ luc mice) and bioluminescence imaging of tissues was performed as previously described. (See. e.g., Beilhack, A. et al. In vivo analyses of early events in acute graft-versus-host disease reveal sequential infiltration of T-cell subsets. *Blood* 106, 1113-1122 (2005). Briefly, 5 minutes after injection with luciferin (10 μg/g body weight), selected tissues were prepared and imaged for 1 minutes. Imaging data were analyzed and quantified with Living Image Software (Xenogen) and Igor Pro (Wave Metrics, Lake Oswego, OR).

DISCUSSION

In this example, it has been demonstrated that the absence of the TCR-regulated kinase ITK significantly suppresses GVHD, while maintaining the GVL effect in models of allo-HSCT. Loss of ITK also altered expression of IRF4, and the JAK/STAT pathway components JAK1, JAK2, and STAT, which play critical roles in controlling cytokine expression. See e.g., Malemud C J. The role of the JAK/STAT signal pathway in rheumatoid arthritis, Ther Adv Musculoskelet Dis (2018) 10:117-27. doi: 10.1177/1759720X18776224, and Seif F, Khoshmirsafa M, Aazami H, Mohsenzadegan M, Sedighi G, BaharM. The role of JAK-STAT signaling pathway and its regulators in the fate of T helper cells. Cell Commun *Signal* (2017) 15:23. doi: 10.1186/s12964-017-0177-y. Transcriptome analysis by RNA sequencing revealed that ITK signaling controls chemokine receptor expression during this process, which in turn affects the ability of donor T cells to migrate to GVHD target organs. Taken together, these data suggest that ITK could represent a potential target for the separation of GVHD and GVL responses after allo-HSCT.

The ability of T cells from $Itk^{-/-}$ mice to induce GVL without causing GVHD indicates that the ITK signaling pathway is involved in the pathogenesis of GVHD. $Itk^{-/-}$ T cells develop into IMP cells ($CD122^+$ $CD44^{hi}$ phenotype) in the thymus, and it is possible that such cells are responsible for the GVHD and GVL effects observed. In experiments where WT T cells developed into IMPs, it was found that they retained the capacity to induce both acute GVHD and GVL, suggesting a T cell-intrinsic function of ITK in promoting GVHD during allo-HSCT. Similarly, the cytotoxicity of $Itk^{-/-}$ $CD8^+$ T cells is not dependent on the IMP. While IMP cells express significantly higher Eomes compared to their WT non-IMP counterparts, it was found that IMP $CD8^+$ T cells are not responsible for distinguishing GVHD and GVL. Surprisingly it was noted that $Itk^{-/-}$ $CD8^+$ T cells exhibit similar or higher in vitro cytotoxicity compared to WT $CD8^+$ T cells. This may be due to the higher levels of perforin expressed by $Itk^{-/-}$ T cells compared to WT T cells.

The data also show that $Itk^{-/-}$ donor $CD4^+$ and $CD8^+$ T cells exhibit reduced expression of chemokine receptors compared to WT counterparts. Moreover, the migration of Itk/donor T cells to target organs was also severely defective, reflecting the reduced expression of key chemokine receptors. The defective migration of $Itk^{-/-}$ $CD8^+$ and $CD4^+$ T cells likely contributes to the attenuation of GVHD, since these T cells continue to display GVL effects against leukemia cells that were injected intravenously and reside in secondary lymphoid organs. In contrast, WT but not $Itk^{-/-}$ $CD8^+$ T cells were able to inhibit leukemia cell growth when the leukemia cells were injected subcutaneously. The compartmentalization of T cells to secondary lymphoid organs can be an effective strategy for preventing GVHD, while leaving GVL effects against hematologic malignancies intact. Previously published work showed that IFN-γR signaling constitutes a major mechanism for donor T cell migration to GVHD target organs (See e.g., Choi J, Ziga E D, Ritchey J, Collins L, Prior J L, Cooper M L, et al. IFNgammaR signaling mediates alloreactive T-cell trafficking and GVHD. Blood (2012) 120:4093-103. doi: 10.1182/blood-2012-01-403196; and Choi J, Cooper M L, Alahmari B, Ritchey J, Collins L, Holt M, et al. Pharmacologic blockade of JAK1/JAK2 reduces GvHD and preserves the graft-versus-leukemia effect. PloS One (2014) 9: e109799. doi: 10.1371/journal.pone.0109799), and it was observed that the lack of ITK affects production of IFN-γ. The retention of T cells to secondary lymphoid organs by FTY720-mediated inhibition of S1P1 also ameliorates GVHD while maintaining GVL effects (See e.g., Villarroel V A, Okiyama N, Tsuji G, Linton J T, Katz S I. CXCR3-mediated skin homing of autoreactive CD8 T cells is a key determinant inmurine graft-versushost disease. J Invest Dermatol (2014) 134:1552-60. doi: 10.1038/jid.2014.2; and Liu W, Ren H-Y, Dong Y-J, Wang L-H, Yin Y, Li Y, et al. Bortezomib regulates the chemotactic characteristics of T cells through downregulation of CXCR3/CXCL9 expression and induction of apoptosis. Int J Hematol (2012) 96:764-72. doi: 10.1007/s12185-012-1195-6).

Similarly, inhibition of T cell migration to GVHD target organs by targeting the chemokine receptors CCR2 or CCR5 protects against GVHD-induced pathology (See e.g., Murai M, Yoneyama H, Ezaki T, Suematsu M, Terashima Y, Harada A, et al. Peyer's patch is the essential site in initiating murine acute and lethal graftversus-host reaction. Nat Immunol (2003) 4:154-60. doi: 10.1038/ni879; and Terwey T H, Kim T D, Kochman A A, Hubbard V M, Lu S, Zakrzewski J L, et al. CCR2 is required for CD8-induced graft-versus-host disease. Blood (2005) 106:3322-30. doi: 10.1182/blood-2005-05-1860), which at least with CCR2 deficiency was shown to preserve the GVL effect. Importantly, in a clinical study, CCR5 blockade by a small molecule antagonist led to a reduction in GVHD with no significant difference in relapse rates, suggesting that blocking T cell migration to target tissues could reduce GVHD severity without compromising the beneficial GVL effect (See e.g., Terwey T H, Kim T D, Kochman A A, Hubbard V M, Lu S, Zakrzewski J L, et al. CCR2 is required for CD8-induced graft-versus-host disease. Blood (2005)). In addition, the inhibition of CXCR3 ameliorates GVHD in allo-HSCT mice. Activated alloreactive $CD8^+$ T cells upregulate the expression of CX3CR1 and CXCR6 after allo-HSCT (See e.g., Duffner U, Luc B, HildebrandtGC, Teshima T, WilliamsDL, Reddy P, et al. Role of CXCR3-induced donor T-cell migration in acute GVHD. ExpHematol (2003) 31:897-902. doi: 10.1016/S0301-472X (03) 00198-X; and Vadakekolathu J, Rutella S. T-Cell Manipulation Strategies to Prevent Graft-Versus-Host Disease in Haploidentical Stem Cell Transplantation. Biomedicines (2017) 5 (2): 33. doi: 10.3390/biomedicines5020033), and these receptors are important for the homing of $CD8^+$ T cells to the liver and intestines. Thus, CXCR6 deficiency or blockade of the CXCR3 and CXCR6 ligands attenuates GVHD (See e.g, Duffner U, Luc B, HildebrandtGC, Teshima T, Williams D L, Reddy P, et al. Role of CXCR3-induced donor T-cell migration in acute GVHD. ExpHematol (2003) 31:897-902. doi: 10.1016/S0301-472X (03) 00198-X. Importantly, the GVL effect is still maintained under these conditions (see e.g., Sato T, Thorlacius H, Johnston B, Staton T L, Xiang W, Littman D R, et al. Role for CXCR6 in recruitment of activated CD8+ lymphocytes to inflamed liver. J Immunol (2005) 174:277-83. doi: 10.4049/jimmunol. 174.1.277). Thus, blocking T cell migration by chemokine receptor blockade could be beneficial in the treatment of GVHD after allo-HSCT. Since activated $Itk^{-/-}$ T cells displayed significantly reduced expression of chemokine receptors, the compartmentalization of $CD8^+$ T cells to secondary lymphoid organs likely contributes to the preservation of GVL effects while severely attenuating GVHD (see e.g., Vadakekolathu J, Rutella S. T-Cell Manipulation Strategies to Prevent Graft-Versus-Host Disease in Haploidentical Stem Cell Transplantation. Biomedicines (2017) 5 (2): 33. doi: 10.3390/biomedicines5020033). Although suppression of TCR signaling can prevent GVHD, the complete suppression of T cell responses negates the beneficial GVL effect that is also provided by the same donor T cells after allo-HSCT (See e.g., Vaeth M, Bäuerlein C A, Pusch T, Findeis J, Chopra M, Mottok A, et al. Selective NFAT targeting in T cells ameliorates GvHD while maintaining antitumor activity. Proc Natl Acad Sci USA (2015) 112:1125-30. doi: 10.1073/pnas.1409290112). The fact that mice transplanted with $Itk^{-/-}$ T cells are able to mount GVL responses is an exciting feature. The preservation of the GVL response could have occurred for several reasons. First, the proliferation and cytotoxic activity of $Itk^{-/-}$ T cells is preserved compared to pro-inflammatory cytokine production. The manifestations and severity of GVHD are highly influenced by local cytokines, which then activate transcription factors and drive development toward a cytokine storm. In addition, proinflammatory cytokines exert direct effects on GVHD target tissues (See e.g., Hill G R, Crawford J M, Cooke K R, Brinson Y S, Pan L, Ferrara J L M. Total body irradiation and acute graft-versus-host disease: the role of gastrointestinal damage and inflammatory cytokines. Blood (1997) 90:3204-13. doi: 10.1182/blood.V90.8.3204; and Mohty M, Blaise D, Faucher C, Vey N, Bouabdallah R, Stoppa A M, et al. Inflammatory cytokines and acute graft-versus-host disease after reducedintensity conditioning allogeneic stem cell transplantation. Blood (2005) 106:4407-11. doi: 10.1182/blood-2005-07-2919; and Holler E. Cytokines, viruses, and graft-versus-host disease. Curr Opin, Hematol (2002) 9:479-84. doi: 10.1097/00062752-200211000-00002).

Indeed, the presence of cytokine storm is considered one of the hallmarks of GVHD pathogenesis (See e.g., Ju X P, Xu B, Xiao Z P, Li J Y, Chen L, Lu S Q, et al. Cytokine expression during acute graft-versus-host disease after allogeneic peripheral stem cell transplantation. Bone Marrow Transplant (2005) 35:1179-86. doi: 10.1038/ sj.bmt.1704972), and the data showed that cytokine production was significantly reduced in mice that received $Itk^{-/-}$ T cells. It was also confirmed that cytokine production is T cell-intrinsic while proliferation is T cell-extrinsic. To explore the potential mechanism of this observed difference in cytokine and chemokine receptor expression between WT and $Itk^{-/-}$ donor $CD4^+$ and $CD8^+$ T cells, key transcription factors and pathways were analyzed that may be involved in these processes. Significant differences in expression of the transcription factor IRF4 and the JAK/STAT signaling pathways were found, which regulate the expression of key molecules required for the maintenance of T cell effector function, cytokine production, and chemokine receptor upregulation. Since IRF4 has been shown to play critical roles in modulating TCR signal strength and T cell function (See e.g., Biswas P S, Gupta S, Chang E, Song L, Stirzaker R A, Liao J K, et al. Phosphorylation of IRF4 by ROCK2 regulates IL-17 and IL-21 production and the development of autoimmunity in mice. J Clin Invest (2010) 120:3280-95. doi: 10.1172/JCI42856), it is likely that reduction in the activation of IRF4 and of the JAK/STAT pathway contribute to reduced cytokine expression, thus alleviating the cytokine storm in GVHD (15). The data shows that the reduced proliferation seen in donor T cells from $Itk^{-/-}$ mice is cell-extrinsic. ITK deficiency has been shown previously to affect T cell proliferation (See e.g., Ju X P, Xu B, Xiao Z P, Li J Y, Chen L, Lu S Q, et al. Cytokine expression during acute graft-versus-host disease after allogeneic peripheral stem cell transplantation. Bone Marrow Transplant (2005) 35:1179-86. doi: 10.1038/sj.bmt. 1704972) and cytokine production, but during allogenic activation, ITK-deficient T cells can still proliferate. This might be due to the redundant function of ITK and other Tec kinases (See e.g., Murali-Krishna K, Ahmed R. Cutting edge: naive T cells masquerading as memory cells. J Immunol (2000) 165:1733-7. doi: 10.4049/jimmunol.165.4.1733). This finding is in line with cytokine data, which show that $Itk^{-/-}$ T cells produce less cytokines, both in serum and on a per-cell basis. When transplanting either $CD4^+$ or $CD8^+$ T cells in a 1:1 ratio of WT:$Itk^{-/-}$ cells, similar levels of proliferation for both WT and $Itk^{-/-}$ donor cells was observed. The data therefore provide further evidence that donor T cell proliferation is influenced by inflammatory conditions (See e.g., Schaeffer E M, Debnath J, Yap G, McVicar D, Liao X C, Littman D R, et al. Requirement for Tec kinases RIk and Itk in T cell receptor signaling and immunity. Science (1999) 284:638-41. doi: 10.1126/science.284.5414.638)).

All together the data show that attenuating TCR signaling reduces donor T cell-mediated cytokine production, resulting in less severe GVHD. In addition, the inability of T cells to migrate to target organs may also affect this process, and thus explains the reduced ability of the $Itk^{-/-}$ donor T cells to induce GVHD.

Highlights of Example 1 include: 1) ITK-deficient donor T cells exhibit minimal GVHD, but maintain GVL activity; 2) ITK-deficient donor T cells exhibit significantly reduced production of inflammatory cytokines and migration to GVHD target organs; and 3) Eomesodermin (Eomes) is shown for the GVL effect. (See e.g., Targeting Interleukin-2-Inducible T Cell Kinase (ITK) Differentiates GVL and GVHD in Allo-HSCT, to Karimi et al., Frontiers in Immunology, Nov. 26, 2020, doi: 10.3389/fimmu.2020.593863 (herein entirely incorporated by reference).

EXAMPLE II Targeting SLP76: ITK Interaction Separates GVHD from GVL in Allo-HSCT

Summary

Allogeneic hematopoietic stem cell transplantation (allo-HSCT) is a curative therapy for hematological malignancies, due to graft-versus-leukemia (GVL) activity mediated by alloreactive donor T cells. However, graft-versus-host disease (GVHD) is also mediated by these cells. Here, the effect of attenuating TCR-mediated SLP76: ITK interaction in GVL vs. GVHD effects was assessed after allo-HSCT. $CD8^+$ and $CD4^+$ donor T cells from mice expressing a Y145F mutation in SLP-76 did not cause GVHD, but preserved GVL effects against B-ALL cells. SLP76Y145FKI $CD8^+$ and $CD4^+$ donor T cells also showed less inflammatory cytokine production and migration to GVHD target organs. A novel peptide has been developed to specifically inhibit SLP76: ITK interactions, resulting in decreased phosphorylation of PLCγ1 and ERK, decreased cytokine production in human T cells, and separation of GVHD from GVL effects. Altogether, the data suggest that inhibiting SLP76: ITK interaction is a therapeutic strategy to separate GVHD from GVL effects after allo-HSCT treatment. (See e.g., Targeting SLP76: ITK interaction separates GVHD from GVL in allo-HSCT, iScience 24, 102286, 2021 to Karimi et al. herein entirely incorporated by reference).

Transparent Methods

Mice: SLP76 Y145FKI mice were a kind gift of Dr. Martha S. Jordan (University of Pennsylvania) (Jordan et al., 2008). ROSA26-pCAGGs-LSL-Luciferase, Thy1.1 (B6.PL-Thy1a/CyJ), CD45.1 (B6.SJL-$Ptprc^a$ $Pepc^b$/BoyJ) and BALB/c mice were purchased from Charles River or Jackson Laboratory. $Eomes^{flox/flox}$, B6.129S1, and CD4cre mice were purchased from Jackson Laboratory. Mice expressing Cre driven by the CMV promoter (CMV-Cre) were purchased from the Jackson Laboratory and crossed to ROSA26-pCAGGs-LSL-Luciferase mice (B6-luc). B6-luc mice were bred with SLP76 Y145FKI mice to create SLP76 Y145FKI luc mice. Mice aged 8-12 weeks were used, and all experiments were performed with age and sex-matched mice. Animal maintenance and experimentation were performed in accordance with the rules and guidelines set by the institutional animal care and use committees at SUNY Upstate Medical University.

Reagents, cell lines, flow cytometry: Most monoclonal antibodies for flow cytometric analysis were purchased either from eBiosciences (San Diego, CA) or Biolegend (San Diego, CA). For TCR mediated activation, we used anti-CD3 and anti-CD28. For flow cytometry analysis, we used mouse antibodies anti-CD3-FITC, anti-CD8-FITC, anti-CD4-PE anti-BrdU-APC, anti-IFN-γ-APC, anti-TNF-α-PE, anti-CD122-APC, anti-CD25-BV421, and anti-FoxP3-APC. Mice migration studies we used anti CD45.1 APC, anti-CD45.2-PE, H2 KB PerCP. Anti-CD44 Pacific Blue, anti-CD122 APC and anti-Eomes PE. Human antibodies: anti-CD3-APC, anti-CD4-PE, anti-CD8-Pacific Blue, anti-TNF-α-Pe/Cy7, anti-IFN-γ-APC/Cy7. For serum ELISAs, we used Biolegend LEGENDplex kits, some of which were custom ordered to detect both mouse and human cytokines. For bioluminescent imaging, luciferin was purchased from Gold Bio (St Louis, MO). To exclude dead cells from analyses, we used LIVE/DEAD Fixable Aqua Dead Cell staining. All flow cytometry was performed on a BD LSR Fortessa flow cytometer (BD Biosciences). Flow data were analyzed with FlowJo software (Tree Star, Ashland, OR). T cells were purified with anti-CD8 or anti-CD4 magnetic beads using MACS columns (Miltenyi Biotec, Auburn, CA). Cells were sorted with a FACS Aria cell sorter (BD Biosciences). FACS-sorted cells showed >95% purity. For signaling analysis, antibodies against for both human and mouse ITK, PLCg1, ERK, GAPDH, AKT, PI3K and β-Actin (total and/or phosphoproteins) were purchased from Cell Signaling Technology (Danvers, MA). Cells culturing reagents were purchased from Invitrogen (Grand Island, NY) and Sigma-Aldrich (St. Louis, MO), unless otherwise specified. Primary mouse B-cell acute lymphoblastic leukemia (B-ALL) blasts and primary cells (Cheng et al., 2016) were transduced with luciferase, and cultured as described previously (Edinger et al., 2003). B-ALL was chosen for this model because (1) these cells are syngeneic with BALB/c mice and allogeneic to C57BI/6 mice, and (2) B-ALL was selected to be more related to human disease (Cheng et al., 2016).

GVHD and GVL studies: Recipient BALB/c mice (MHC haplotype d) as recipients were lethally irradiated with 800 cGy total in two split doses of 400cGy. Bone marrow cells were harvested from mouse legs, and total bone marrow cells were incubated with CD90.2 beads, using 100 ul of beads per mouse according to manufacturer protocols. NK cells were depleted and by DX5 beads, and CD122+ cells with anti PE beads. Recipient mice were injected intravenously with $10\times10^6$ T cell-depleted bone marrow ($_{TCD}$BM) cells, with or without donor T cells, either $1\times10^6$ or $2\times10^6$ FACS-sorted $CD8^+$, $CD4^+$ T cells, or $CD8^+$ and $CD4^+$ cells mixed at a 1:1 ratio from WT or SLP76 Y145FKI mice. For GVL experiments, primary B cell acute lymphoblastic leukemia (B-ALL, syngeneic to BALB/c and allogeneic to C57BI/6) blasts were transduced with luciferase as described previously (Cheng et al., 2016), and $2\times10^5$ luciferase-expressing B-ALL-luc cells were used per recipient mouse unless otherwise specified. All recipient animals were examined for tumor burden twice a week from the time of challenge with B-ALL luc injection until 70 days post-transplant, using bioluminescence imaging with the IVIS 50 and IVIS 200 imaging systems (Xenogen) as previously described (Contag and Bachmann, 2002). Each mouse was injected with 10 μg/g body weight of luciferin and imaged for 1 minute. The bioluminescence data were analyzed and quantified with Living Image Software (Xenogen) and Igor Pro (Wave Metrics, Lake Oswego, OR). Recipient animals were evaluated for clinical score 2-3 times per week by a scoring system that sums changes in 6 clinical parameters: (1) weight loss, (2) posture, (3) activity, (4) fur texture, (5) diarrhea and (6) skin integrity (Cooke et al., 1996). Animals which lost ≥30% of their initial body weight were euthanized.

Cytokine production assays: Animals were lethally irradiated and transplanted with donor T cells as described above. On Day 7 post-transplantation, serum was isolated from recipient mice to examine cytokines in circulation. Serum was examined for IL-33, IL-1a, IFN-g, TNF-a and IL-17A by multiplex cytokine assays (Biolegend LEGENDplex). For restimulation, splenocytes were processed to obtain single cells, and T cells were stimulated with anti-CD3 and anti-CD28 for 6 hours in the presence of brefeldin A (10 mM). After 6 hours, stimulated cells were stained for surface markers and stained intracellularly for cytokines (IFN-g and TNF-a). As a control, T cells from the same spleen were stimulated with PMA and ionomycin in the presence of brefeldin A.

Proliferation Assays: For detection of BrdU, transplanted mice (as described above) were given BrdU with an initial bolus of BrdU (2 mg per 200 μl intraperitoneally) and drinking water containing BrdU (1 mg/ml) for 2 days. BrDU incorporation was performed using a BrDU kit (Invitrogen) according to the manufacturer's instructions.

Cytotoxicity assays: For cytotoxicity assays, luciferase-expressing A20 and B-ALL cells (both allogenic to BALB/c) were seeded in 96-well flat bottom plates at a concentration of $3\times10^5$ cells/ml. D-firefly luciferin potassium salt (75 mg/ml; Caliper Hopkinton, MA) was added to each well and bioluminescence was measured with the IVIS 50 Imaging System. Subsequently, ex vivo effector cells (MACS-sorted or FACS-sorted $CD8^+$ T cells from bone marrow-transplanted mice) were added at 40:1, 20:1, and 10:1 effector-to-target (E:T) ratios and incubated at 37° C. for 4 hours. Bioluminescence in relative luciferase units (RLU) was then measured for 1 minute. Cells treated with 1% Nonidet P-40 were used as a measure of maximal killing. Target cells incubated without effector cells were used to measure spontaneous death. Triplicate wells were averaged and percent lysis was calculated from the data using the following equation: % specific lysis=100×(spontaneous death RLU-test RLU)/(spontaneous death RLU-maximal killing RLU) (Karimi et al., 2014).

Tissue Imaging: Allo-HSCT was performed with $10\times10^6$ WT T cell-depleted BM cells and $1\times10^6$ FACS-sorted $CD8^+$ or $1\times10^6$ FACS-sorted $CD4^+$ T cells (from B6-luc or SLP76Y145FKI luc mice) and bioluminescence imaging of tissues was performed as previously described (Beilhack et al., 2005). Briefly, 5 minutes after injection with luciferin (10 μg/g body weight), selected tissues were prepared and imaged for 5 minutes. Imaging data were analyzed and quantified with Living Image Software (Xenogen) and Igor Pro (Wave Metrics, Lake Oswego, OR).

Migration assays: Lethally irradiated BALB/c mice were injected intravenously with $10\times10^6$ WT $_{TCD}$BM cells from B6.PL-Thy1$^a$/CyJ mice, along with FACS-sorted $CD8^+$ or $CD4^+$ T cells from B6.SJL (Ly5 CD45.1) and SLP76Y145FKI (C57B16 background CD45.2) mice, mixed at a 1:1 (WT: SLP76Y145FKI) ratio. Seven days post-transplantation, the mice were sacrificed and lymphocytes from the liver, small intestine, spleen, and skin-draining lymph nodes were isolated. Livers were perfused with PBS, dissociated, and filtered with a 70 mm filter. The small intestines were washed in media, shaken in strip buffer at 37° C. for 30 minutes to remove the epithelial cells, and then washed, before digesting with collagenase D (100 mg/ml) and DNase (1 mg/ml) for 30 minutes in 37° C., and followed by filtering with a 70 mm filter. Lymphocytes from the liver and intestines were further enriched using a 40% Percoll gradient. The cells were analyzed for $CD8^+$ T cells and $CD4^+$ T cells and presence of H2K$^b$, CD45.1$^+$ and CD45.2$^+$ (to identify the transferred T cell populations) by flow cytometry, but we excluded any bone marrow-derived T cells (Thy1.1$^+$).

Western blotting: For protein analysis, T cells were either nonstimulated, or stimulated with anti-CD3 and anti-CD28 for 24 hours overnight, and were lysed with freshly prepared lysis buffer (RIPA Buffer (Fisher Scientific cat #PI89900)+cOmplete Protease Inhibitor Cocktail (Sigma-Aldrich; cat #11697498001)) and centrifuged for 10 minutes at 14000 rpm at 4° C. Protein aliquots of 70 μg of protein were loaded on a 12-18% denaturing polyacrylamide gel and transferred to nitrocellulose membranes for immunoblot analysis using antibodies specific to proteins of interest.

qPCR assay: Post-transplanted donor $CD8^+$ and $CD4^+$ T cells from C57BI/6 mice (MHC haplotype b) were FACS sorted from recipient mice on H2K$^b$ markers, and total RNA was isolated from T cells using the RNeasy kit from Qiagen (Germantown, MD). cDNA was made from total RNA using a cDNA synthesis kit (Invitrogen). qPCR assay was performed with a premade customized plate (CXCr3, CX3r1, CXCr1, CCR12, s1pR1, CrTAM, CXCR6, CCR9, CXCR5, CXCr4) (Fisher Scientific, Hampton, NH).

SLP76pTYR Peptide: To generate a molecule that specifically inhibits the interaction between pY145 of SLP76 and the SH2 domain of ITK, a peptide was designed based on the amino acid sequence of SLP76 from N132 to A155, which contains a phosphorylated tyrosine residue at Y145 (FIG. 17). To ensure that the peptide easily enters cells and that its cellular localization can be monitored, a C-terminal TAT peptide (GRKKRRQRRRPQ) (SEQ ID NO:3) and an N-terminal fluorescent FITC dye were incorporated, respectively, and named it SLP76pTYR peptide (FIG. Both-17). SLP76pTYR peptide (FITC Dye $^{132}$NEEEEAPVEDDADpYEPPPSNDEEA$^{155}$-TAT) (SEQ ID NO:5) and non-specific control peptide (FITC Dye-IIMTTTTNNKKSSRRVVVVAAAADD-TAT) (SEQ ID NO:6) were synthesized by Genscript Inc (Piscataway, NJ). These peptides were initially dissolved in 3% ammonia water to a final concentration of 10 mg/mL and then further diluted into PBS to a final concentration of 0.1 mg/mL. Fresh splenocytes were isolated from WT mice, and T cells were generated from splenocytes as previously described (Baker et al., 2001). Briefly, T cells were isolated from splenocytes using MACS beads (Miltenyi Biotec), then cultured in complete RPMI media ($3\times10^6$ cells/mL) and plated on anti-CD3 (2.5 mg/ml; Biolegend; cat #100202) and anti-CD28 (2.5 mg/ml; Biolegend; cat #102116) antibody-coated tissue culture plates until otherwise specified. T cells were incubated with SLP76pTYR, control peptide or vehicle alone at different concentrations ranging from 100 ng/ml to 1 mg/ml in the presence of 4 mg/ml of protamine sulfate. Protamine sulfate significantly increased peptide delivery into primary cells. Within 60 minutes, it was observed that peptides were inside the cells. Cells were cultured for 5 minutes prior to investigating signaling changes. Cells were examined for the presence of FITC by microscopy using a Leica DMi8 microscope equipped with an infinity total internal reflection fluorescence (TIRF) and DIC modules, a Lumencor SOLA SE II light box, a 150 mW 488 (GFP) laser and filter cube, a 100x/1.47 NA objective, and an Andor iXon Life 897 EMCCD camera. FITC expression was confirmed by flow cytometry as well. Cells were lysed and used in Western blots.

Human Samples: According to our IRB protocol (1140566-4), blood samples were obtained by vein puncture, and T cells were isolated from peripheral blood mononuclear cells (PBMC) of regular healthy donors. T cells were isolated from patient and healthy donor samples by Ficoll-Hypaque density centrifugation. The final product was resuspended at $3\times10^6$ cells/ml in media and stimulated with OKT-3/anti-CD3 (2.5 mg/ml; Ortho Bio-Tech) and anti-human CD28 (2.5 mg/ml; Biolegend; cat #302902) presence of 4 mg/ml of protamine sulfate and 1 mg/ml SLP76pTYR or vehicle for five minutes. T cell lysates were used in western blot analysis.

Figure 22:
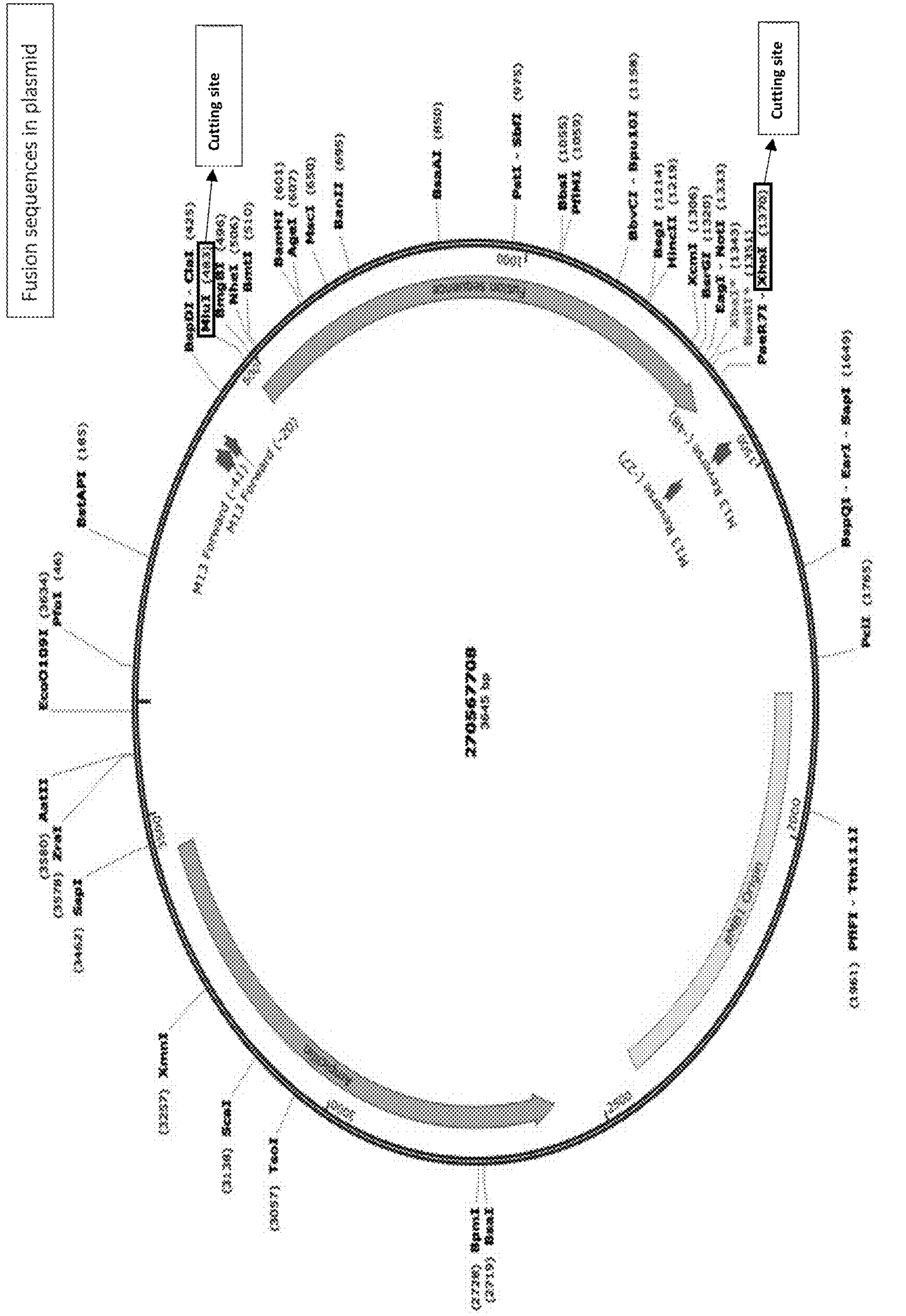
FIG. 22 (SEQ ID Nos: 1 and 7-8) depicts SLP76pTYR peptide and the related fusion sequences and plasmid.

Transducing primary T cells with SLP76pTYR: viruses were generated that specifically express SLP76pTYR; the sequences encoding SLP76pTYR were cloned as a fusion protein with pCherry (plasmid depicted in FIG. 22) ordered through Integrated DNA Technology (IDT). The insert was cloned into a pQCX-I-X retroviral vector between MLU1 and Xho1 restriction sites, and the insert was confirmed by digestion and sequencing. To generate retroviral supernatants, Phoenix packaging cells were plated in 60 $cm^2$ dishes and transfected with 20 μg of the vector using Lipofectamine 2000 reagent (Invitrogen, Carlsbad, CA), according to the manufacturer's protocol. The medium was changed after 8-12 hours, and viral supernatants were harvested after 24-36 hours. Concentrated viral supernatants were re-suspended in MDM media (Invitrogen) and used to transduce primary T cells in the presence of protamine sulfate (4 μg/ml) to enhance transduction efficiency. T cells were transduced with viruses containing either SLP76pTYR-pCherry or empty plasmid for 24 hours and then injected into mice.

Statistics. All numerical data are reported as means with standard deviation. Data were analyzed for significance with GraphPad Prism. Differences were determined using one-way or two-way ANOVA and Tukey's multiple comparisons tests, or with a student's t-test when necessary. P-values less than or equal to 0.05 are considered significant. According to power analyses, all transplant experiments were done with N=5 mice per group and repeated at least twice. Mice were sex-matched and age-matched as closely as possible.

Introduction

Graft-vs-host disease (GVHD) is primarily orchestrated by mature donor T cells (Breems and Lowenberg, 2005). Mature T cells in the graft facilitate stem cell engraftment and, most importantly, ensure the therapeutic graft-versus-leukemia (GVL) effect (Breems and Lowenberg, 2005, Tugues et al., 2018). However, these alloreactive T cells also facilitate the unwanted effect of graft-versus-host disease (GVHD) (Bastien et al., 2012). Standard immunosuppressive therapy for GVHD is not optimal, because it leaves patients susceptible to opportunistic infections such as Cytomegalovirus (CMV) and relapse of the malignancy being treated (Bleakley et al., 2012) (Ferrara, 2014). The pathophysiology of GVHD depends upon interactions between donor T cells and host antigen-presenting cells (APCs). T cell receptor (TCR)-mediated activation of donor T cells by APCs is critical for both GVHD and GVL effects (Guinan et al., 1999). Following TCR activation and expansion in secondary lymphoid organs, the alloreactive T cells migrate to target organs and cause tissue damage by producing inflammatory cytokines and by exhibiting cytotoxicity against healthy tissues (Ferrara, 2014). Thus, GVHD can be treated by interfering with T-cell activation and proliferation using calcineurin inhibitors (cyclosporine, tacrolimus), mTOR inhibitors (sirolimus), and antiproliferative agents (methotrexate, cyclophosphamide, or mycophenolate) (Reddy and Ferrara, 2008, Baxter and Hodgkin, 2002). However, while alleviating GVHD, global inhibition of T cell activation also negates the beneficial GVL effect. Thus, specific signaling pathways, which can be targeted to allow GVL effects to occur while inhibiting GVHD, need to be identified. T cell signaling requires a multimolecular proximal signaling complex, which includes adapter proteins such as SLP76 (Koretzky et al., 2006, Kambayashi et al., 2009). SLP is involved in phosphorylation of phospholipase C-gamma isoforms by ITK in T cells (Su et al., 1999). IL-2-inducible T-cell kinase (ITK) is a critical mediator of T cell receptor (TCR) signaling (Bunnell et al., 2000).

SLP-76 activates ITK through its N-terminal tyrosine at the position Y145 (Bogin et al., 2007, Jordan et al., 2006). When phosphorylated, the tyrosine residue 145 (Y145) of SLP76 binds to and activates the Tec family tyrosine kinase ITK (Bogin et al., 2007). Thus, a YaF mutation at Y145 of SLP76 leads to defective TCR-mediated ITK activation (Jordan et al., 2006). The SLP76 Y145 and ITK interaction is involved in signaling pathways that lead to cytokine production by T cell populations, as well as in regulating the development of a distinct, innate-type cytokine-producing T cell population in the thymus (Atherly et al., 2006), referred to as innate memory phenotype (IMP) T cells. $CD4^+$ and $CD8^+$ T cells from SLP76Y145FKI mice express significantly higher CD122, CD44, and Eomes compared to T cells from WT mice on a basal, unstimulated level (Mammadli et al., 2020). Since the activation, expansion, cytokine production, and migration of alloreactive donor T cells to target organs are hallmarks of GVHD (Henden and Hill, 2015, Lynch Kelly et al., 2015), efforts to understand signaling pathways that allow separation from GVL will enable us to develop target-specific therapeutic modulators. Both $CD4^+$ and $CD8^+$ T cells with CD44 low ($CD44^{lo}$) are considered naive cells. $CD4^+$ and $CD8^+$ T cells with CD44 high ($CD44^{hi}$) are considered antigen-experienced and activated cells. Both $CD4^+$ and $CD8^+$ T cells from SLP76Y145F and ITK-deficient mice express a higher proportion of cells with CD44hi and CD122hi (Mammadli et al., 2020). Both $CD4^+$ and $CD8^+$ T cells with $CD44^{hi}$ and $CD122^{hi}$ from SLP76Y145FKI and ITK deficient mice arise in the thymus during development, unlike memory $CD44^{hi}$ $CD4^+$ and $CD8^+$ T cells that mainly arise in the periphery of WT mice in response to foreign antigens or because of homeostatic proliferation (Mammadli et al., 2020). Experimental studies in $CD44^{hi}$ and $CD44^{lo}$ cells arising in the periphery of WT mice show conflicting results (Dutt et al., 2011, Zheng et al., 2009, Loschi et al., 2015, Anderson, 2003, Huang et al., 2019). In this example, it is shown that WT $CD8^+CD44^{lo}$ T cells induce severe GVHD, and that while WT $CD8^+CD44^{hi}$ T cells induce less GVHD, as has been reported, they eventually cause GVHD (Zhang et al., 2005, Huang et al., 2019). In contrast, SLP76Y145FKI $CD8^+CD44^{lo}$ T cells are much less likely to induce GVHD, and SLP76Y145FKI $CD8^+CD44^{hi}$ T cells do not cause GVHD, but maintain a significant GVL effect (Mammadli et al., 2020). Both $CD8^+$ and $CD4^+$ SLP76Y145FKI T cells exhibit attenuated TCR signaling and an innate memory phenotype (IMP) as indicated by expression of high levels of CD44 and CD122, and $CD8^+$ SLP76Y145FKI T cells also express higher levels of the transcription factor Eomes (Huang et al., 2014, Carty et al., 2014). The data suggest that IMP phenotype may not be enough to separate the wanted effect of GVL from the unwanted GVHD effect. It is also shown that disruption of the SLP76Y145/ITK interaction allows T cells to differentiate GVHD from GVL effects. Proinflammatory cytokines play a key role in the development of GVHD pathophysiology (Holler, 2002), and it is further shown that both $CD4^+$ and $CD8^+$ T cells from SLP76Y145FKI mice have reduced proinflammatory cytokine production, both on a serum level and a cellular level. Next, it was examined how $CD8^+$ T cells from SLP76Y145FKI mice maintained GVL effects. It was observed that about 70-80% $CD8^+$ T cells from SLP76 Y145FKI and ITK-deficient mice express Eomes, and it was found that these Eomes-expressing cells are critical for GVL effects. It is further demonstrated that Eomes-deficient WT or SLP76Y145FKI T cells did not mount a cytotoxic response against primary leukemia cells, both in vitro and in vivo (Cheng et al., 2016). Disrupting SLP76Y145 and ITK signaling in T cells also led to defects in migration to GVHD target organs.

Figure 12:
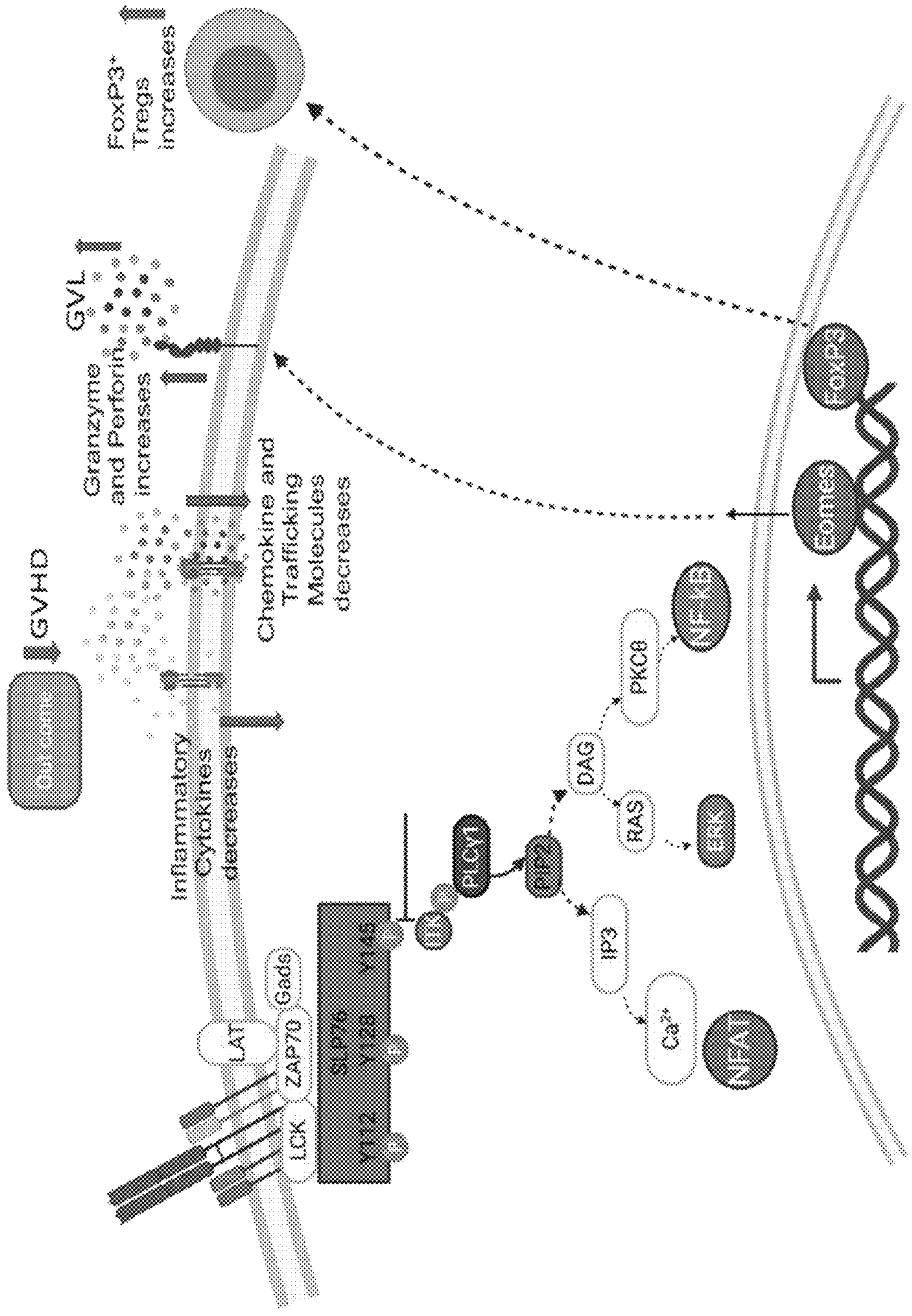
FIG. 12. depicts a general strategy of the inventions of the present disclosure.

Finally, to make the findings clinically relevant, a novel peptide inhibitor is provided, named SLP76145pTYR, that disrupts the interaction between SLP76 and ITK. It is shown that SLP76145pTYR specifically inhibits the phosphorylation of ITK and downstream signaling molecules, including PLCγ1 and ERK, in both human and mouse T cells (Kim et al., 2009). Furthermore, treating T cells with SLP76pTYR enhances the development of $FoxP3^+$ mouse regulatory T cells, while significantly reducing IFN-γ (Lu and Waller, 2009) and TNF-α (Mancusi et al., 2018) production by T cells from primary healthy human blood samples. Finally, SLP76145pTYR significantly reduced GVHD pathophysiology but maintained GVL function in a murine allo-HSCT major mismatch model. The studies therefore identify a novel, specific inhibitor capable of separating GVHD and GVL after allo-HSCT, with potential benefits for other T cell-mediated diseases as well (See FIG. 12 generally).

Results

Figure 13A:
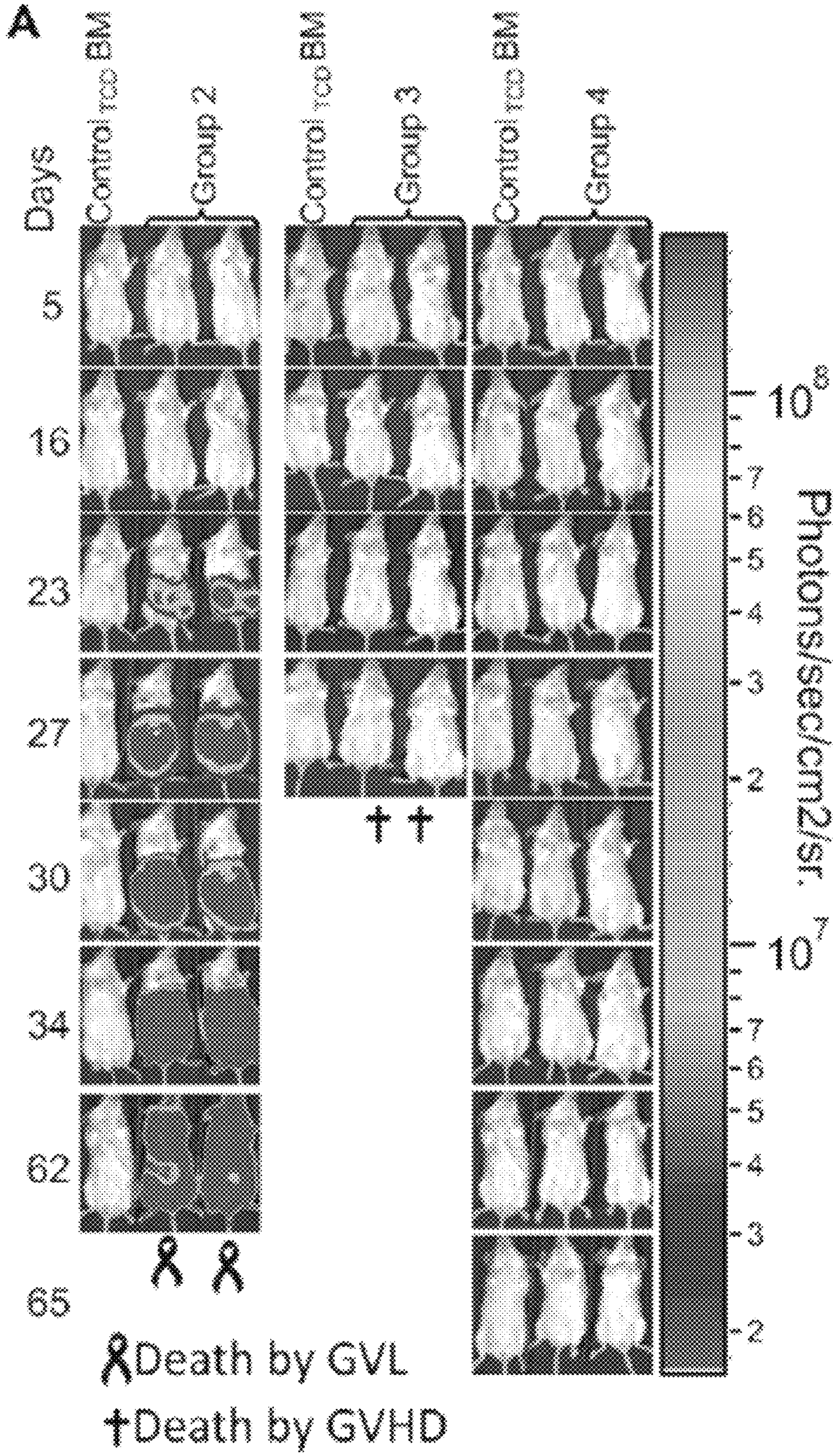
FIGS. 13A-13E depict disruption of ITK: SLP76 Y145 signaling allows tumor clearance without inducing GVHD.
Figures 13B, 13C, 13D, 13E:
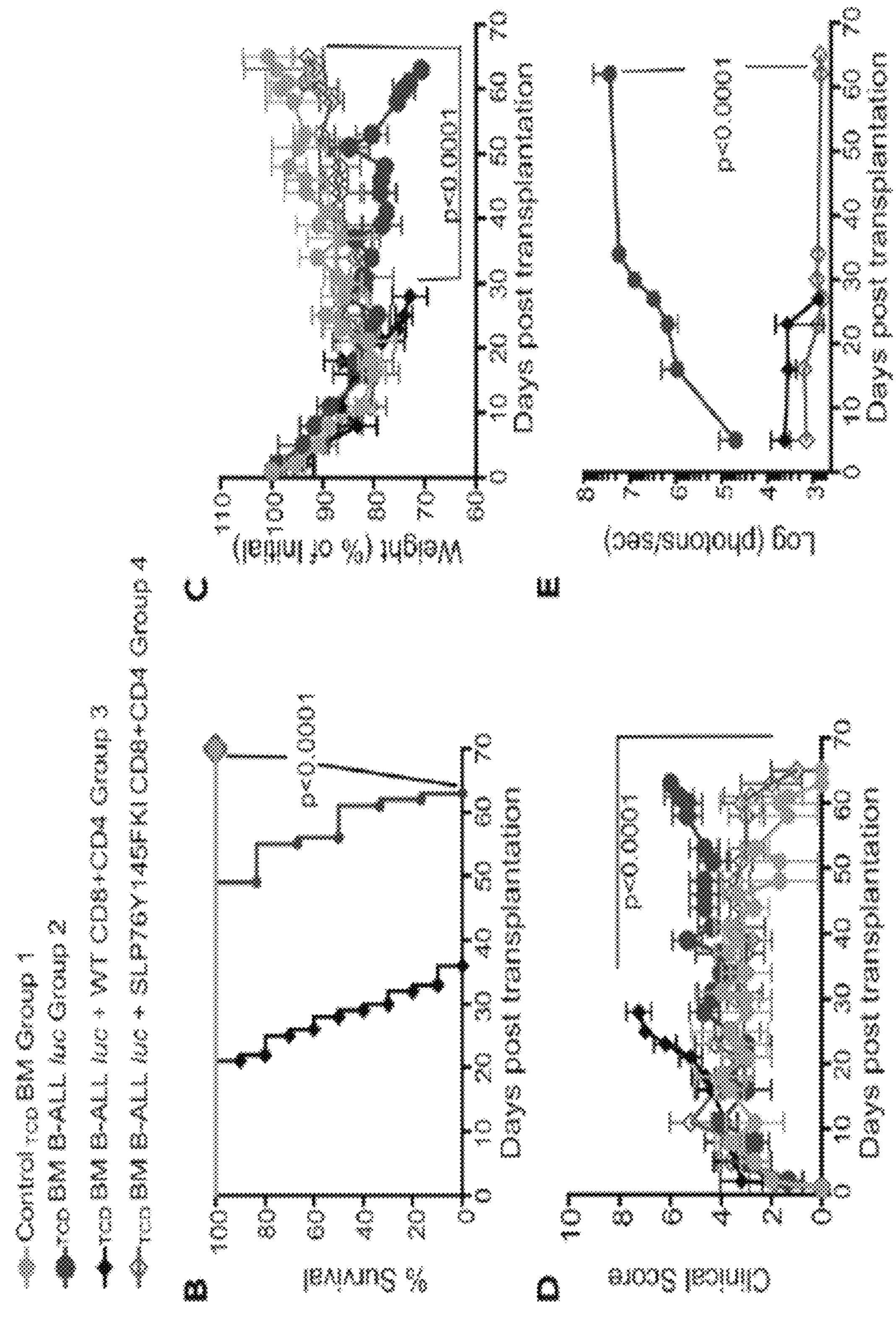
Figures 20A, 20B, 20C:
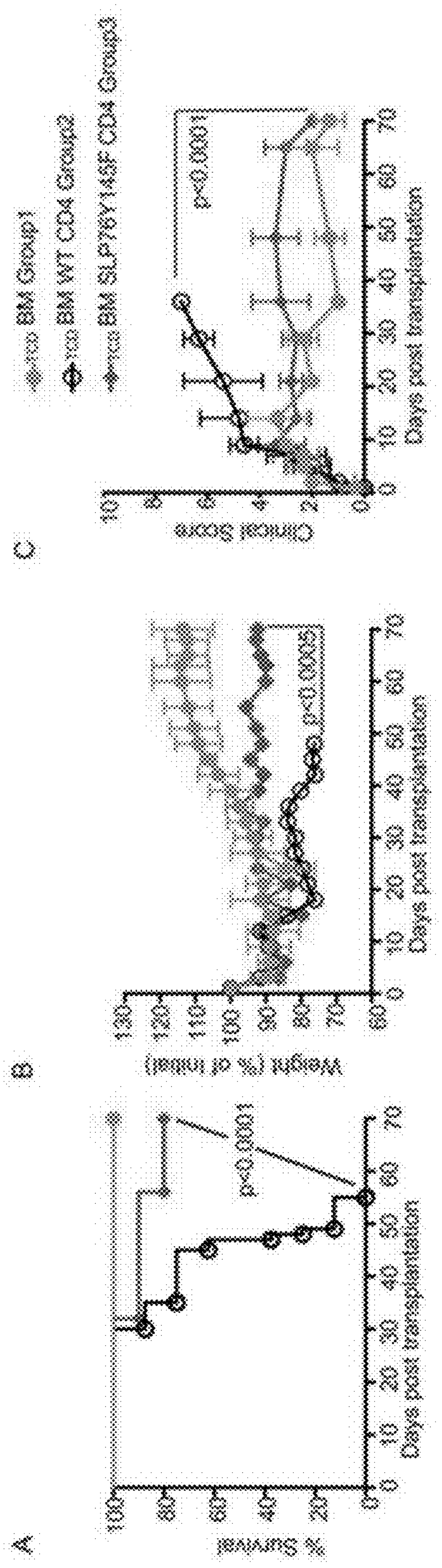
FIGS. 20A-20C depict SLP76 Y145FKI $CD4^+$ T cells exhibit attenuated induction of GVHD compared to WT T cells.

Disruption of ITK: SLP76 Y145 signaling allows tumor clearance without inducing GVHD. ITK is differentially required for GVHD and GVL (Mammadli et al., 2020). Therefore, it was tested whether this distinction depends on the interaction of ITK with SLP76. T cell signaling requires a multimolecular proximal signaling complex that includes adapter proteins such as SLP76 (Koretzky et al., 2006, Kambayashi et al., 2009). When SLP76 is phosphorylated on tyrosine residue 145 (Y145), it binds to and activates the Tec family tyrosine kinase ITK (Bogin et al., 2007). Thus, a Y→F mutation at Y145 (such as substitution characterized as Y145F) of SLP-76 leads to defective TCR-mediated ITK activation (Jordan et al., 2006), with effects on signaling pathways that lead to cytokine production by T cell populations. Given the role of SLP76 in regulating ITK signaling downstream of the T cell receptor, it was tested whether GVL effects would remain intact when allo-BMT was performed with T cells from SLP76 Y145FKI mice. To induce GVHD, MHC-mismatched donors and recipients were used, with T cell-depleted bone marrow ($_{TCD}$BM) from B6.PL-Thy1a/CyJ (Thy1.1) mice, donor T cells from C57BL/6 (B6) WT or SLP76Y145FKI mice (MHC haplotype b), and lethally irradiated BALB/c (MHC haplotype d) mice as recipients. Recipient mice were injected intravenously with $10\times10^6$ wild-type (WT) $_{TCD}$BM cells along with $2\times10^6$ FACS-sorted donor T cells ($1\times10^6$ $CD8^+$ and $1\times10^6$ $CD4^+$). $2\times10^5$ luciferase-expressing primary B-cell acute lymphoblastic leukemia (B-ALL)-luc blast cells as previously described (Cheng et al., 2016) were mixed with $_{TCD}$BM and CD4 and CD8 T cells, and intravenously injected into recipient BALB/c mice by tail vein. B-ALL is a primary B cell acute lymphoblastic leukemia, syngeneic to BALB/c mice and allogeneic to C57BL/6 (B6) mice. B-ALL cells were mixed with donor T cells and $_{TCD}$BM right before injection. Recipient BALB/c mice were monitored for cancer cell growth using IVIS bioluminescence imaging for over 60 days (FIG. 13A). While leukemia cell growth was observed in mice given T cell-depleted BM but no T cells, leukemia cell growth was not seen in mice transplanted with $CD4^+$ and $CD8^+$ T cells from either WT or SLP76Y145FKI mice. As expected, mice transplanted with WT $CD4^+$ and $CD8^+$ T cells suffered from GVHD, while mice transplanted with SLP76 Y145FKI $CD4^+$ and $CD8^+$ T cells displayed minimal signs of GVHD and survived for >65 days post-HSCT and tumor challenge (FIG. 13). Most animals transplanted with SLP76Y145FKI T cells survived for more than 65 days post-allo-HSCT (FIG. 13B), with significantly better survival and reduced clinical scores compared to those transplanted with WT T cells (scored based on weight, posture, activity, fur texture, and skin integrity as previously described (Cooke et al., 1996) (FIG. 13C-D)). BALB/c mice transplanted with SLP76Y145FKI T cells showed only residual tumor cell growth (as measured by bioluminescence), indicating that the donor cells maintained GVL functions similar to WT T cells (FIG. 13E). Donor $CD8^+$ T cells are more potent than $CD4^+$ T cells in mediating GVL effects, but both $CD4^+$ and $CD8^+$ T cells mediate severe GVHD in mice and humans (Amir et al., 2012, Yu et al., 2006, Wu et al., 2013). To determine whether $CD4^+$ T cell-intrinsic SLP76: ITK signaling might be sufficient to induce GVHD, we repeated the same experiments using purified $CD4^+$ T cells from either WT or SLP76Y145FKI mice in the MHC-mismatch mouse model of allo-HSCT (B6□BALB/c) (FIG. 20A-C). Recipients of WT $CD4^+$ T cells exhibited worse survival than mice receiving $_{TCD}$BM cells alone (FIG. 20A). In contrast, recipients of $_{TCD}$BM mixed with SLP76Y145FKI $CD4^+$ T cells had greatly reduced mortality and clinical scores compared to those given WT $CD4^+$ T cells (FIG. 20C), indicating that $CD4^+$ T cell-intrinsic SLP76: ITK signaling can contribute to the severity of GVHD.

More specifically, FIGS. 13A-13E depict disruption of ITK: SLP76 Y145 signaling allows tumor clearance without inducing GVHD. $1\times10^6$ purified $CD8^+$ T cells and $1\times10^6$ purified $CD4^+$ T cells from WT or SLP76 Y145FKI mice were mixed at a 1:1 ratio and transplanted with $2\times10^5$ B-ALL cells and $10\times10^6$ T cell-depleted bone marrow ($_{TCD}$BM) cells transplanted into irradiated BALB/c mice. Host BALB/c mice were imaged using the IVIS 50 system three times a week. (FIG. 13A) Group one received $10\times10^6$ T cell depleted bone marrow cells ($_{TCD}$BM) only. Group one mice are used as negative controls while imaging other groups that have luciferase-expressing primary leukemia cells. Group two received $10\times10^6$ $_{TCD}$BM with $2\times10^5$ B-ALL-luc cells ($_{TCD}$BM+B-ALL luc). The third group was transplanted with $10\times10^6$ $_{TCD}$BM cells and $1\times10^6$ purified WT $CD8^+$ and $1\times10^6$ $CD4^+$ T cells (1:1 ratio) along with $2\times10^5$ B-ALL-luc cells ($_{TCD}$BM+B-ALL-luc+WT $CD8^+$ and CD4+). Group four received $10\times10^6$ $_{TCD}$BM cells and $1\times10^6$ purified $CD8^+$ and $1\times10^6$ $CD4^+$ T cells (1:1 ratio from SLP76 Y145FKI) along with $2\times10^5$ B-ALL-luc B-ALL-luc cells ($_{TCD}$BM+B-$ALL^{luc}$+SLP76Y145F CD8+CD4). (FIG. 13B) We monitored the survival of recipient animals, (FIG. 13C) body weight changes, and (FIG. 13D) clinical score for 65 days post BMT. For weight changes and clinical score, one representative of 2 independent experiments is shown (n=3 mice/group for BM alone; n=5 experimental mice/group for all three groups). (see e.g., FIG. 13E). Tumor growth was quantified via luciferase bioluminescence. Statistical analysis for survival and the clinical score was performed using the log-rank test and two-way ANOVA, respectively. Note: Controls are naïve for cancer, but transplanted with $10\times10^6$ T cell depleted bone marrow alone ($_{TCD}$BM) and used as a negative control for BLI. See also FIGS. 20 and 21.

More specifically, FIGS. 20A-20C depict SLP76 Y145FKI $CD4^+$ T cells exhibit attenuated induction of GVHD compared to WT T cells. $10\times10^6$ T cell-depleted bone marrow cells and $1\times10^6$ purified WT or SLP76 Y154FKI $CD4^+$ T cells were transplanted into irradiated BALB/c mice. (FIG. 20A) The mice were monitored for survival, (FIG. 20B) changes in body weight, and (FIG. 20C) clinical score for 70 days post BMT. For weight changes and clinical score, one representative of 2 independent experiments is shown (n=3 mice/group for BM alone; n=5 experimental mice/group for all three groups). The p values are presented. Two-way ANOVA and Student's t-test were used for statistical analysis.

Figures 21A, 21B, 21C, 21D, 21E, 21F:
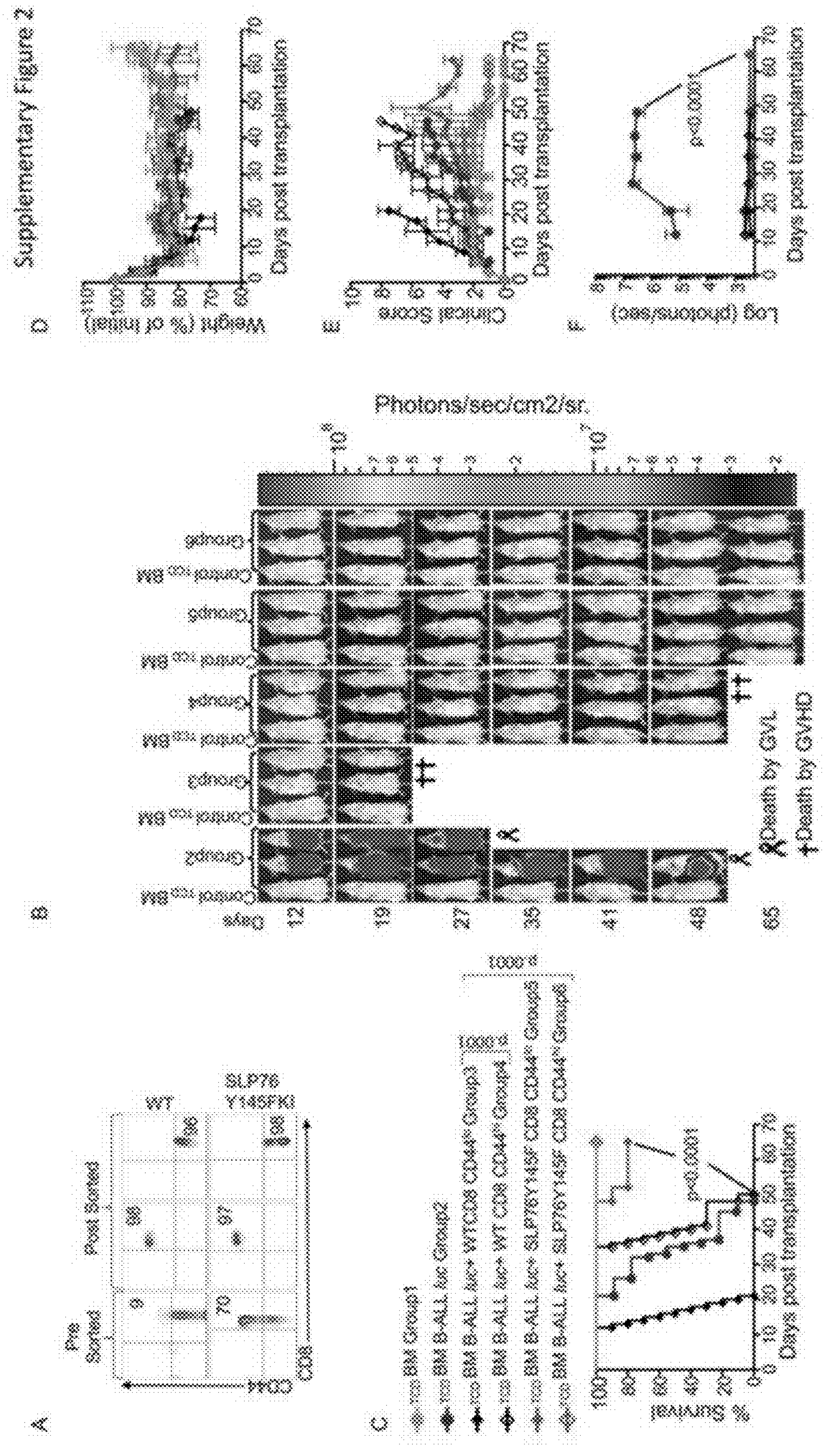
FIGS. 21A-21F depict the innate memory phenotype of $CD8^+$ T cells does not separate GVHD and GVL effects.

To test whether the IMP observed in SLP76Y145FKI T cells is necessary to separate the effects of GVL from GVHD, irradiated recipient BALB/c (MHC haplotype d) mice were transplanted with sorted $CD8^+CD44^{hi}$ (expressing the IMP) or $CD8^+CD44^{lo}$ (control) T cells from WT or SLP76Y145FKI mice (FIG. 21A). Before transplantation into recipient mice, donor T cells were examined for CD44 expression before and after sorting based on CD44 expression. Recipient mice were injected with $10\times10^6$ WT C57BI/6 $_{TCD}$BM cells, with or without $1\times10^6$ FACS-sorted $CD8^+$ $CD44^{lo}CD122^{lo}$ or $CD8^+CD44^{hi}CD122^{hi}$ (IMP) T cells from WT or SLP76Y145FKI mice (FIG. 21B). Recipient mice were challenged with $1\times10^5$ primary B-ALL-luc (Cheng et al., 2016) tumor cells and monitored for survival, weight changes, clinical score, and tumor burden (monitored by bioluminescence imaging twice a week) for at least 60 days (FIG. 21B). It was found that WT $CD8^+$ $CD44^{lo}CD122^{lo}$ T cells cleared the tumor, but recipients developed acute GVHD, while WT $CD8^+CD44^{hi}CD122^{hi}$ IMP T cells cleared the tumor but exhibited delayed induction of GVHD. In contrast, $CD8^+CD44^{hi}CD122^{hi}$ IMP (Mammadli et al., 2020) T cells from SLP76Y145FKI mice cleared the tumor, but recipients did not develop GVHD, while $CD8^+CD44^{lo}CD122^{lo}$ T cells from SLP76Y145F mice cleared the tumor effectively, but three out of 10 mice developed GVHD. These data indicate that WT donor $CD8^+$ $CD44^{hi}CD122^{hi}$ IMP T cells exhibited delayed GVHD but eventually caused GVHD, while SLP76Y145FKI $CD8^+$ $CD44^{hi}CD122^{hi}$ IMP T cells induce GVL but avoid the induction of GVHD (FIG. 21B-F).

More specifically, FIGS. 21A-21F depict the innate memory phenotype of $CD8^+$ T cells does not separate GVHD and GVL effects. (FIG. 21A) Purified T cells from WT and SLP76Y145FKI mice were examined for expression of CD44 pre- and post-sort. (FIG. 21B) All recipient BALB/c mice were lethally irradiated and divided into six different groups. Group one was transplanted with $10\times10^6$ $_{TCD}$BM. Group 2 was transplanted with $10\times10^6$ $_{TCD}$BM and $1\times10^5$ B-ALL-luc. Group 3 was transplanted with $10\times10^6$ $_{TCD}$BM along with $1\times10^6$ purified WT $CD8^+CD44^{lo}$ T cells and $1\times10^5$ B-ALL-luc. Group 4 was transplanted with $10\times10^6$ $_{TCD}$BM along with $1\times10^6$ purified WT $CD8^+$ $CD44^{hi}$ T cells, and $1\times10^5$ B-ALL-luc. Group 5 was transplanted $10\times10^6$ $_{TCD}$BM along with $1\times10^6$ purified SLP76Y145FKI $CD8^+CD44^{lo}$ T cells and $1\times10^5$ B-ALL-luc. Group 6 was transplanted with $10\times10^6$ $_{TCD}$BM and $1\times10^6$ purified SLP76Y145FKI $CD8^+$ $CD44^{hi}$ T cells and $1\times10^5$ B-ALL-luc. These mice were monitored for tumor growth using the IVIS 50 system. (FIG. 21C) The mice were monitored for survival, (FIG. 21D) changes in body weight, and (FIG. 21E) animal clinical score for 65 days post BMT. For body weight changes and clinical score, one representative of 2 independent experiments is shown (n=3 mice/group for BM alone; n=5 experimental mice/group for all other groups. (FIG. 21F) Quantitated luciferase bioluminescence of luciferase-expressing B-ALL cells. Statistical analysis for survival and the clinical score was performed using the log-rank test and two-way ANOVA, respectively. P values are presented with each figure. Note: Controls are naïve for tumor, but transplanted with $10\times10^6$ T cell depleted bone marrow alone ($_{TCD}$BM) and used as a negative control for BLI.

Figures 14E, 14F, 14G, 14H:
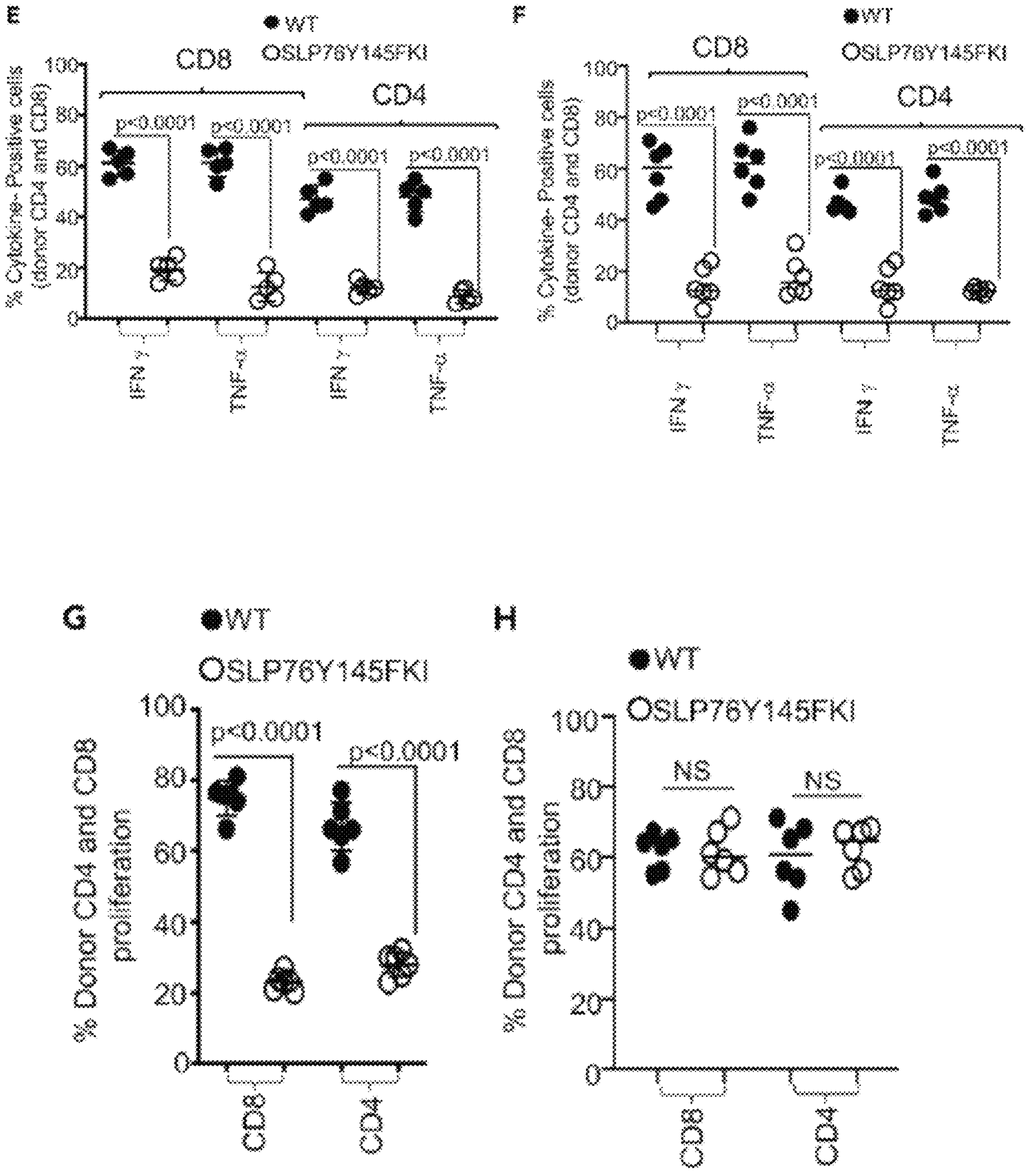

SLP76Y145FKI T cells produce less proinflammatory cytokines and exhibit reduced proliferation. Proinflammatory cytokine production by donor T cells is considered to be one of the hallmarks of GVHD (D'Aveni et al., 2015). To assess whether $CD4^+$ or $CD8^+$ T cells with attenuated TCR signaling produce inflammatory cytokines similar to $CD4^+$ or $CD8^+$ T cells from WT mice, $1\times10^6$ $CD4^+$ or $CD8^+$ T cells were transplanted in separate experiments from either WT mice or SLP76Y145FKI mice to irradiated BALB/c mice as recipients. At day seven post-transplantation, recipient BALB/c mice were sacrificed, and serum was obtained and assessed for levels of the proinflammatory cytokines IL-33, IL-1α, IFN-γ, TNF-α, and IL-17A by multiplex ELISA (FIG. 14A-B). It was discovered that recipient animals transplanted with $CD4^+$ or $CD8^+$ T cells (in separate experiments) from SLP76Y145FKI mice had significantly less production of proinflammatory cytokines compared to recipient mice transplanted with $CD4^+$ or $CD8^+$ T cells from WT mice (FIG. 14A-B). To examine the sources of these observed proinflammatory cytokines, spleen cells were restimulated from recipient mice that were transplanted with $CD4^+$ or $CD8^+$ T cells from WT or SLP76Y145FKI mice in separate experiments. Spleen cells were restimulated with anti-CD3 and anti-CD28 in the presence of Brefeldin A, and donor $CD4^+$ and $CD8^+$ T cells were gated by flow cytometry using anti-$H2K^b$ antibodies (expressed by donor cells), anti-CD3, anti-CD4, and anti-CD8. It was observed that donor $CD4^+$ and $CD8^+$ T cells from SLP76Y145FKI mice produced significantly less IFN-γ and TNF-α compared to donor $CD4^+$ and $CD8^+$ T cells from WT mice. Thus, these data confirm that the changes in proinflammatory cytokine serum levels result from changes in production by the donor T cells, and that T cells from TCR-attenuated mice produce less inflammatory cytokines (FIG. 14C-E). To examine whether SLP76Y145FKI T cells are capable of producing cytokines in general, spleen cells from recipient mice transplanted with either WT or SLP76Y145FKI T cells were stimulated with PMA/ionomycin (to bypass the proximal signaling defect (FIG. 23)), or left unstimulated for 6 hours in the presence of Brefeldin A, followed by the analysis of IFN-γ and TNF-α production. SLP76Y145FKI T cells were capable of producing IFN-γ and TNF-α when T cell signaling was bypassed by re-stimulation with PMA and ionomycin (FIG. 23); however, compared to WT T cells, they produced significantly less inflammatory cytokines when stimulated via TCR (anti-CD3 and anti-CD28) (FIG. 14C-E). Next, it was determined whether the reduction in cytokine production by SLP76Y145FKI donor T cells was due to cell-intrinsic or cell-extrinsic factors. SLP76Y145FKI $CD8^+$ and $CD4^+$ T cells were mixed purified with purified WT $CD8^+$ or $CD4^+$ T cells separately at a 1:1 ratio, and transplanted the mixed cells into irradiated BALB/c mice as described above. The congenic markers CD45.1 (WT C57BL/6) and CD45.2 (SLP76Y145FKI) were used to distinguish donor cells from the different strains of mice within the same recipient. On day 7, donor T cells were isolated from recipient mice using flow cytometry (anti-H2Kb) and examined for IFN-γ and TNF-α expression as described above. It was found that WT donor $CD8^+$ and $CD4^+$ T cells (CD45.1) produced higher levels of inflammatory cytokines than SLP76Y145FKI donor $CD8^+$ and $CD4^+$ T cells (CD45.2), suggesting that the reduced cytokine production observed by SLP76Y145FKI donor T cells is T cell-intrinsic (FIG. 14F).

More specifically, FIGS. 14A-14H depict SLP76Y145FKI donor $CD8^+$ and $CD4^+$ T cells exhibit reduced cytokine production and reduced proliferation. $1\times10^6$ purified $CD8^+$ or $CD4^+$ T cells from C57Bl/6 WT or C57Bl/6 SLP76Y145FKI (MHC haplotype b) mice were transplanted into irradiated BALB/c (MHC haplotype d) mice in separate experiments. (FIGS. 14A-B) At day seven post-allo-HSCT, recipient BALB/c mice transplanted with either $CD8^+$ or $CD4^+$ T cells were euthanized, and ELISA was performed to determine serum cytokines (IL-33, IL1α, IFN-γ, TNF-α, and IL-17A) from recipient mice. (FIGS. 14C-D) Donor $CD4^+$ or $CD8^+$ T cells were examined for IFN-γ and TNF-α by intracellular staining after stimulation with anti-CD3/anti-CD28, as determined by flow cytometry. (FIG. 14E) Donor $CD8^+$ or CD4+ T cells from several experiments were examined for IFN-γ and TNF-α as above. (FIG. 14F) Flow cytometry analysis of purified $CD4^+$ or $CD8^+$WT and SLP76Y145FKI T cells that were mixed at a 1:1 ratio for transplantation into irradiated BALB/c mice. At day seven donor T cells were stimulated with anti-CD3/anti-CD28, then were gated for expression of H-$2K^b$, CD45.1, CD 45.2. on WT T cells and SLP76Y145FKI cells and intracellular expression of IFN-γ and TNF-α analyzed by flow cytometry. Combined data from two independent experiments is shown, and the p value for each experiment is shown. (FIG. 14G) Purified $CD8^+$ or $CD4^+$ WT or SLP76Y145FKI donor T cells were transplanted into irradiated BALB/c mice. On day seven, donor T cells were analyzed for donor $CD8^+$ or $CD4^+$ T cell proliferation by examining BrdU incorporation by flow cytometry. (FIG. 14H) Purified $CD8^+$ or $CD4^+$ T cells from WT or SLP76Y145FKI mice were mixed at a 1:1 WT: SLP76Y145FKI ratio and transplanted into irradiated BALB/c mice. At day 7, splenic donor T cells were gated for the expression of H-$2K^b$, CD45.1, and CD45.2, and analyzed for BrdU incorporation. See also FIG. 23.

Figure 23:
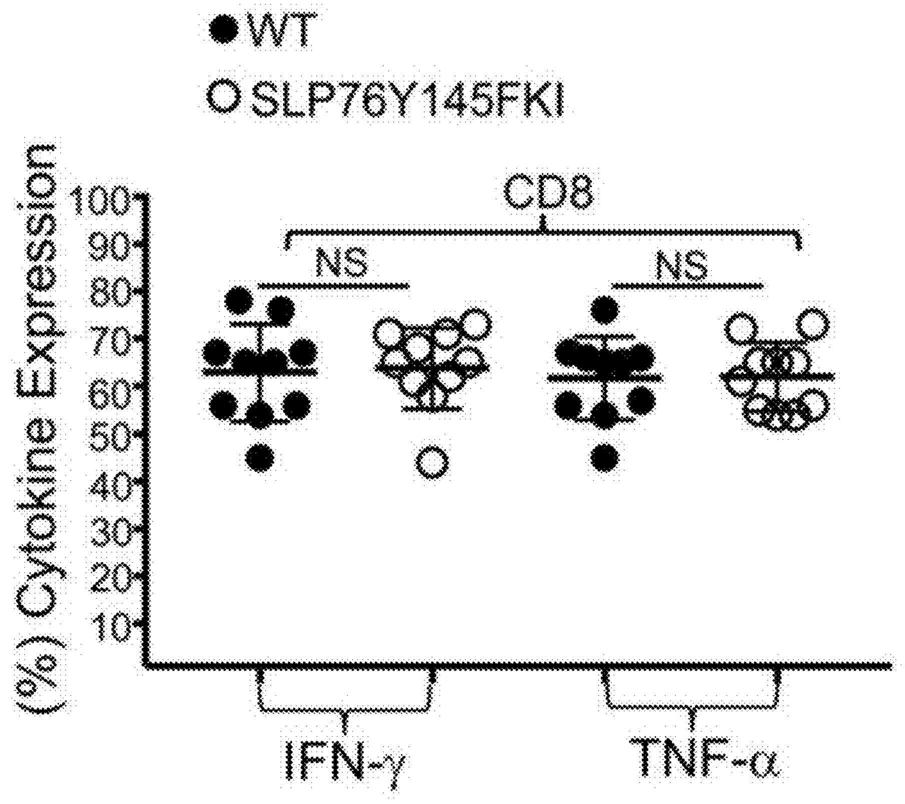
FIG. 23 depicts SLP76Y145FKI T cells are capable of cytokine production.

More specifically, FIG. 23 depicts SLP76Y145FKI T cells are capable of cytokine production. Purified T cells from WT and SLP76Y145FKI C57Bl/6 mice were transplanted into irradiated BALB/c mice (MHC haplotype d) as recipients. On day 7, donor T cells were gated for expression of H-$2K^b$, CD45.2, and CD45.1, and analyzed for intracellular expression of IFN-γ and TNF-α following ex vivo stimulation with PMA/ionomycin. Data from several experiments were combined, and statistical analysis performed using two-way ANOVA and Student's t-test, with p values presented.

Next, it was examined whether SLP76Y145FKI donor T cells proliferated similarly to WT donor $CD4^+$ and $CD8^+$ T cells. Lethally irradiated recipient BALB/c mice were transplanted as mentioned above, with either WT or SLP76Y145FKI donor $CD4^+$ or $CD8^+$ T cells. Recipient mice were injected with BrdU as described, and seven days post-allotransplantation, recipient mice were sacrificed and examined for proliferation by BrdU incorporation. SLP76Y145FKI donor T cells showed reduced proliferation compared to WT donor T cells FIG. 14G. To determine if the reduced proliferation by SLP76Y145FKI donor T cells was due to cell-intrinsic mechanisms, we mixed sort-purified SLP76Y145FKI and WT $CD4^+$ and $CD8^+$ at a 1:1 ratio, followed by transplantation as described above in (FIG. 14G). Interestingly, no difference was observed in BrdU incorporation by WT and SLP76Y145FKI donor $CD4^+$ and $CD8^+$ T cells in spleens of recipient mice in the mixed transplant models, indicating that the reduced proliferation of donor SLP76Y145FKI T cell proliferation was due to cell-extrinsic effects (FIG. 14H).

Figures 15A, 15B, 15C:
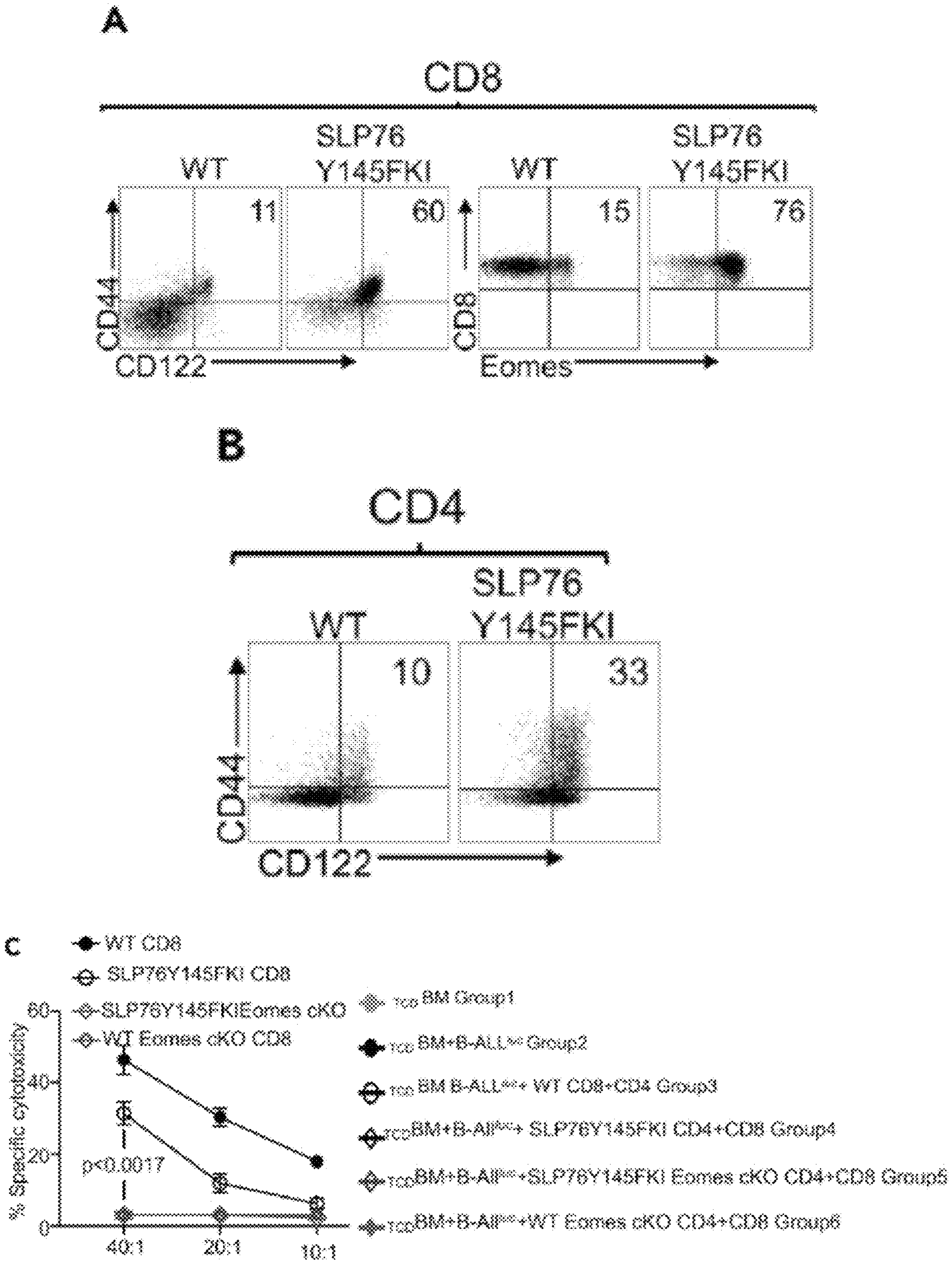
FIGS. 15A-15H depict Eomes is required for cytotoxicity and GVL effect by both WT and SLP76Y145FKI T cells.

Eomes is needed for cytotoxicity and GVL effect by both SLP76Y145FKI and WT T cells. The innate memory phenotype (IMP: $CD44^{hi}CD122^{hi}Eomes^{hi}$) (Mammadli et al., 2020, Huang et al., 2013) of SLP76Y145FKI $CD8^+$ and $CD4^+$ T cells arises in the thymus during development, as opposed to memory $CD8^+$ and $CD4^+$ T cells that are also $CD44^{hi}$, but largely arise in the periphery of WT mice in response to foreign antigens or due to homeostatic proliferation (Weinreich et al., 2010). We examined pre-transplanted $CD4^+$ and $CD8^+$ T cells for the CD44 and CD122 phenotype, and $CD8^+$ T cells for CD44, CD122, and Eomes expression, and observed that SLP76Y145FKI T cells expressed higher levels of CD44, CD122, and Eomes compared to $CD8^+$ T cells from WT mice (FIG. 15A-B).

More specifically, FIGS. 15A-15H depict eomes is required for cytotoxicity and GVL effect by both WT and SLP76Y145FKI T cells. (FIGS. 15A-B) Purified WT and SLP76Y145FKI $CD8^+$ and $CD4^+$ T cells were examined for expression of CD44, CD122, and Eomes by flow cytometry.

(FIG. 15C) Purified donor CD8+ T cells from either WT or SLP76 Y145FKI Eomes-sufficient, Eomes-deficient, or Eomes-flox control mice were transplanted into irradiated BALB/c (MHC haplotype d) mice. On day seven, donor T cells were purified as described and used in an ex vivo cytotoxicity assay against B-ALL-luc cells at 40:1, 20:1, and 10:1 ratios. (FIG. 15D) $1\times10^6$ purified WT or SLP76Y145FKI Eomes-sufficient, Eomes-deficient, or Eomes-flox control $CD8^+$ T cells and $1\times10^6$ purified $CD4^+$ T cells were mixed and transplanted along with $2\times10^5$ B-ALL-luc cells and $10\times10^6$ T cell-depleted bone marrow $_{TCD}$BM cells into irradiated BALB/c mice. Host BALB/c mice were imaged using IVIS 3 times a week. Group one received $10\times10^6$ T $_{TCD}$BM alone. Group two received $10\times10^6$ $_{TCD}$BM along with $2\times10^5$ B-ALL-luc cells ($_{TCD}$BM+B-ALL$^{luc}$). Group three was transplanted with $10\times10^6$ $_{TCD}$BM and $1\times10^6$ purified WT $CD8^+$ T cells+$1\times10^6$ $CD4^+$ T cells, and $2\times10^5$ B-ALL-luc cells ($_{TCD}$BM+B-ALL$^{luc}$+WT CD8+CD4). Group four received $10\times10^6$ $_{TCD}$BM and $1\times10^6$ purified $CD8^+$ T cells+$1\times10^6$ $CD4^+$ T cells from SLP76 Y145FKI Eomes-sufficient mice along with $2\times10^5$ B-ALL-luc cells ($_{TCD}$BM+B ALL$^{luc}$+SLP75Y145FKI CD8+CD4). Group five received $10\times10^6$ $_{TCD}$BM and $1\times10^6$ $CD8^+$ T cells+$1\times10^6$ $CD4^+$ purified T cells from SLP76 Y145FKI Eomes-deficient mice along with $2\times10^5$ B-ALL-luc cells ($_{TCD}$BM+B-ALL$^{luc}$+SLP75Y145FKI Eomes-cKO $CD8^+CD4$). Group six received $10\times10^6$ $_{TCD}$BM and $1\times10^6$ $CD8^+$ T cells+$1\times10^6$ $CD4^+$ purified T cells from WT Eomes-deficient mice along with $2\times10^5$ B-ALL-luc cells ($_{TCD}$BM+B-ALL$^{luc}$+WT Eomes cKO CD8+CD4). (FIG. 15E) The mice were monitored for survival, (FIG. 15F) body weight changes, and (FIG. 15G) clinical score for 50 days post BMT. For weight changes and clinical score, one representative of 2 independent experiments is shown (n=3 mice/group for BM alone; n=5 experimental mice/group for all three groups). The survival groups are a combination of all experiments. (FIG. 15H) Luciferase bioluminescence of tumor growth was quantified. Statistical analysis for survival and the clinical score was performed using log calculation. Two-way ANOVA was used for statistical analysis and results were confirmed by students t-test, p values are presented. Note: Controls are naïve for tumor, but transplanted with $10\times10^6$ T cell depleted bone marrow alone ($_{TCD}$BM) and used as a negative control for BLI. See also FIGS. 24A and 24B.

Figures 15D, 15E, 15F, 15G, 15H:
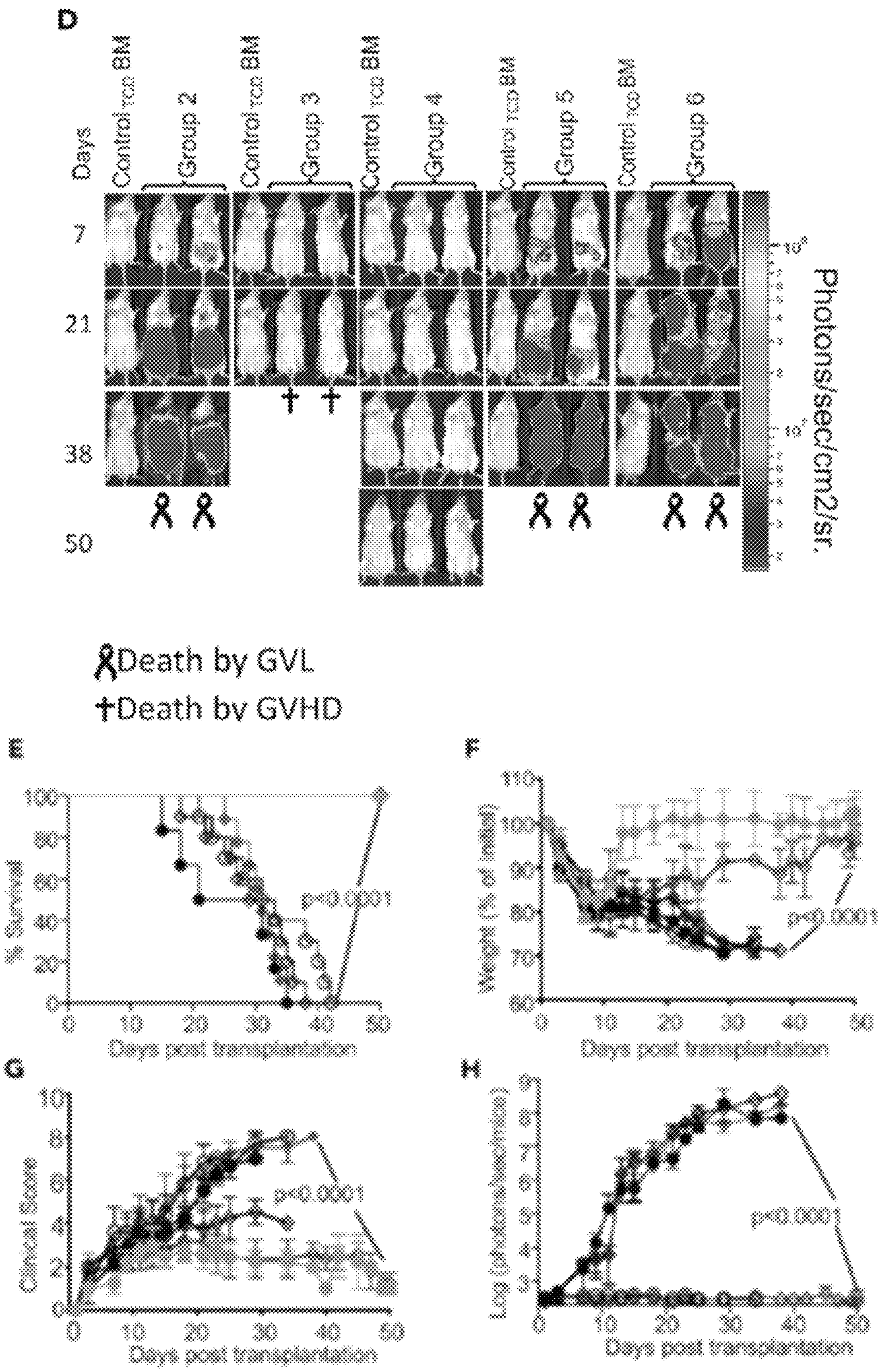

To further investigate the role of Eomes in tumor clearance and cytotoxic function, we crossed SLP76Y145FKI mice with Eomes$^{flox/flox}$ mice, and crossed these offspring with CD4cre to delete Eomes specifically in both $CD4^+$ and $CD8^+$ T cells (Jordan et al., 2008, Carty et al., 2014, Pikovskaya et al., 2016) (SLP76Y145FKI Eomes conditional knockout, SLP76Y145FKI cKO). To obtain ex vivo activated cells, we performed similar allo-HSCT experiments as described above, and used WT or SLP76Y145FKI $CD8^+$ T cells with or without Eomes expression. Seven days post-transplant, donor $CD8^+$ T cells were sorted as previously described by $H2K^b$ positivity, and in vitro cytotoxicity assays were performed at a 40:1, 20:1, and 10:1 ratio (effector: target). We observed that donor T cells lacking Eomes from either SLP76Y145FKI or WT mice could not kill tumor targets (FIG. 15C). Next, it was examined the role of Eomes in the allo-HSCT model. Lethally irradiated BALB/c mice were injected intravenously with $10\times10^6$ WT T cell-depleted BM cells along with $1\times10^6$ FACS-sorted $CD8^+$ and $CD4^+$ T cells from either WT mice or SLP76Y145FKI Eomes$^{flox/flox}$ (SLP76Y145FKI Eomes cKO) mice, with or without CD4cre (to delete Eomes specifically in $CD4^+$ and $CD8^+$ T cells), along with $2\times10^5$ luciferase-expressing B-ALL-luc blast cells as described (Cheng et al., 2016). Recipient animals transplanted with WT T cells cleared the tumor cells but developed acute GVHD (FIG. 15D). Recipient animals transplanted with Eomes sufficient (Eomes$^{flox/flox}$ mice without CD4cre) SLP76Y145FKI T cells cleared the tumor without showing signs of GVHD (FIG. 15D). These animals were monitored for survival (FIG. 15E) and weight loss (FIG. 15F). Recipient animals were also evaluated for clinical score 2-3 times per week by a scoring system that sums changes in 6 clinical parameters: (1) weight loss, (2) posture, (3) activity, (4) fur texture, (5) diarrhea, and (6) skin integrity (Cooke et al., 1996). Animals that lost ≥30% of their initial body weight were euthanized. (FIG. 15G). The bioluminescence data were analyzed and quantified with Living Image Software (Xenogen) and Igor Pro (Wave Metrics, Lake Oswego, OR) (FIG. 15H). Notably, recipient animals transplanted with Eomes deficient (Eomes$^{flox/flox}$ mice with CD4cre, called SLP76Y145FKI Eomes cKO) T cells could not clear the tumor, and all died from tumor burden. Recipient animals transplanted with WT Eomes deficient (Eomes$^{flox/flox}$ mice with CD4cre, called WT Eomes cKO) T cells developed severe GVHD and were also unable to clear transplanted leukemia cells. The deletion of Eomes using the Eomes$^{flox/flox}$ CD4 cre mice by flow cytometry (FIG. 24) was confirmed. These data provided further evidence that Eomes is required for the GVL effect.

Figures 24A, 24B:
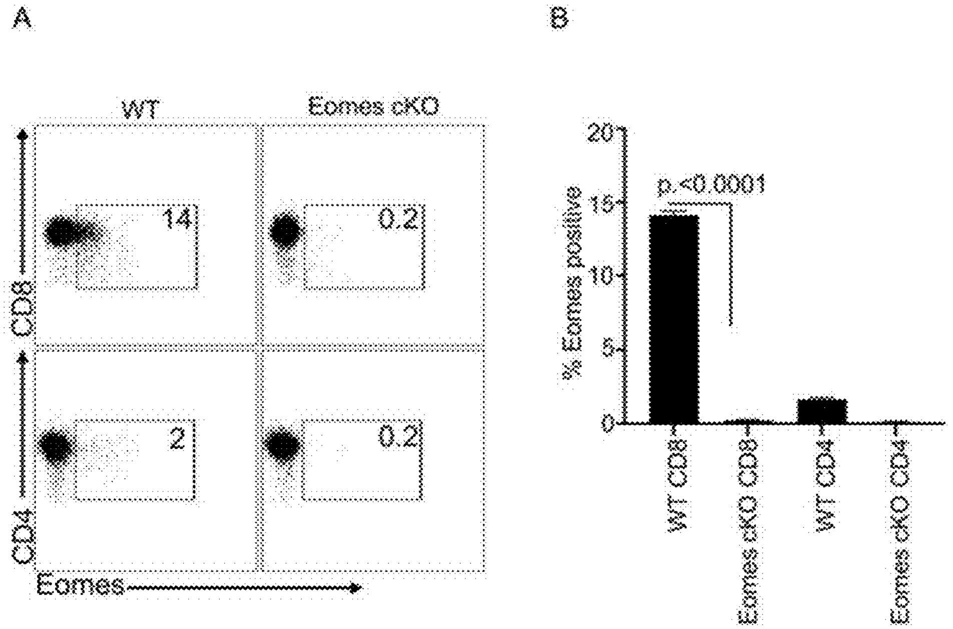
FIGS. 24A and 24B depict Eomes deletion on $CD8^+$ and $CD4^+$ T cells.

More specifically, FIGS. 24A and 24B depict eomes deletion on CD8+ and $CD4^+$ T cells. (FIG. 24A) Purified donor $CD8^+$ and $CD4^+$ T cells from either WT or WT Eomes-deficient (Eomes cKO) mice on a C57Bl/6 background were examined for Eomes expression. (FIG. 24B) Quantitative analysis from flow cytometry data of several experiments. For statistical analysis a two-way ANOVA and student's t test was used, p values are presented.

Figures 16A, 16B, 16C, 16D:
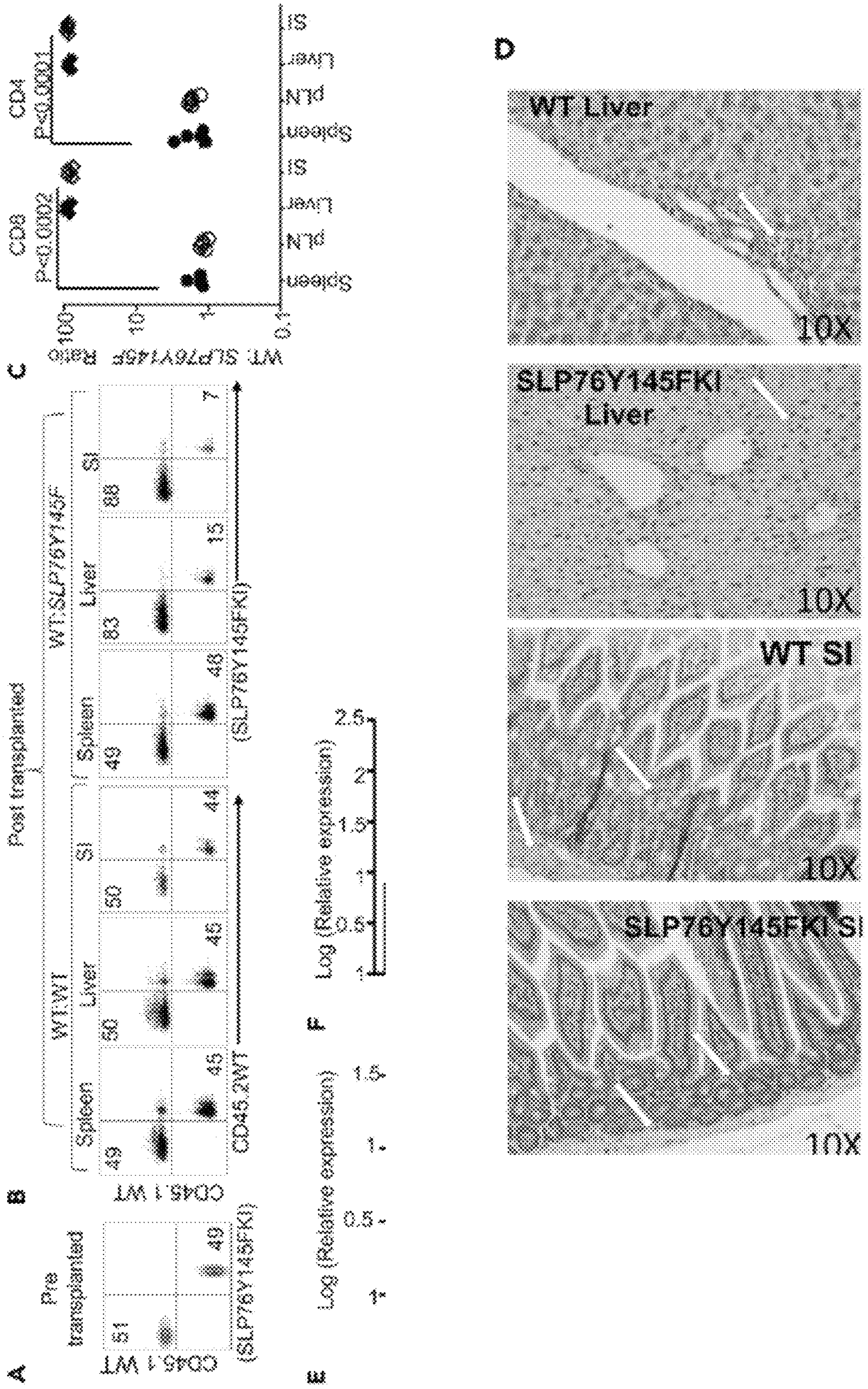
FIGS. 16A-16G depict SLP76Y145/ITK signaling is required for T cell migration to the GVHD target tissues.
Figures 25A, 25B:
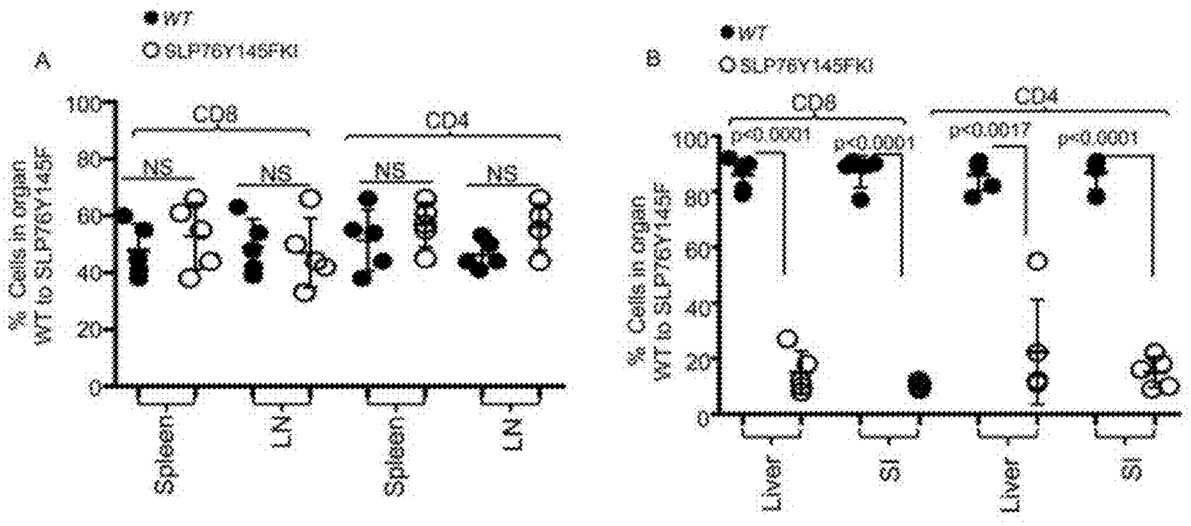
FIGS. 25A and 25B depict quantitative analysis of donor T cells in secondary lymphoid organs and GVHD target organs.

SLP76Y145/ITK signaling is needed for T cell migration to the GVHD target tissues. GVHD involves early migration of alloreactive donor T cells into the target organs, followed by T cell expansion and tissue destruction (Ferrara, 2014). Modulation of alloreactive T cell trafficking has been suggested to play a significant role in ameliorating experimental GVHD (Lu et al., 2010). Therefore, the trafficking of donor T cells to GVHD target tissues was examined, as previously described (Lu et al., 2010). Irradiated BALB/c recipient mice were injected with $CD8^+$ and $CD4^+$ T cells from C57Bl/6 background SLP76Y145FKI (CD45.2+) and WT B6LY5 (CD45.1+) mice mixed at a 1:1 ratio (FIG. 16A), and seven days post-transplantation, recipient mice were examined for the presence of donor $CD8^+$ and $CD4^+$ T cells in the spleen, lymph nodes, liver, and small intestines. While the WT: SLP76Y145FKI T cell ratio for both $CD8^+$ and $CD4^+$ cells remained approximately 1:1 in the spleen and lymph nodes (FIG. 16B-C), this ratio in the liver and small intestine was significantly elevated, suggesting that SLP76Y145FKI $CD8^+$ and $CD4^+$ T cells were defective in migration to and expansion in those tissues (FIG. 25A-B). Using histological staining for H&E, significant leukocyte infiltration into GVHD target organs such as liver, skin, and small intestine (SI) (Cho et al., 2020) was observed, in WT T cell recipients but not in SLP76Y145FKI T cell recipients (FIG. 26D).

Figures 16E, 16F, 16G:
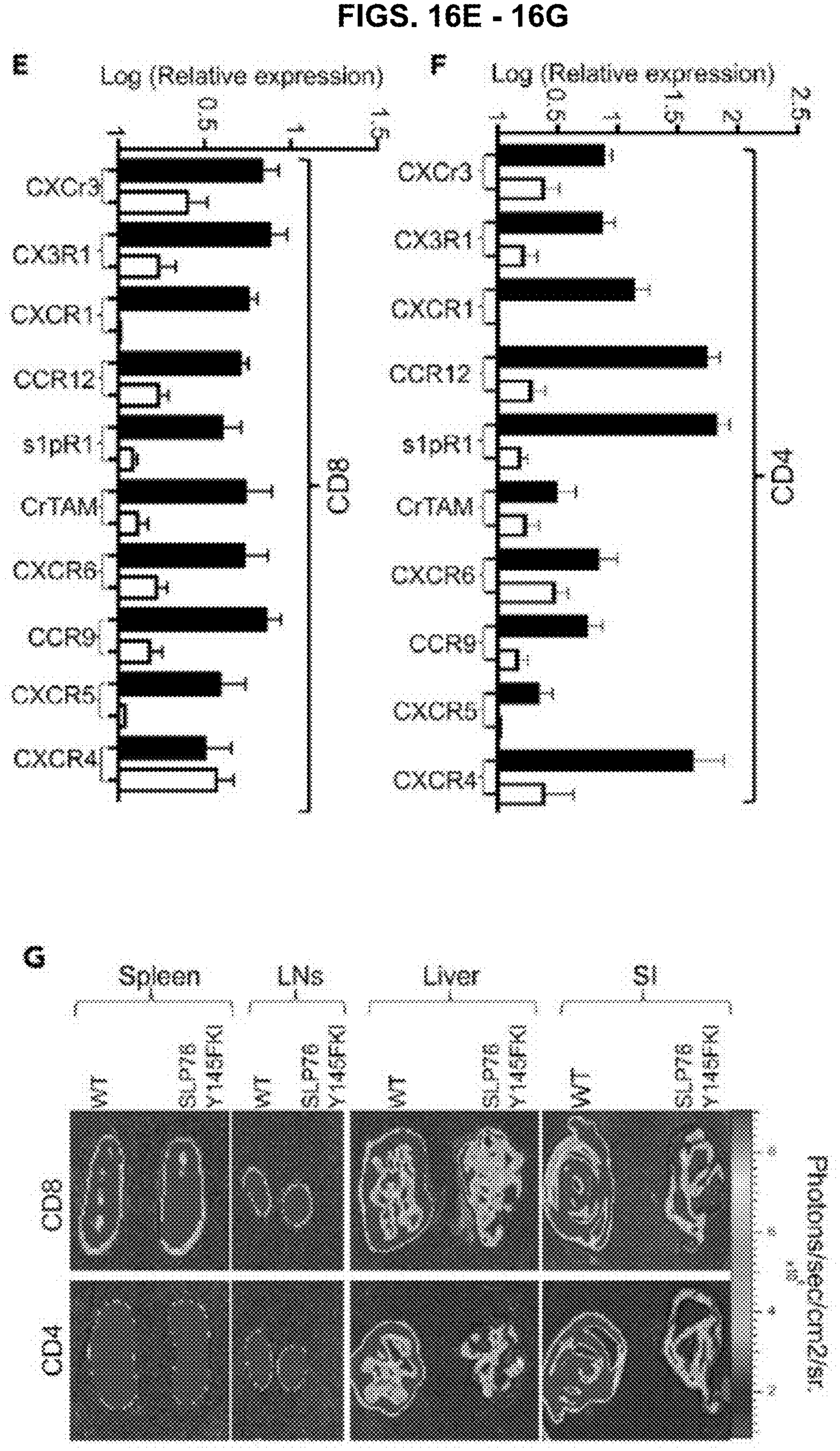

Pro-inflammatory conditioning treatment may promote donor T cell migration into GVHD target tissues (Wysocki et al., 2004, Seif et al., 2017). We therefore examined if the observed defect in trafficking was due to chemokine receptor expression on donor T cells. Irradiated BALB/c recipient mice were injected with WT and SLP76Y145FKI $CD8^+$ and CD4$^+$ T cells as described previously, and at seven days post-transplantation, donor CD4$^+$ and CD8$^+$ T cells were FACS sorted from the recipient using H2K$^b$ expression. Purified donor CD4$^+$ and CD8$^+$ T cells were examined for chemokine receptor expression by qPCR. Indeed, it was found that expression of chemokine receptors and other molecules that play a critical role in T cell migration (CXCR3, CX3r1, CXCR1, CCR12, s1pR1, CrTAM, CXCR6, CCR9, CXCR5, CXCr4) were significantly reduced in SLP76Y145FKI CD8$^+$ and CD4$^+$ T cells at day 7 post-transplantation compared to WT CD8$^+$ and CD4$^+$ T cells (FIG. 16E-F).

Figures 26A, 26B:
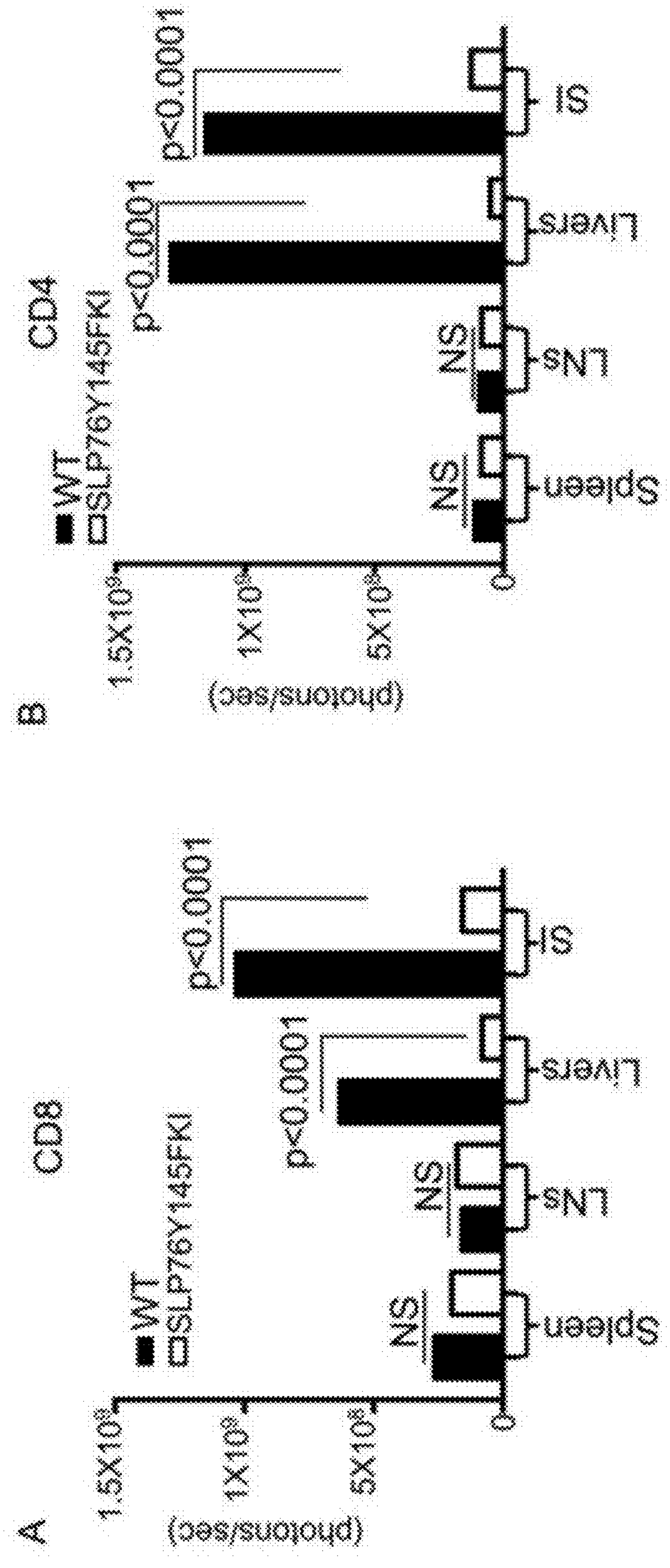
FIGS. 26A and 26B depict quantitative analysis of tissue bioluminescence imaging (BLI).
Figures 27A, 27B, 27C, 27D, 27E, 27F:
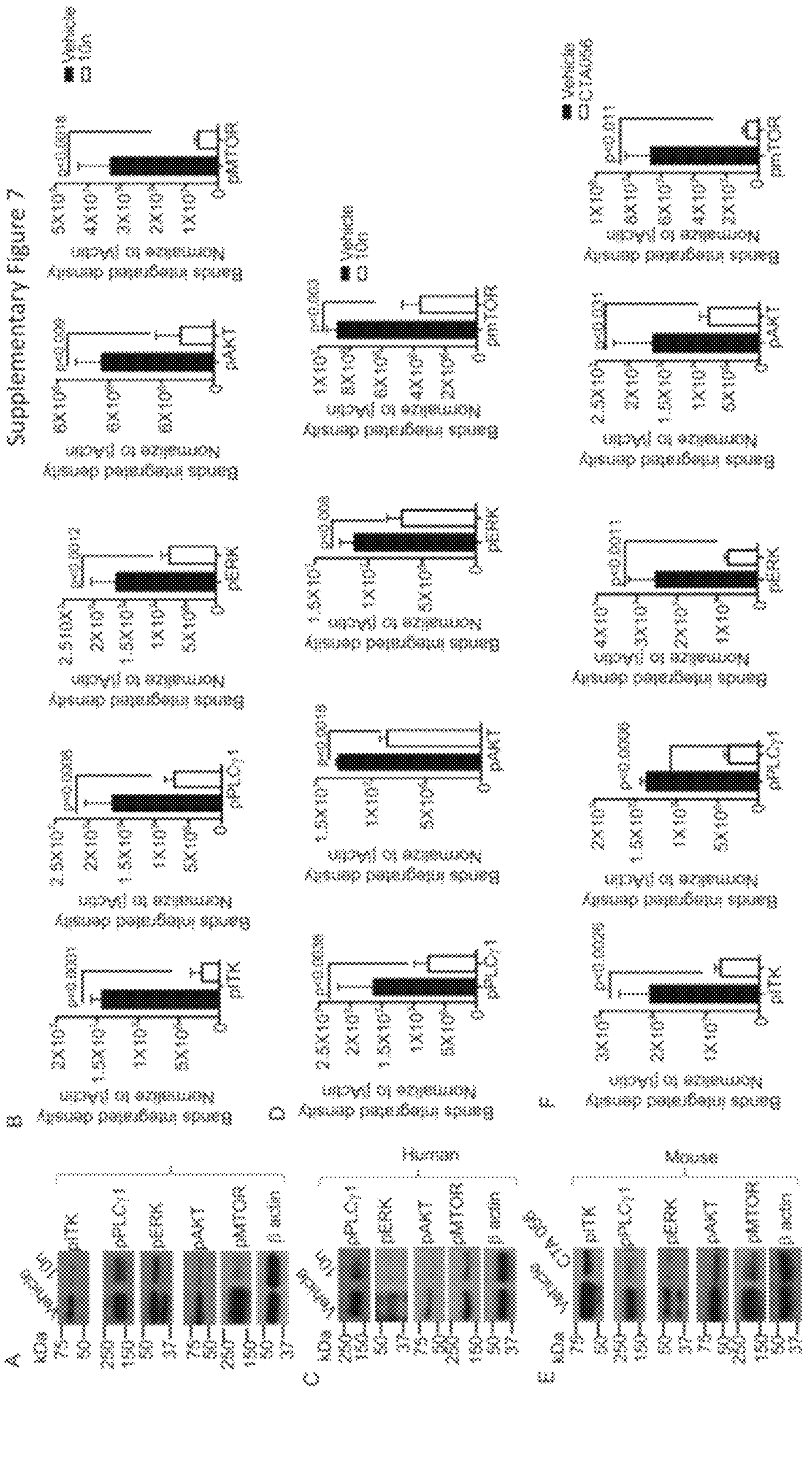
FIGS. 27A-27F depict ITK inhibitors 10n and CTA056 are not specific for ITK.

As an alternative approach, both CD8$^+$ and CD4$^+$ T cells were tracked in allo-BMT mice by using donor CD8$^+$ and CD4$^+$ T cells from WT and SLP76Y145FKI mice that also express luciferase, which could be monitored by bioluminescence (Negrin and Contag, 2006). It was observed that both CD8$^+$ and CD4$^+$ donor T cells from SLP76Y145FKI mice had significantly impaired residency in GVHD target organs—including the liver and small intestine (SI)—compared to WT, despite no differences in spleen and lymph nodes (FIG. 16G). Luciferase bioluminescence was quantified for secondary lymphoid organs (spleen and lymph nodes) and GVHD target organs (small intestine (SI) and liver) (FIG. 26A-B). These data suggest that SLP76Y145FKI CD8$^+$ and CD4$^+$ T cells display attenuated chemokine receptor expression, which correlates with defective migration to GVHD target organs and reduced target organ pathology.

More specifically, FIGS. 16A-16G depict SLP76Y145/ITK signaling is required for T cell migration to the GVHD target tissues. (FIG. 16A) Irradiated BALB/c mice were allo-transplanted and injected with FACS-sorted CD8$^+$ or CD4$^+$ T cells mixed at a 1:1 ratio from WT B6.SJL (Ly5 CD45.1) and WT C57B16 (CD45.2) mice. We also transplanted FACS-sorted CD8$^+$ or CD4$^+$ T cells from B6.SJL (Ly5 CD45.1) and SLP75Y145FKI (C57B16 in background, CD45.2) mice at a 1:1 ratio. FACS analysis of sorted T cells pre-transplant is shown. (FIGS. 16B-C) On day seven post-transplantation, the spleen, liver, and small intestine (SI) from recipients were examined for donor CD4 and CD8$^+$ T cells by H2K$^{b+}$ CD45.1$^+$ (LY5) or CD45.2$^+$ (B6). We also examined donor CD4 or CD8$^+$ T cells from WT mice by H2K$^{b+}$ CD45.1$^+$, and from SLP75Y145FKI mice by H2K$^{b+}$ and CD45.2$^+$. The ratio of WT: SLP75Y145FKI CD8$^+$ and CD4$^+$ T cells in the organs was determined. (D) We transplanted either CD4$^+$ or CD8$^+$ T cells separately into irradiated BALB/c mice, in separate experiments. At day 7 post-allo-HSCT, liver and small intestines were examined by H&E staining (10×) magnification). (FIGS. 16E-F) On Day 7 post-allo-HSCT, donor CD8$^+$ or CD4$^+$ T cells from separate experiments were isolated and examined for the expression of CXCr3, CX3r1, CXCr1, CCR12, s1pR1, CrTAM, CXCR6, CCR9, CXCR5, and CXCr4 using q-PCR. P values were calculated using 2-way ANOVA and Student's t test, p values are listed. (FIG. 16G) Irradiated BALB/c mice were BM-transplanted and injected with CD8$^+$ T cells and CD4$^+$ T cells from luciferase-expressing WT or SLP75Y145FKI mice (C57Bl/6 background). On day 7 post-allo-HSCT, recipient BALB/c mice were injected with D-luciferin. Spleen, lymph nodes, liver, and small intestine were examined for donor CD8$^+$ T cells or CD4$^+$ T cells by luciferase expression. One representative of 2 independent experiments is shown (n=3 mice/group for control, n=5 mice for WT, and n=5 mice for SLP75Y145FKI. P values were calculated using two-way ANOVA and Student's t test, p values are listed). See also FIGS. 25 and 26.

More specifically, FIGS. 25A and 25B depict quantitative analysis of donor T cells in secondary lymphoid organs and GVHD target organs. (FIG. 25A) Quantitative analysis from flow cytometry data. CD8$^+$ and CD4$^+$ T cells from WT and SLP76Y145FKI C57Bl/6 mice were transplanted into BALB/c mice (MHC haplotype d) as recipients. In several experiments, donor CD4$^+$ and CD8$^+$ T cells were analyzed for migration in the secondary lymphoid organs spleens and lymph nodes. (FIG. 25B) Quantitative analysis from flow cytometry data. In several experiments donor CD4$^+$ and CD8$^+$ T cells were analyzed for the presence of donor T cells in GVHD target organs, liver and small intestine. For statistical analysis we used two-way ANOVA and student's t test, p values are presented.

More specifically, FIGS. 26A and 26B depict quantitative analysis of tissue bioluminescence imaging (BLI). For tissue imaging experiments, allo-HSCT was performed with 10×10$^6$ WT $_{TCD}$BM cells and 1×10$^6$ FACS-sorted CD8$^+$ T cells (A) or CD4$^+$ T cells (B) (from B6-luc or SLP76Y145FKI luc mice) and bioluminescence imaging of tissues was performed as previously described (Mammadli et al., 2020). Briefly, 5 minutes after injection with D-luciferin (10 μg/g body weight), selected tissues were prepared and imaged for 1 minute. Imaging data were analyzed and quantified with Living Image Software (Xenogen) and Igor Pro (Wave Metrics, Lake Oswego, OR)

Figures 17A, 17B, 17C:
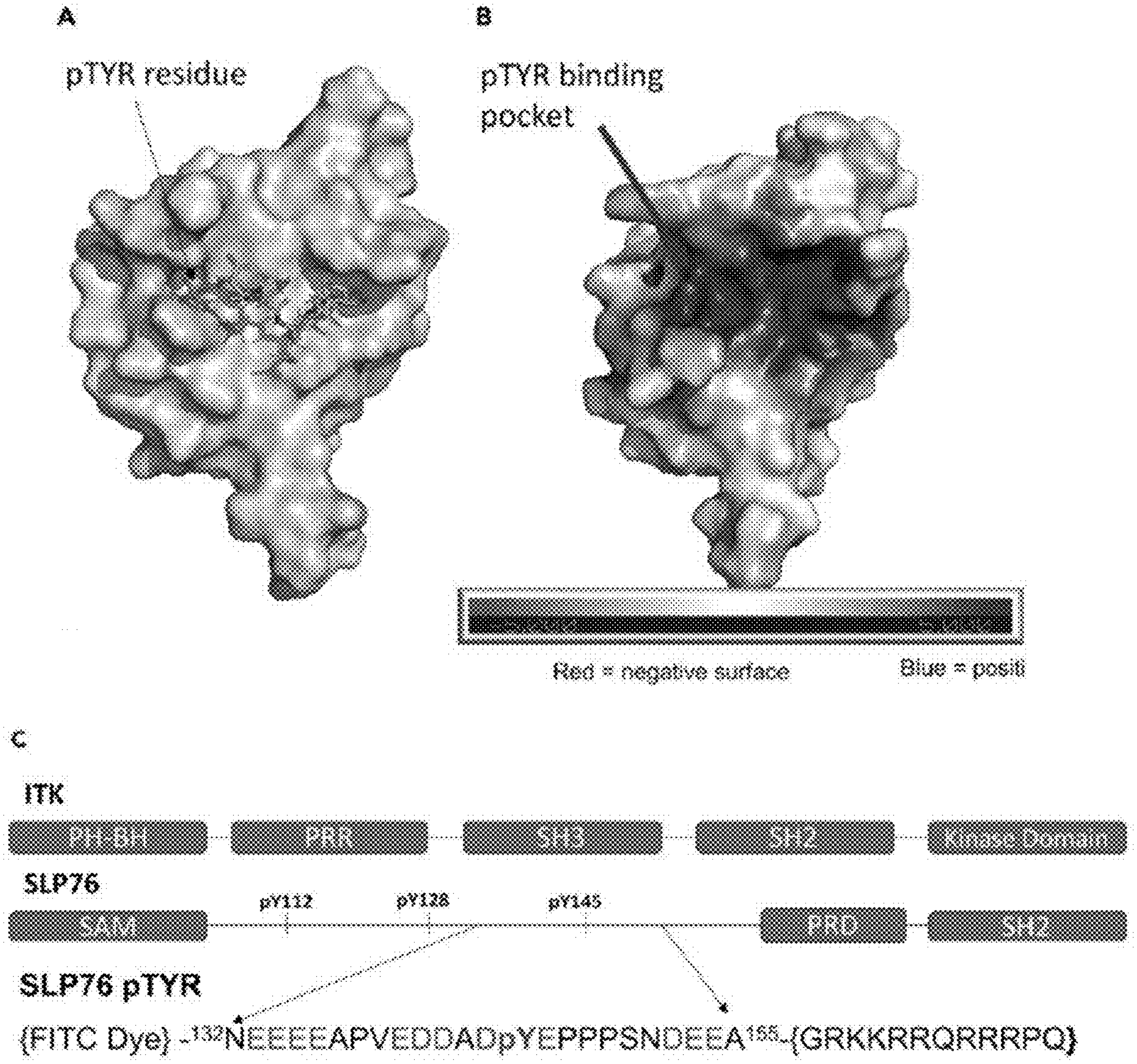
FIGS. 17A-17F (SEQ ID Nos: 2-3 and 5) depict development of a novel peptide that disrupts the interaction between SLP76 and ITK.
Figures 17D, 17E, 17F:
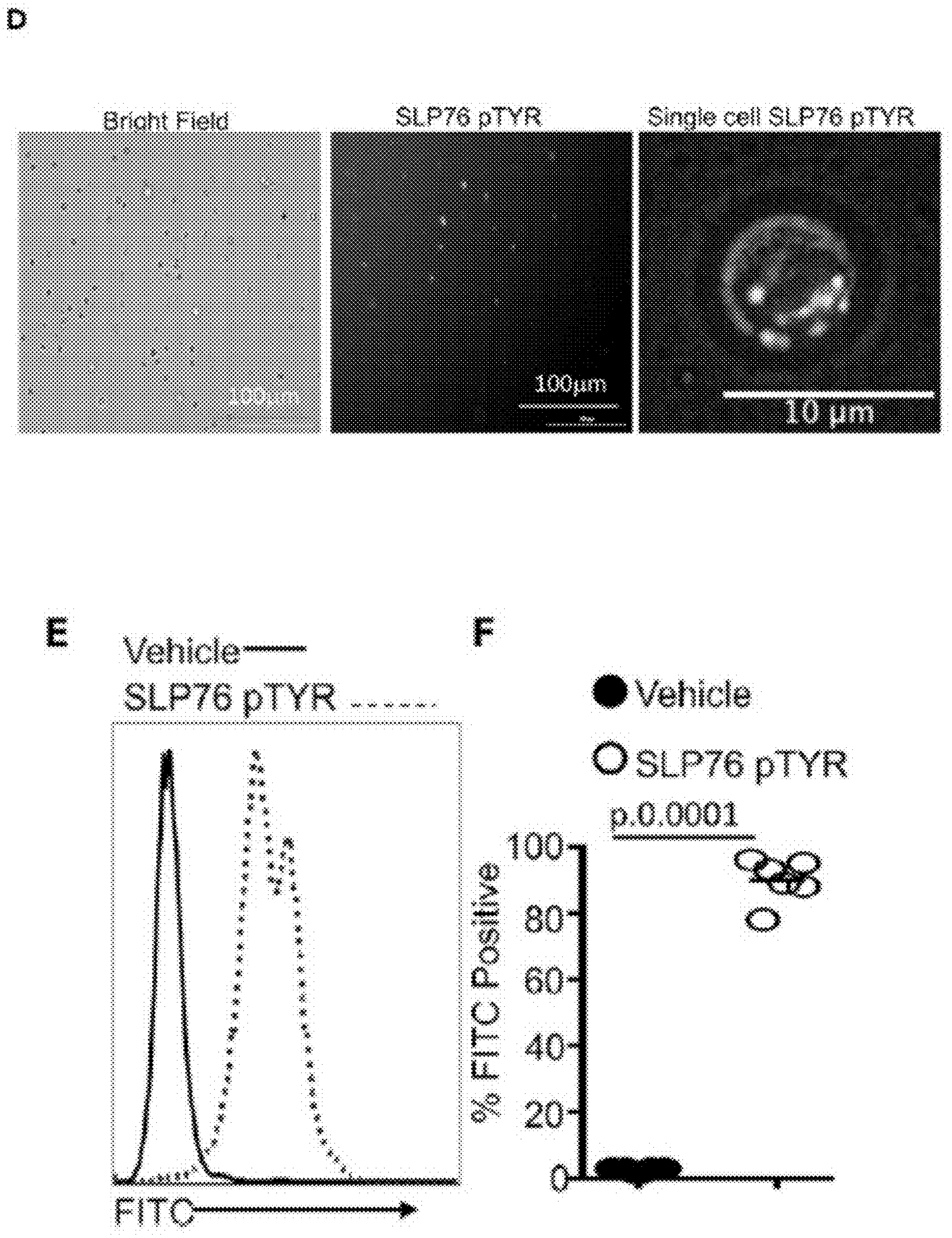

Novel peptide inhibitor SLP76pTYR specifically targets ITK signaling and enhances Treg cell development. Since T cells from SLP76Y145FKI mice can separate GVHD from GVL, we sought to determine whether disruption of ITK signaling with pharmacological agents would have a similar effect. When several commercially available small molecule inhibitors were used, including 10n (Carson et al., 2015, Riether et al., 2009), CTA056 (Guo et al., 2012) and GSK2250665A (Alder et al., 2013), we observed that these small molecules also inhibit several other kinases including mTOR and AKT, suggesting that these molecules were not specific (FIG. 27A-27F). Thus, we sought to design a novel inhibitor that would explicitly target the SLP76-ITK interaction and signaling by preventing the SH2 domain of ITK from docking onto SLP76 at tyrosine 145. Since evolution usually selects residues at specific protein: protein interfaces for certain properties (Pletneva et al., 2006), we analyzed the physico-chemical and structural properties of the interface of the SH2 domain and SLP76-pY145 in our quest to generate a potent inhibitor of the ITK-SH2 domain: SLP76-pY145 interaction (FIG. 17A,B). It was examined the Y145 region of SLP76 to design a short peptide that can inhibit ITK via competitive binding. In addition, to avoid the unintended non-specific binding of the peptide to the more than hundred other SH2 domains (and/or to other unexpected targets) in vivo (Andersen et al., 2019), many distinctive features of the SLP76 region were incorporated around the pY145 as possible. For example, the previously published atomic-resolution NMR spectroscopy structures of the SH2 domain of ITK was used, free and in complex with a short peptide containing a pTyr residue (Pletneva et al., 2006), as a guide (FIG. 17A). The SH2 domain of ITK contains a complementary electrostatic surface, because the phosphotyrosine binding pocket, as well as the surrounding surface groove, is highly positively charged, suggesting that electrostatics most likely will play a vital role in this interaction (FIG. 17B). These efforts led to the design of a novel SLP76pTYR peptide predicted to bind to the ITK SH2 domain and prevent ITK from docking onto SLP76 at the tyrosine at 145 position (FIG. 17C). BLASTing (Altschul et al., 1990) the peptide sequence of our novel peptide SLP76145pTYR against the non-redundant human proteome showed minimal identity with other proteins, suggesting that the interaction between SLP76pTYR and the SH2 domain is unique, and most likely will be specific towards ITK signaling. The SLP76pTYR construct consists of two components (FIG. 17C): (i) amino acid residues 132 to 155 of SLP76 with phosphorylated tyrosine at position 145 and (ii) a TAT peptide sequence (GRKKRRQRRRPQ) (SEQ ID NO:3) (such as viral sequences) cell for membrane penetration (i.e. $^{132}$NEEEEAPVEDDADpYEPPP-SNDEEA$^{155}$-TAT) (SEQ ID NO:5). To test the effect of this construct to inhibit the interaction of ITK and SLP76, T cells were cultured with a FITC-conjugated SLP76pTYR peptide, vehicle, or nonspecific peptide, and examined the cells for FITC uptake using microscopy and flow cytometry. It was observed that significant numbers of cells were positive for FITC following treatment with the SLP76pTYR peptide (FIG. 17D-F). The peptide was localized in specific locations in the cell as observed by imaging the cells in a single focal plane near the cover glass. This result would be expected if the peptide were binding to ITK in signalosomes in the cell (FIG. 17D).

Figures 18A, 18B, 18C, 18D:
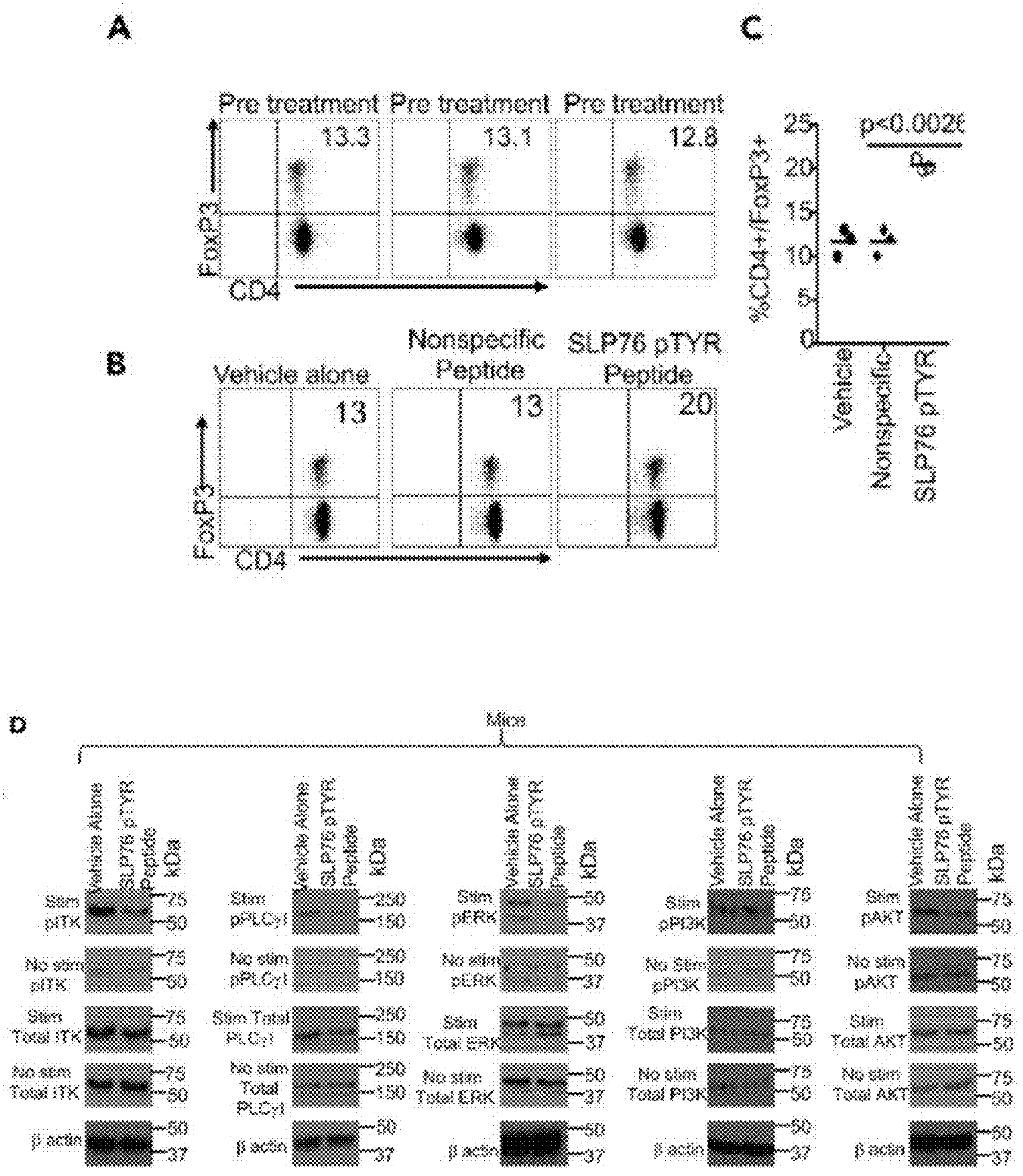
FIGS. 18A-18F depict novel peptide SLP76pTYR specifically targets SLP76: ITK signaling and enhances Treg cell development.
Figure 18E:
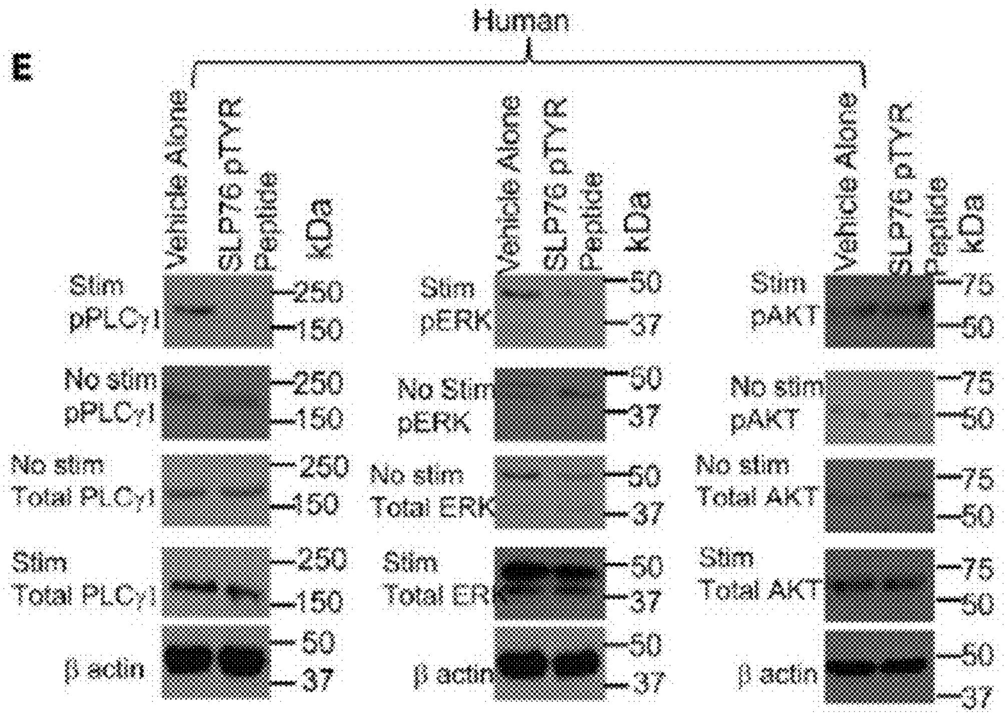
Figure 18F:
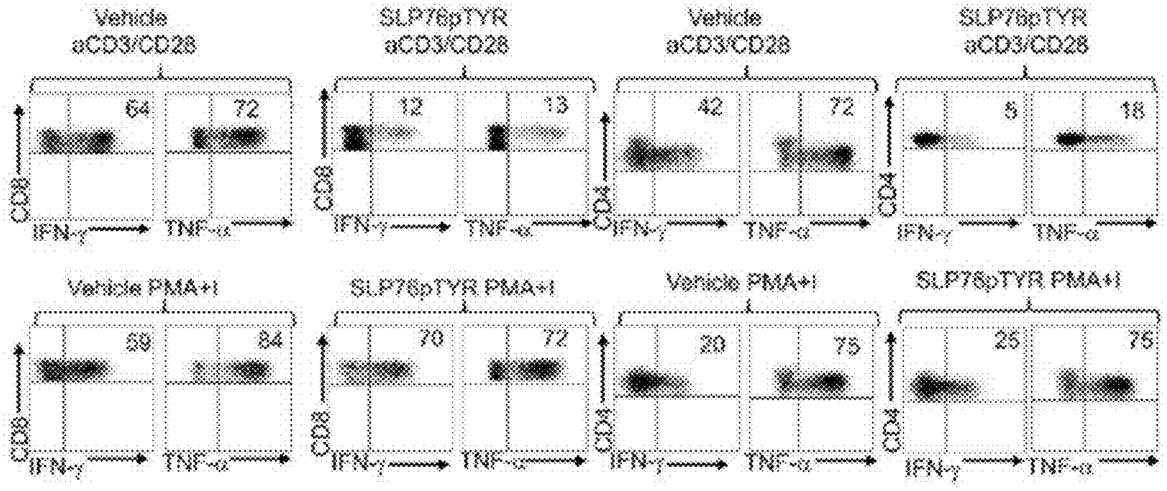
Figures 28A, 28B, 28C, 28D, 28E, 28F, 28G, 28H:
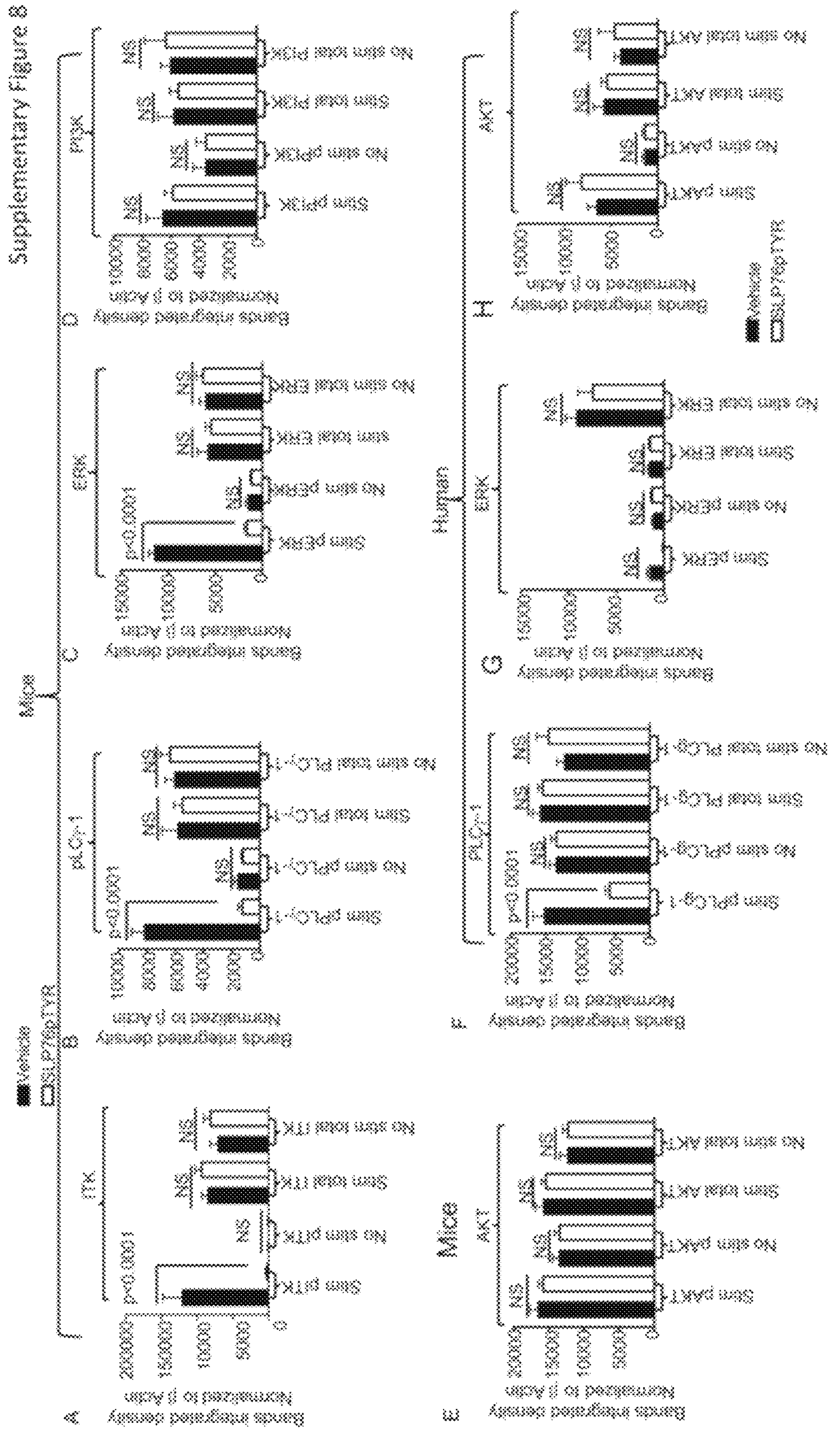
FIGS. 28A-28H depict quantitative analysis of SLP76: ITK signaling protein expression in cells treated with peptide SLP76pTYR.

ITK deficiency is known to enhance the development of regulatory T cells (Tregs) (Elmore et al., 2020, Owen et al., 2019) so the peptide inhibitor was tested to determine whether inhibition of the ITK: SLP76Y145 interactions using SLP76pTYR would induce Tregs. First, the frequency of Tregs was examined by expression of $CD4^+$ and $FoxP3^+$ (FIG. 18A). Next, total mouse T cells were stimulated with anti-CD3 (Sugie et al., 2004) in the presence of either SLP76pTYR, nonspecific peptide, or vehicle alone for 5 to 24 hours, and cells were harvested and examined for the presence of Tregs ($CD4^+CD25^+FoxP3^+$). Significantly enhanced differentiation of Treg cells in T cell cultures treated with SLP76pTYR peptide were observed compared to vehicle alone or nonspecific peptide (FIG. 18B-C). Next, mouse T cells were stimulated with anti-CD3 and anti-CD28 for 5 minutes, in the presence of SLP76pTYR or vehicle alone, and observed a reduction in ITK phosphorylation. A reduction in non-stimulated phosphorylation ITK was not observed, nor was any reduction for non-stimulated total ITK or stimulated total ITK observed. Similarly, a reduction in stimulated phosphorylation PLCγ-1 was observed; no reduction with non-stimulated phospho-PLCγ-1or either stimulated or non-stimulated PLCγ-1 was observed. Similar effects on ERK was observed as those we observed in ITK and PLCγ-1 (FIG. 18D and FIG. 28 A-C). No differences in the phosphorylation of PI3K or AKT was observed, either stimulated and non-stimulated, or on total PI3K and AKT (FIG. 18D and FIG. 28 D-E). Next, the effects of SLP76pTYR peptide on human PBMC samples from healthy human patients was investigated. T cells from these patients were stimulated with anti-CD3 (OKT3) (Karimi et al., 2005) for 5 minutes in the presence of SLP76pTYR or vehicle alone. We observed reduced phosphorylation of PLCγ1 and ERK, in stimulated T cells (FIG. 18E). No differences in non-stimulated phospho PLCγ1 and ERK were observed (FIG. 18E and FIG. 28F-G). No differences in total AKT or either stimulated or unstimulated phospho AKT was observed. No differences in stimulated or unstimulated total human AKT (FIG. 18E and FIG. 28H) was observed, providing a showing that the SLP76pTYR peptide has an impact on signaling pathways downstream of SLP76 in both mouse and human T cells. Notably, SLP76pTYR peptide exhibited minimal off-target effects against other kinases, including PI3K and AKT (FIG. 28A-H). It is possible that PI3K and AKT lie downstream of ITK, but that the specific pathways affected by the disruption of the SLP76: ITK interaction does not affect the activation of PI3K and AKT. These data provide further evidence that our peptide affects early T cells signaling (FIG. 18E). Next, the ability of SLP76pTYR peptide to affect the production of proinflammatory cytokines in human PBMCs was investigated. T cells from healthy human were stimulated with anti-CD3 (OKT3) and anti-CD28 in the presence of SLP76pTYR or vehicle alone, along with Brefeldin A. T cells incubated with SLP76pTYR or vehicle alone were also examined in the presence of PMA+lonomycin and Brefeldin A for 6 hours. The data show that T cells stimulated with anti-CD3/anti-CD28 had significantly reduced IFN-γ and TNF-α production when incubated in the presence of SLP76pTYR compared with the vehicle alone (FIG. 18F).

More specifically, FIGS. 17A-17F depict development of a novel peptide that disrupts the interaction between SLP76 and ITK. (FIG. 17A) NMR spectroscopy structure of murine ITK SH2 domain showing its complex with a peptide containing a pTyr residue (PDB code: 2ETZ) that was previously solved by Pletneva et al. The SH2 domain is rendered in surface representation (wheat), while the peptide derived from residues 143-148 of SLP76 with a sequence ($^{143}$ADpYEPP$^{148}$) is shown in stick model. In contrast, the SLP76pTYR inhibitor of the present disclosure includes residues 132-155 of SLP76. (FIG. 17B) Electrostatic profile is shown, calculated using the APBS plugin in Pymol. (FIG. 17C) Top: Organization of the domain architecture of full-length ITK showing the c-terminal Kinase domain, Src-homology 2 (SH2), the Src-homology 3 (SH3) domains, the intrinsically disordered proline-rich region (PRR), and the N-termimal Pleckstrin homology (PH) and Tec homology (TH) domains. Bottom: Organization of the domain architecture of full-length SLP76 adaptor protein showing the N-terminal SAM domain, the intrinsically disordered region containing phosphotyrosines pY112, pY128, pY145, which are followed by a proline-rich domain (PRD) and a C-terminal SH2 domain. Bottom: Design of the novel peptide, SLP76pTYR with an N-terminal FITC to monitor the peptide in cells and a C-terminal TAT sequence (GRKKRRQRRRPQ TAT sequences) (SEQ ID NO:3) for cell membrane permeability. Also shown are the amino acid sequence of residues 132-155 of SLP76, which was used to design the SLP76pTYR peptide inhibitor. (FIG. 17D) T cells were examined for percentage FITC positive by fluorescence microscopy. A single cell in focal plane near the cover glass was imaged. (FIG. 17E) Primary cells cultured with SLP76pTYR or the non-specific peptide were washed and examined for FITC expression by flow cytometry. (FIG. 17F) Quantification of the FITC expression for (E). We used two-way ANOVA for statistical analysis and confirmed our statistical finding by Student's t-test was performed. See also FIG. 27.

More specifically, FIGS. 18A-18F depict Novel peptide SLP76pTYR specifically targets SLP76: ITK signaling and enhances Treg cell development. (FIG. 18A) Murine $CD4^+$ T cells were examine for total CD4+ and FOXP3 expression prior to treatment with SLP76pTYR. n=3, and one representative experiment is shown. (FIG. 18B) Total T cells stimulated in the presence of SLP76pTYR, nonspecific peptide, or vehicle alone were examined for total CD4 cells that are $FoxP3^+$. n=3, and one representative experiment is shown. (FIG. 18C) Quantification of three experiments as in (A) (FIG. 18D) Cell lysates were obtained from mouse T cells stimulated with anti-CD3 and anti-CD28 in the presence of SLP76pTYR, or vehicle alone. Lysate from stimulated cells and non-stimulated cells were examined for phosphorylated ITK, total ITK (size 50-75 kDa), phosphorylated PLCγ1 total PLC γ1 (size ~155 kDa), phosphorylated ERK, total ERK (size ~42 kDa), phosphorylated PIC γ1, total PIC γ1, (size ~85 kDa), phosphorylated AKT, and total AKT (size ~60 kDa). n=3 and one representative experiment is shown. (FIG. 18E) Cell lysates from human T cells, non-stimulated or stimulated with OKT3 for 5 min in the presence of SLP76pTYR or vehicle alone, were examined for phosphorylated pPLCγ1 and total PLC γ1 on stimulated and non-stimulated T cells. Cell lysate from stimulated and non-stimulated cells were examine for pERK and total ERK. Lysates from stimulated and non-stimulated were also examined for phosphorylation and total AKT. n=3 and one representative experiment is shown. (FIG. 18F) Primary human T cells from PBMCs were stimulated with anti-CD3 and anti-CD28, or with PMA/lonomycin, for 6 hours in the presence of vehicle alone or SLP76pTYR in the presence of Brefeldin A (BFA) (Webb et al., 2015). Intracellular IFN-γ and TNF-α expression by $CD8^+$ and CD4+ T cells was determined by flow cytometry. For statistical analysis we used two-way ANOVA and Student's t test. P values are presented. See also FIG. 28.

More specifically, FIGS. 27A-27F depict ITK inhibitors 10n and CTA056 are not specific for ITK, Related to FIG. 5. (FIG. 27A) WT mouse T cells were cultured with either 10n or vehicle, then lysed post-incubation, and lysates were western blotted for pITK (size 50-75 kDa), pPLCγ1 (size ~155 kDa), PERK (size ~42 kDa), pAKT (size ~60 kDa), and pmTOR (size 240 kDa). (FIG. 27B) Western blots from three experiments were quantitated and normalized to actin. (FIG. 27C) T cells from primary human PBMCs were isolated and cultured with commercially available 10n or vehicle and western blotted for pPLCg1, pERK, pAKT, and pmTOR. (FIG. 27D) Western blots from three experiments were quantitated and normalized to actin. (FIG. 27E) Mouse T cells were cultured with either CTA056 or vehicle, the cells were lysed post-incubation, and lysates were western blotted for pITK, pPLCγ1, pAKT, pmTOR, and pERK. (FIG. 27F) Western blots from three experiments were quantitated and normalized to β-Actin. Two-way ANOVA and Student's t-test were used for statistical analysis.

More specifically, FIGS. 28A-28H depict quantitative analysis of SLP76: ITK signaling protein expression in cells treated with peptide SLP76pTYR. Quantitative analysis of cell lysates were obtained from mouse T cells stimulated with anti-CD3 and anti-CD28 in the presence of SLP76pTYR, or vehicle alone. Lysate from stimulated cells or non-stimulated cells were examined for phosphorylated ITK, total ITK, phosphorylated PLCγ1 total PLC γ1 phosphorylated ERK, total ERK, phosphorylated PI3K, total PI3K, phosphorylated AKT, and total AKT. n=3 and one representative experiment is shown. (FIGS. 28A-E) Quantitative analysis of cell lysates from human T cells, non-stimulated or stimulated with OKT3 for 5 min in the presence of SLP76pTYR or vehicle alone, were examined for phosphorylated pPLCγ1 and total PLCγ1 on stimulated and non-stimulated T cells. Cell lysate from stimulated and non-stimulated cells were examine for pERK and total ERK. Lysates from stimulated and non-stimulated were also examined for phosphorylation and total AKT. n=3 and one representative experiment is shown.

Figure 19A:
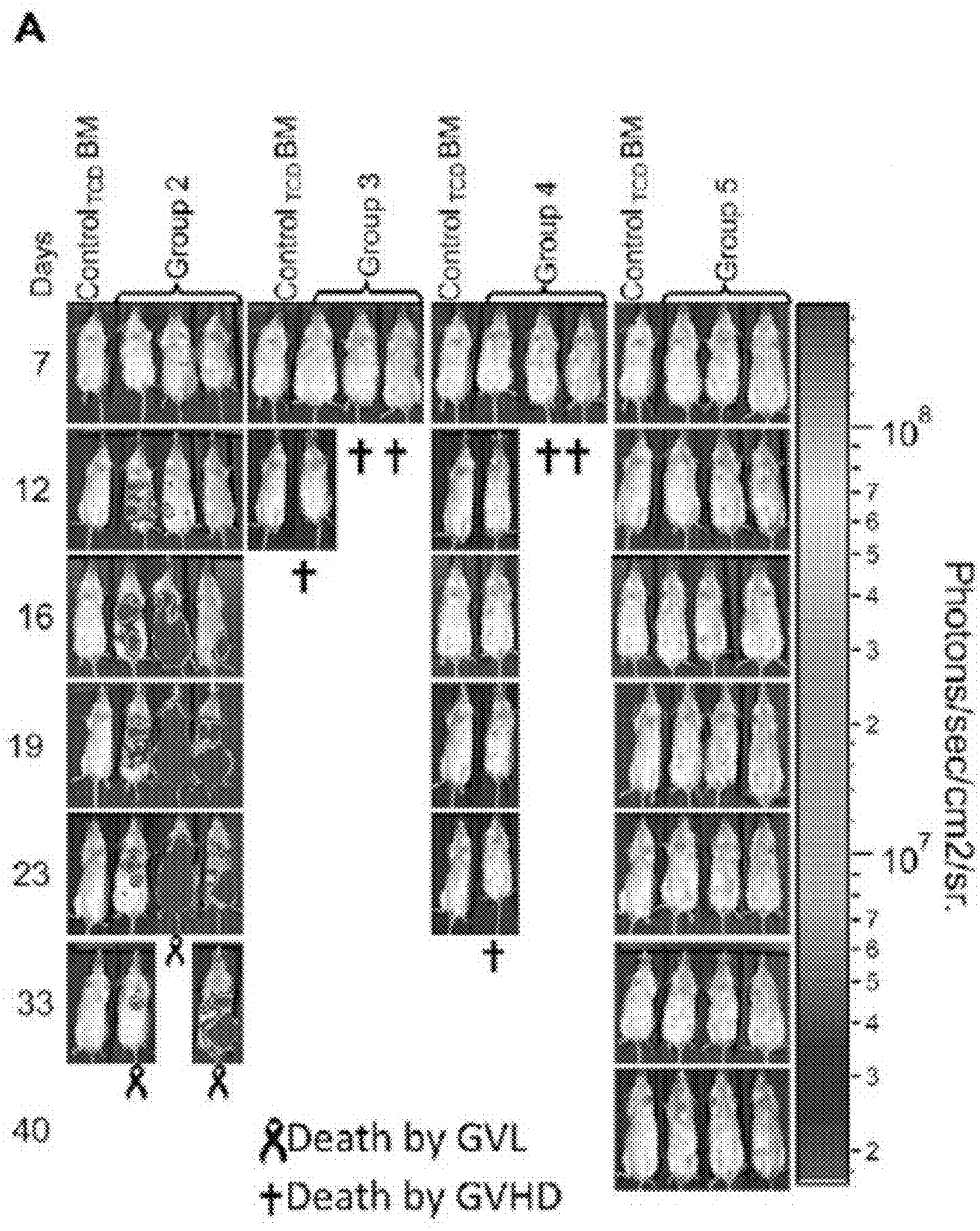
FIGS. 19A-19F depict inhibition of T cells by the peptide SLP76pTYR allows tumor clearance without inducing GVHD.
Figures 19B, 19C, 19D, 19E, 19F:
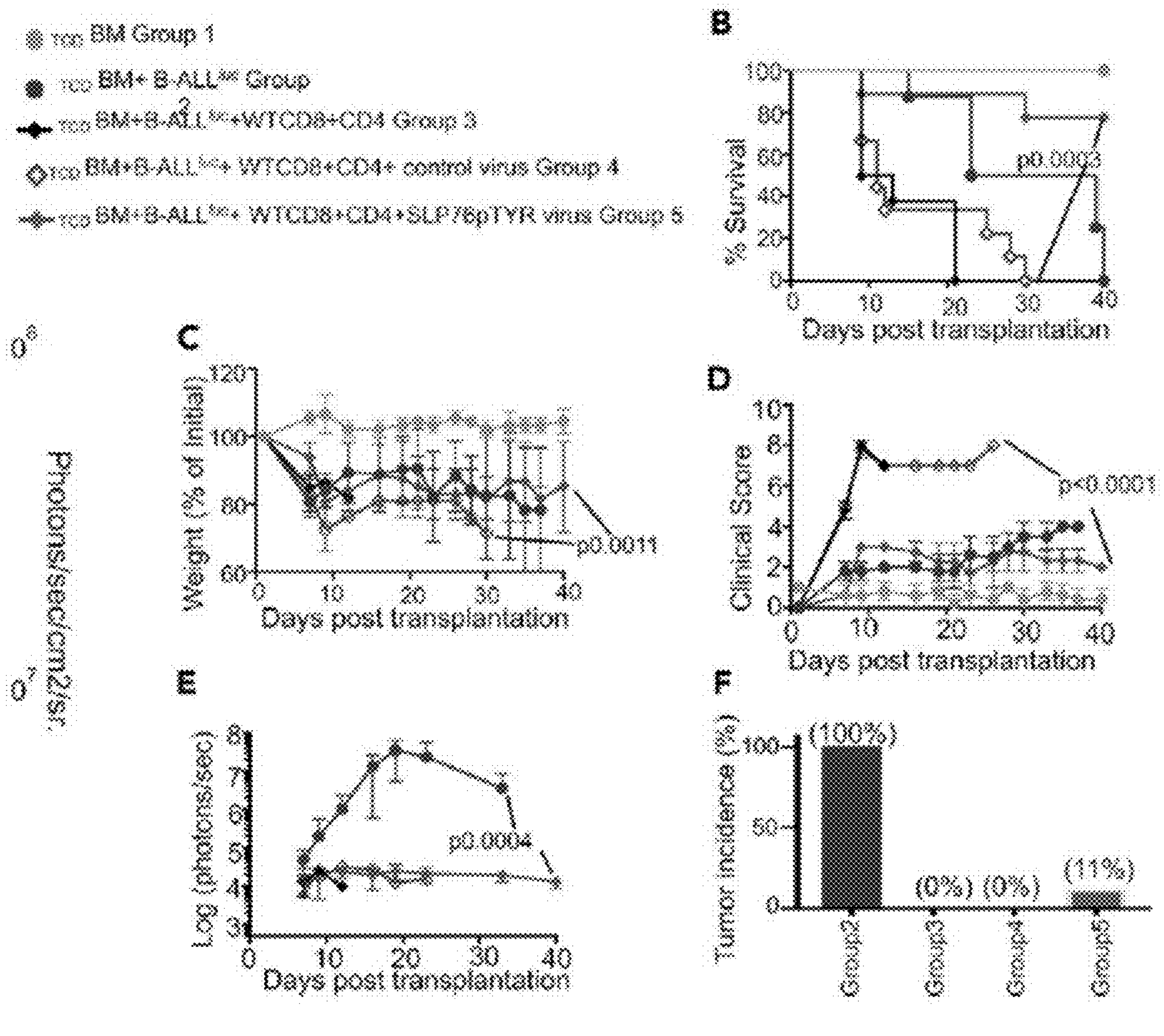

Inhibition of SLP76-ITK interaction and signaling by the peptide SLP76pTYR allows tumor clearance without inducing GVHD. Next, it was investigated whether the peptide of the present disclosure can inhibit SLP76: ITK interaction in vivo and separate GVL from GVHD as proof of principle for the approach. WT $CD8^+$ and $CD4^+$ T cells were mixed at a 1:1 ratio and transduced with a retrovirus carrying SLP76pTYR-pCherry or empty vector. Lethally irradiated recipient BALB/c mice were transplanted with $10\times10^6$ T cell-depleted BM ($_{TCD}$BM) as described, alone or together with WT $CD8^+$ and $CD4^+$ T cells transduced with SLP76pTYR-pCherry or empty vector-carrying virus. Recipient mice were also given $1\times10^5$ primary B-ALL-luc tumor cells as described (Cheng et al., 2016). While tumor growth was observed in $_{TCD}$BM-transplanted mice that did not receive donor T cells, tumor growth was not seen in mice transplanted with either untransduced T cells, or T cells transduced with either empty viruses or SLP76pTYR-pCherry carrying viruses. Notably, mice transplanted with untransduced T cells or T cells transduced with empty virus suffered from GVHD, while mice transplanted with T cells transduced with SLP76pTYR-pCherry carrying virus survived for >40 days post-HSCT without tumor growth, with minimal signs of GVHD (FIG. 19A-E). Tumor growth was observed in only 1 out of 9 mice in the group that received the T cells transduced with SLP76pTYR-pCherry carrying virus (FIG. 19F).

More specifically, FIGS. 19A-19F depict Inhibition of T cells by the peptide SLP76pTYR allows tumor clearance without inducing GVHD. (FIG. 19A) Purified WT $CD8^+$ and $CD4^+$ T cells were mixed ($1\times10^6$ total) at a 1:1 ratio, and transduced with viruses containing SLP76pTYR or empty vector, then transplanted along with $1\times10^5$ B-ALL-luc cells and $5\times10^6$ T cell-depleted bone marrow cells into irradiated BALB/c mice. Host BALB/c mice were imaged using IVIS 200 3 times a week. Group one received $10\times10^6$ T cell-depleted bone marrow alone ($_{TCD}$BM). Group two received $10\times10^6$ $_{TCD}$BM along with $1\times10^5$ B-ALL-luc cells ($_{TCD}$BM+B-ALL$^{luc}$). The third group was transplanted with $10\times10^6$ $_{TCD}$BM and a 1:1 ratio of purified WT $CD8^+$ and $CD4^+$ T cells ($1\times10^6$ total) along with $1\times10^5$ B-ALL-luc cells ($_{TCD}$BM+B-ALL$^{luc}$+WT CD8+CD4). Group four received $10\times10^6$ $_{TCD}$BM and a 1:1 ratio of purified WT $CD8^+$ and $CD4^+$ T cells ($1\times10^6$ total) transduced with control viruses along with $2\times10^5$ B-ALL-luc cells ($_{TCD}$BM+B-ALL$^{luc}$+Empty CD8+CD4). Group five received $10\times10^6$ TCDBM, a 1:1 ratio of purified WT $CD8^+$ and $CD4^+$ T cells ($1\times10^6$ each) transduced with SLP76pTYR-carrying viruses, and with $1\times10^5$ B-ALL-luc cells ($_{TCD}$BM+B-ALL$^{luc}$+SLP76pTYR virus CD8+CD4) (FIG. 19B) The mice were monitored for survival, (FIG. 19C) body weight changes, and (FIG. 19D) clinical score for 40 days post BMT. For weight changes and clinical score, one representative of 2 independent experiments is shown (n=3 mice/group for BM alone; n=5 experimental mice/group for all three group). (FIG. 19E) Quantitated luciferase bioluminescence of tumor growth. (FIG. 19F) Tumor incidence for each of the experimental groups. Statistical analysis for survival and clinical score was performed using log-rank test and two-way ANOVA, respectively. Note: Controls are naïve for tumor, but transplanted with $10\times10^6$ T cell depleted bone marrow alone ($_{TCD}$BM) and used as a negative control for BLI.

Altogether, these data demonstrate that disruption of SLP76: ITK signaling can separate GVHD from GVL. Inhibition of ITK signaling by SLP76pTYR, by specifically targeting the SLP76 and ITK interaction, allows tumor clearance and minimizes development of GVHD. Finally, our novel peptide inhibitor of ITK is specific and has the potential to be used in a clinical setting for T cell-mediated disorders. (See FIG. 12).

DISCUSSION

This report shows that targeting the SLP76: ITK interaction and its downstream factors significantly suppresses GVHD pathogenesis while maintaining GVL effects in an allo-HSCT model. Since GVHD is primarily caused by donor T cells, modulating donor T cells by specifically targeting kinase activity will enable one to separate GVHD from GVL. The data suggest that the SLP76: ITK signaling pathway could represent a potential target for the separation of GVHD and GVL responses after allo-HSCT.

The adapter protein SLP76 plays an essential role in regulating T cell activation downstream of the TCR by assembling a multimolecular signaling complex that includes ITK. The phosphorylation of SLP76 at Y145 leads to the activation and recruitment of ITK, which phosphorylates PLCγ1, leading to its activation, mobilization of calcium, and activation of the NFAT transcription factor (Sahu and August 2009). T cells that carry a Y145F mutation in SLP76 fail to phosphorylate and activate PLCγ1 in response to TCR stimulation (Jordan et al., 2008). Although T cells expressing the SLP76 Y145F mutation exhibit signaling defects downstream of TCR stimulation, not all T cell functions are lost when ITK recruitment and activation is defective. For example, SLP76Y145FKI mice can clear acute LCMV infection (Smith-Garvin et al., 2010). The ability of T cells from SLP76Y145FKI mice to induce GVL without GVHD indicates that the SLP76: ITK pathway controls these functions. Several groups have reported that both naïve $CD44^{lo}$ $CD4^+$ and $CD8^+$ T cells can induce lethal GVHD, while $CD44^{hi}$ T cells do not (Dutt et al., 2011). Since a high proportion of $CD4^+$ and $CD8^+$ T cells from SLP76 Y145F mice are $CD44^{hi}$ and $CD122^{hi}$ and express higher levels of Eomes (IMP phenotype) (Weinreich et al., 2010), the capacity of this IMP population to induce GVHD and GVL compared to $CD8^+$ and $CD4^+CD44^{lo}CD122^{lo}$ T cell populations in our allo-HSCT model was investigated. It was found that WT $CD8^+$ and $CD4^+$, $CD44^{lo}CD122^{lo}$ T cells induced acute GVHD, while $CD8^+$ and $CD4^+$ with IMP phenotype had reduced ability to do so, with significantly delayed induction of GVHD. However, animals eventually succumbed to the symptoms of GVHD, confirming previous reports (Zhang et al., 2005). Although the SLP76Y145F mice exhibit defects in the development of other T cells in addition to the IMP cells, such as iNKT (Gerth and Mattner, 2019, Muro et al., 2019) cells and gamma delta T cells (Muro et al., 2019, Navas et al., 2017), on the role of $CD8^+$ and $CD4^+$ T cells in GVL vs. GVHD was specifically focused on. It is noted that both $CD8^+$ and $CD4^+$ SLP76Y145FKI T cells with IMP phenotype as well as those lacking the IMP phenotype exhibit GVL with reduced capacity to induce GVHD. It is likely that the altered signaling experienced by the cells with the SLP76Y145FKI mutation allows these cells to be able to have anti-tumor activity in a T cell-intrinsic manner.

Recently, several convergent lines of evidence have suggested that inflammatory cytokines act as mediators of acute GVHD (Lynch Kelly et al., 2015, Holler, 2002, Ju et al., 2005). Therefore, whether donor T cells with attenuated TCR signaling might reduce cytokine storm mediated by donor T cells was investigated. The data showed that both $CD8^+$ and $CD4^+$ T cells from WT C57Bl/6 mice (MHC haplotype b) produced significantly higher cytokines both on a serum and a cellular level when transplanted into BALB/c mice. In contrast, both donor $CD8^+$ and $CD4^+$ T cells from SLP76 Y145FKI C57Bl/6 mice produced significantly less cytokines on both a serum and a cellular level. Both donor $CD8^+$ and $CD4^+$ T cells from SLP76 Y145FKI also exhibited reduced expression of chemokine receptors compared to WT donor T cells. The defective migration of donor $CD8^+$ and $CD4^+$ SLP76Y145FKI T cells likely contributes to the attenuation of GVHD. The retention of T cells in secondary lymphoid organs by FTY720-mediated inhibition of S1PR1 also ameliorates GVHD while maintaining GVL effects (Villarroel et al., 2014, Liu et al., 2012). The chemokine receptor CXCR3 has an important role in the migration of effector T cells in GVHD model (Duffner et al., 2003). CX3r1, CXCr1, CCR12, CrTAM, CXCR6, CCR9, CXCR5 and CXCR4 have been shown to play a significant role in donor T cell migration to GVHD target organs (Barrett, 2015, Castor et al., 2012, Hsiao et al., 2020). In a clinical study, blockade of these chemokine receptors by a small molecule antagonist led to a reduction in GVHD with no significant difference in relapse rates, suggesting that blocking T cell migration to target tissues could reduce GVHD severity without compromising the beneficial GVL effect (Vadakekolathu and Rutella, 2017). Activated alloreactive $CD8^+$ T cells upregulate the expression of CX3CR1 and CXCR6 after allo-HSCT (Duffner et al., 2003, Vadakekolathu and Rutella, 2017), and these receptors are important for the homing of $CD8^+$ T cells to the liver and intestines. Thus, CXCR6 deficiency or blockade of the CXCR3 and CXCR6 ligands attenuates GVHD (Duffner et al., 2003), and importantly, the GVL effect is still maintained under these conditions (Sato et al., 2005). Thus, blocking T cell migration by chemokine receptor blockade could be beneficial in the treatment of GVHD after allo-HSCT. It is shown that specific targeting of the SLP76: ITK interactions can be achieved to potentially differentially modulate GVL and GVHD by pharmacologic agents. Rather than directly inhibiting the activity of the kinase domain of ITK, which could result in complete blockage of all ITK kinase activity in T cells (and potentially non-specifically affect other tyrosine kinases), a strategy has been developed to specifically disrupt the SLP76-pY145-mediated activation of ITK function in T cells. The interaction between ITK and SLP76 involves the phospho-tyrosines at position pY145 and the proline-rich domain (PRD) of SLP76 docking onto the SH2 and SH3 domains of ITK, respectively. This multivalent anchoring of ITK on the different SLP76 docking sites results in distinct downstream signaling effects (Grasis et al., 2010). Previous work from Grasis et al. has shown that blocking the interaction between the PRD of SLP76 and SH3 domain of ITK, using a peptide mimicking the PRD of SLP76, inhibited the TCR-induced association between ITK and SLP-76 and the transphosphorylation of ITK, as well as actin polarization at the T-cell contact site and expression of Th2 cytokines (Grasis et al., 2010). Based on the findings that SLP76Y145FKI mutant T cells can mediate tumor clearance through GVL without inducing unwanted GVHD effects, we took advantage of this fact and blocked the SLP76 pY145-mediated docking of ITK through its SH2 domain. Thus, converting Y145 to F145 in SLP76 or preventing SH2 docking by our novel SLP76145pTYR peptide does not entirely abolish the interaction between SLP76 and ITK, but significantly affects ITK kinase activity and results in severe defects in specific downstream signaling pathways (Andreotti et al., 2010). Targeting this specific interaction would therefore retain signaling pathways that maintain GVL effects but ameliorate GVHD. When we utilized the SLP76pTYR peptide to specifically target ITK signaling, we observed specific effects only on ITK signaling, without significant effects on other tyrosine kinases. Furthermore, SLP76pTYR inhibition of ITK signaling also enhances Tregs frequency in vitro, confirming the peptide's ability to affect ITK signaling and T cell effector functions. We recently reported similar effects using a model of ITK deficiency (Mammadli et al., 2020)

This SLP76pTYR peptide significantly reduced IFN-γ and TNF-α production by TCR stimulated primary human T cells isolated from PBMCs. Treatment of murine donor T cells with SLP76pTYR prior to transfer resulted in tumor clearance without inducing GVHD. Future therapies involving our novel SLP76pTYR peptide inhibitor and small molecule inhibitors could potentially be an effective strategy for enhancing GVL while avoiding GVHD. Thus, more selective ITK inhibition using our SLP76pTYR peptide could be beneficial in the treatment of autoimmune diseases while maintaining T cell effector functions.

What is claimed is:

1. A synthetic nucleic acid encoding a peptide inhibitor having a sequence identity to SEQ ID NO: 2, wherein the peptide inhibitor comprises a phosphorylated tyrosine.

2. A vector comprising a nucleic acid according to claim 1.

3. A cell comprising (i) a nucleic acid according to claim 1, or a polypeptide expressed from the vector of claim 2, or (ii) the peptide inhibitor encoded by the nucleic acid of claim 1 having sequence identity to SEQ ID NO: 2, wherein the peptide inhibitor comprises a phosphorylated tyrosine, and wherein the cell is an isolated T-cell.

4. The cell of claim 3, wherein the cell is an isolated T-cell.

* * * * *